United States Patent [19]

Kearns

[11] 4,387,722
[45] Jun. 14, 1983

[54] RESPIRATION MONITOR AND X-RAY TRIGGERING APPARATUS

[76] Inventor: Kenneth L. Kearns, 12822 N. 26th Dr., Phoenix, Ariz. 85029

[21] Appl. No.: 251,713

[22] Filed: Apr. 6, 1981

Related U.S. Application Data

[62] Division of Ser. No. 963,352, Nov. 24, 1978, Pat. No. 4,289,142.

[51] Int. Cl.³ .............................................. A61B 5/08
[52] U.S. Cl. .................................................... 128/716
[58] Field of Search ............... 128/653, 671, 716, 720, 128/721, 722, 723, 724

[56] References Cited

U.S. PATENT DOCUMENTS

| | | | |
|---|---|---|---|
| 3,344,275 | 9/1967 | Marchal et al. | 128/653 |
| 3,433,217 | 3/1969 | Rieke | 128/723 |
| 3,524,058 | 8/1970 | Robertson et al. | 128/723 |
| 3,678,296 | 7/1972 | Day | 128/720 |
| 3,871,360 | 3/1975 | Van Horn et al. | 128/671 |
| 3,993,995 | 11/1976 | Kaplan et al. | 128/653 |
| 4,036,217 | 7/1977 | Ito et al. | 128/723 |

*Primary Examiner*—William E. Kamm
*Attorney, Agent, or Firm*—Cushman, Darby & Cushman

[57] ABSTRACT

Apparatus for generating a triggering signal to an x-ray machine in accordance with the respiration of a subject. A trigger signal is selectably generated to the x-ray machine just prior to occurrence of a selected respiration extrema. The value of the respiration signal at a sample occurring just after detection of the selected extrema is stored, and modified in accordance with the resolution of the system. The x-ray trigger signal is generated, if not otherwise inhibited, upon detection of the next occurrence of the modified value in the respiration wave form. Apparatus for generating signals indicative of respiration rate, respiration extrema, and heart rate is also disclosed. Apnea alarms are generated if a predetermined decrease in respiration rate is detected in successive periods in conjunction with a predetermined number of decelerating heart beats. An alarm is also generated if the respiration rate and heart rate signals appear to indicate that the respiration and heart rates are equal for a predetermined number of periods, or if the respiration or heart rates stray outside of preset threshold values. Provisions are included for adaptive DC offset, and to eliminate electromagnetic interference. Amplitude, time domain, and slew rate discrimination against artifacts are also provided.

8 Claims, 48 Drawing Figures

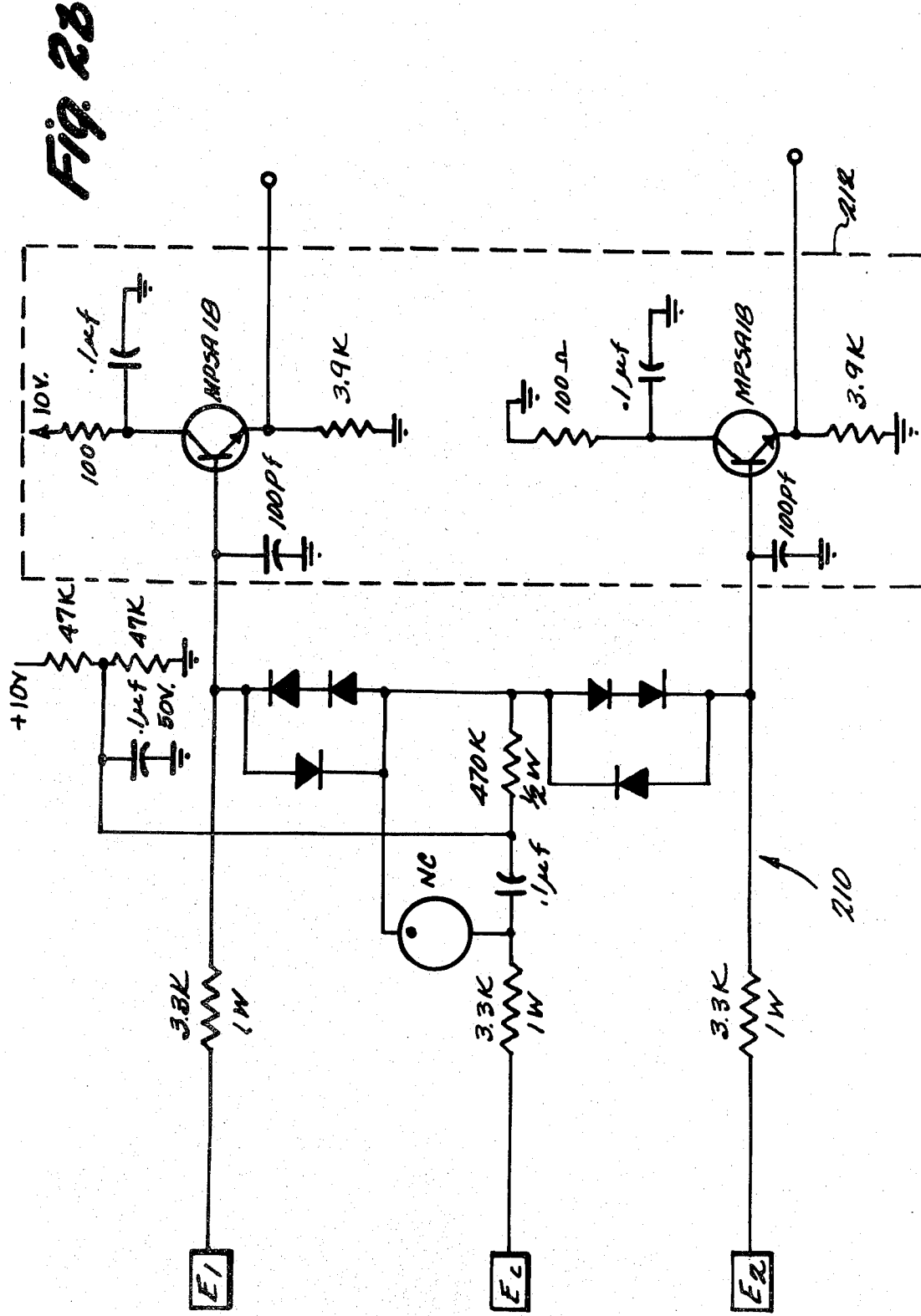

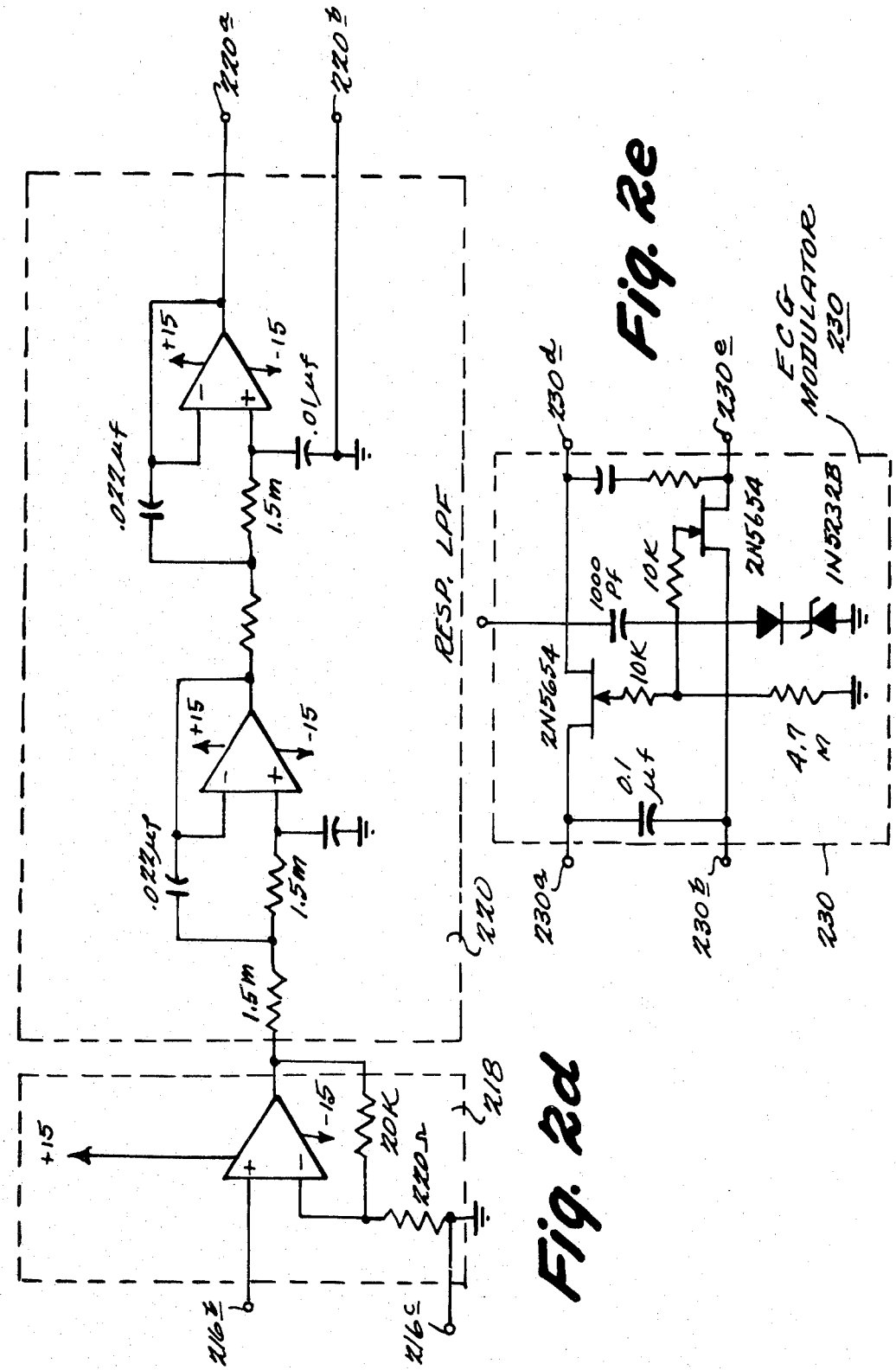

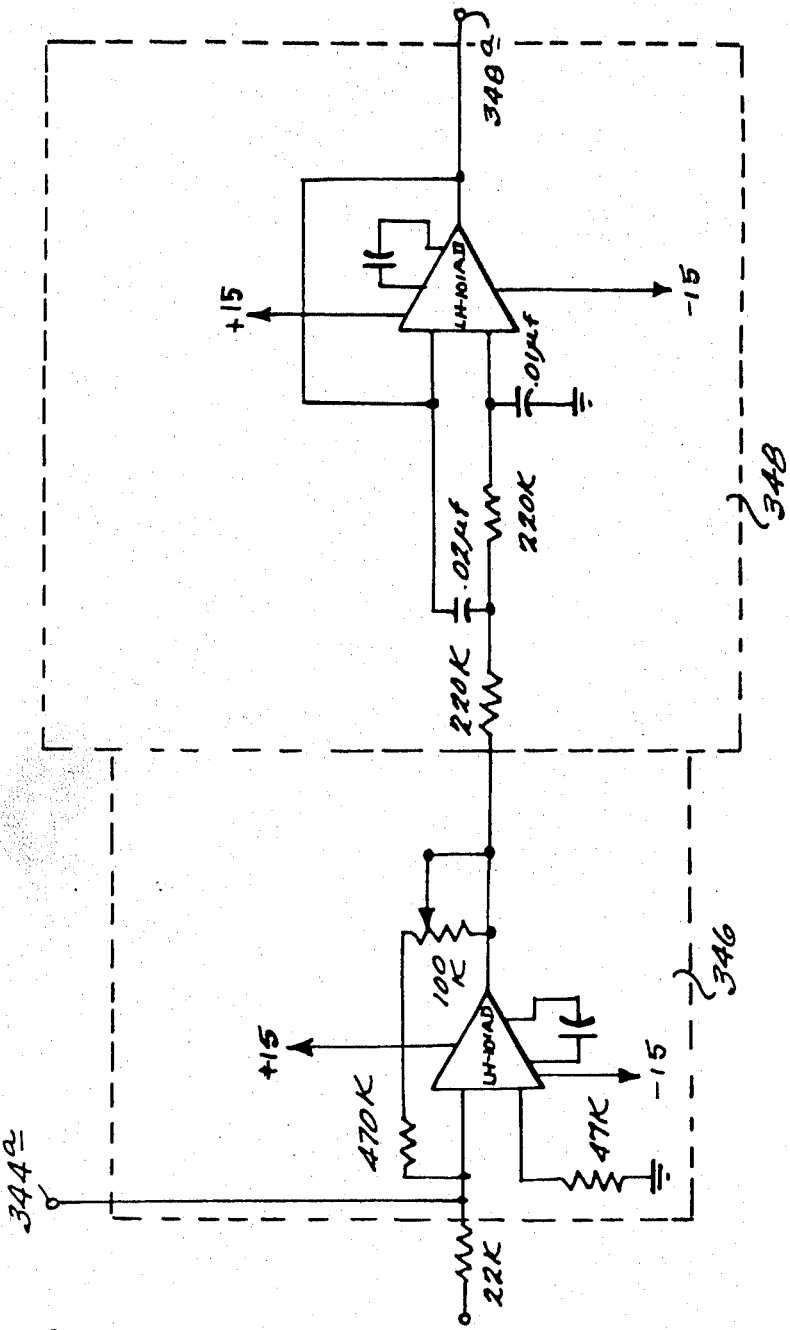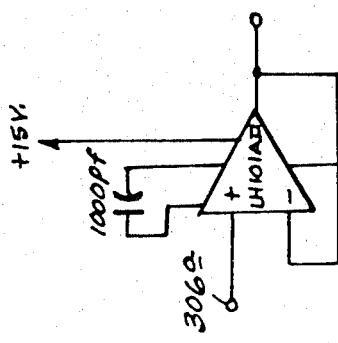

FROM FIG. 4A

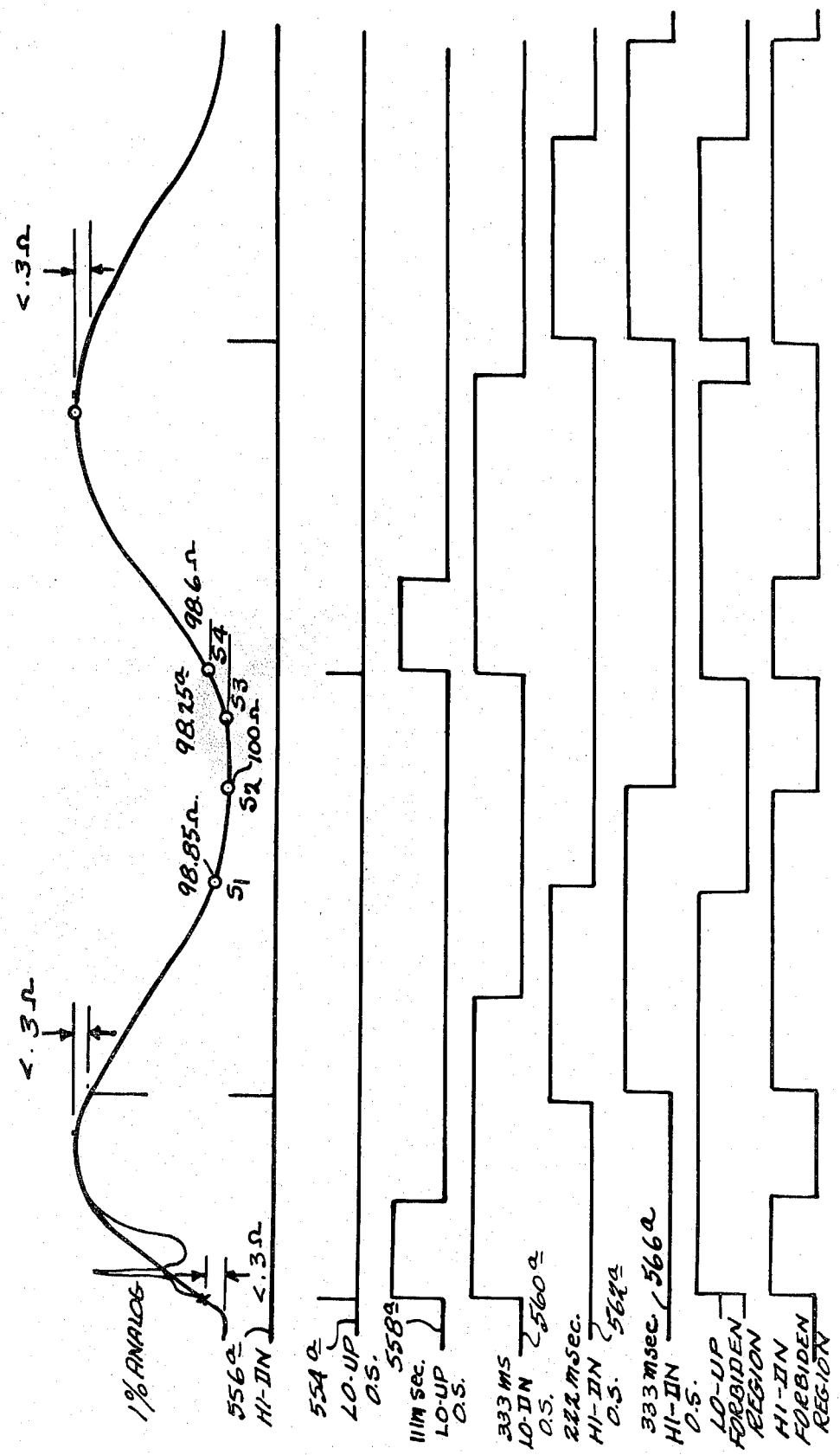

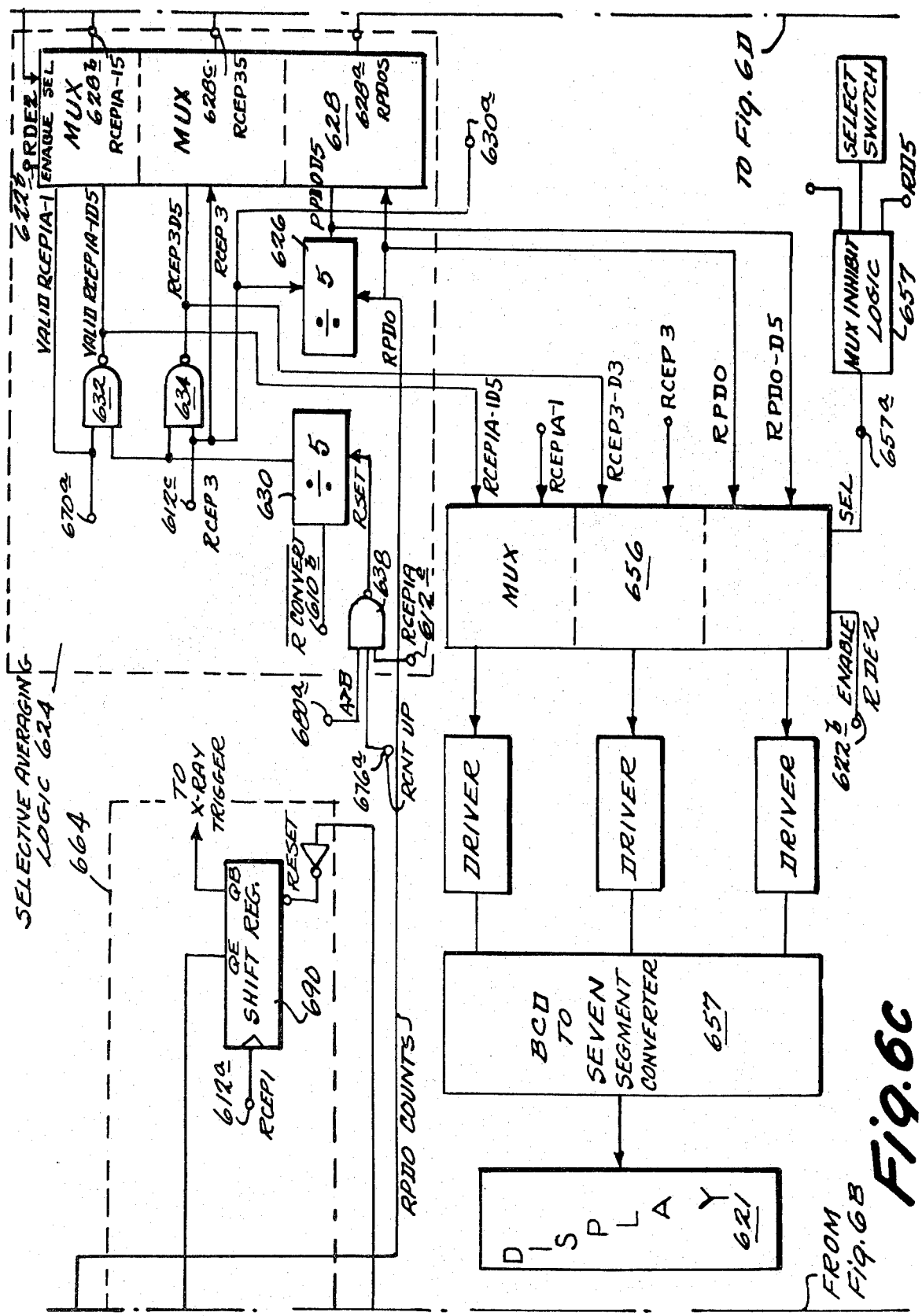

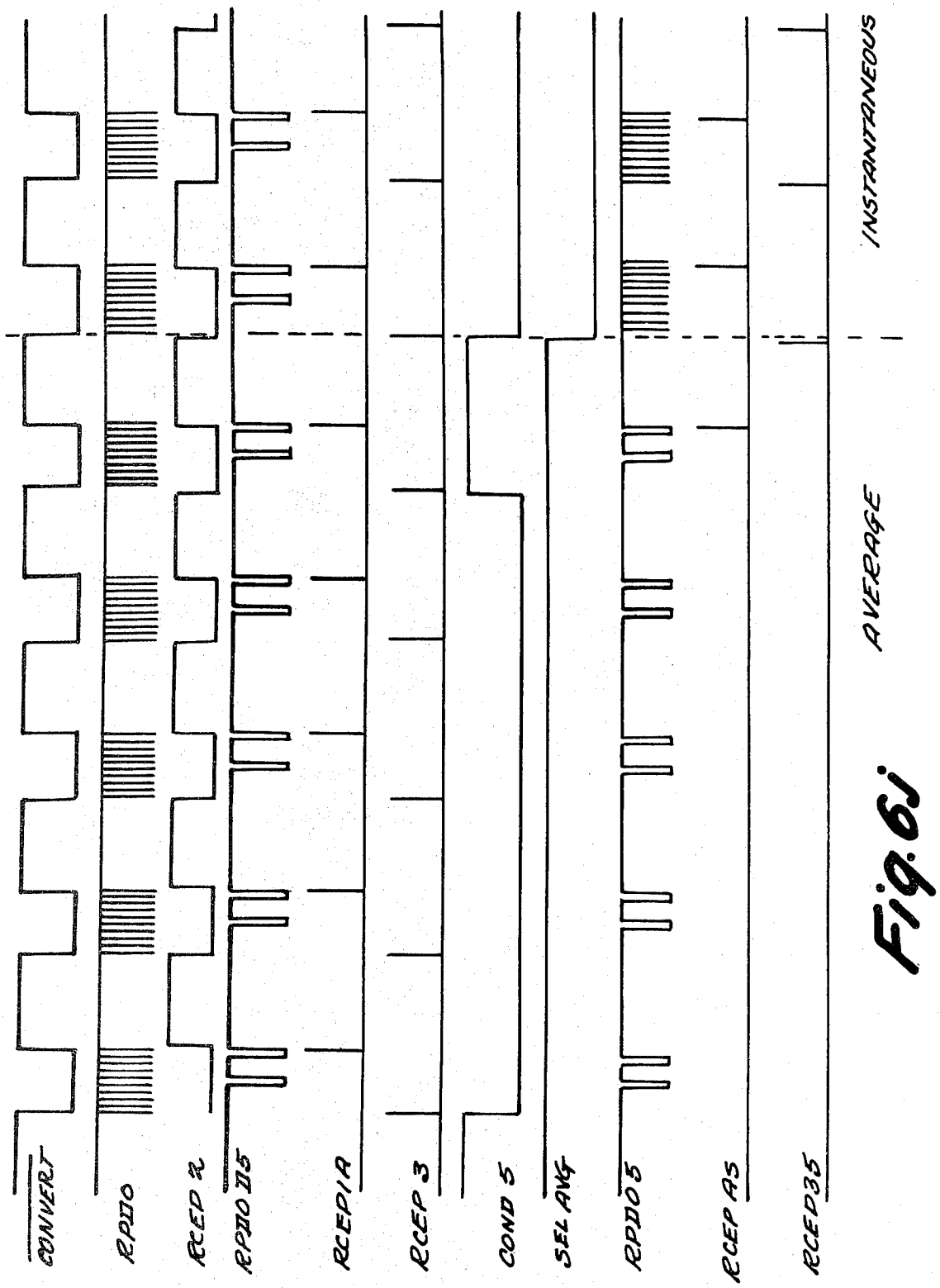

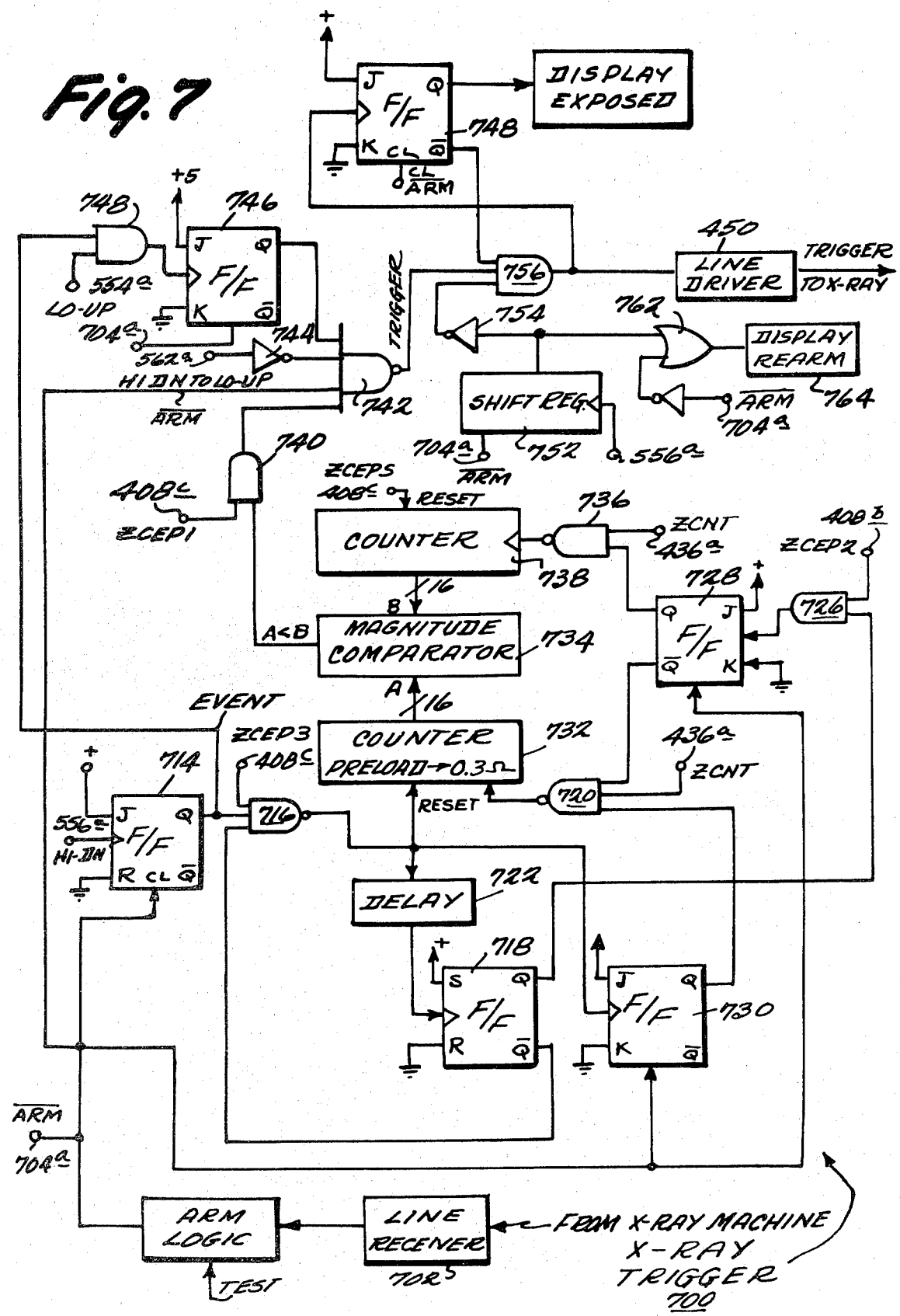

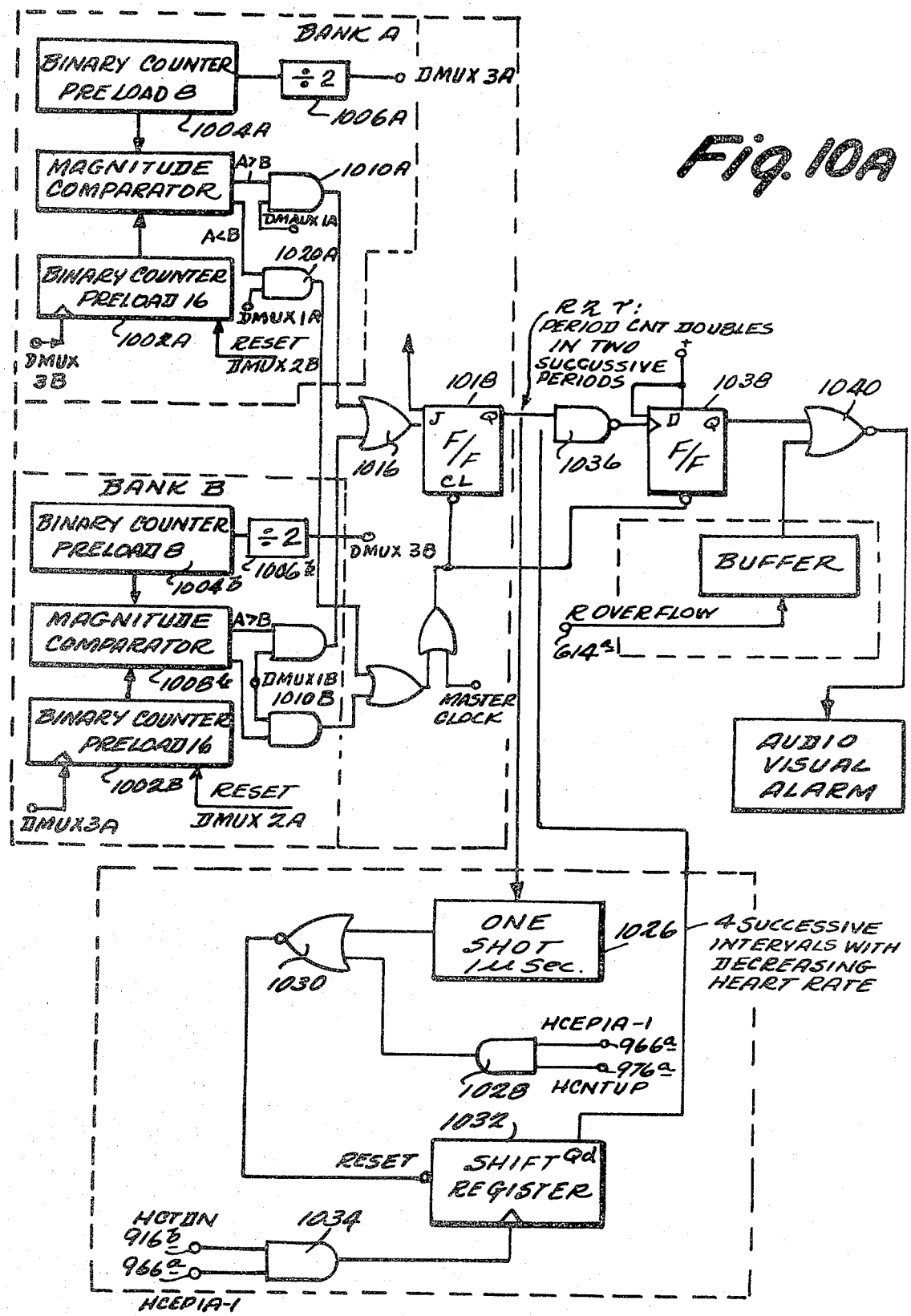

NORMAL SEQUENCES

RESPIRATION MONITOR AND X-RAY TRIGGERING APPARATUS

This is a division of application Ser. No. 963,352, filed Nov. 24, 1978, which issued as U.S. Pat. No. 4,289,142 on Sept. 15, 1981.

The present invention is directed to a respiration monitor, and, in particular, to an apparatus for triggering an X-ray machine at a predetermined desired point in the respiration cycle.

Respiration monitors, are, in general, well known. The greater percentage of the respiration monitors are, more accurately described as apnea monitors. Apnea is classically defined as the cessation of breathing efforts. Other monitors provide indicia of the respiration rate of the subject.

Various methods of sensing respiration have been utilized. For example, the air exchange between the subject's lungs and an outside source has been directly measured. A thermistor anemometer provides an electrical signal indicative of air flow by placing a thermistor in a face mask, by the nares, or mouth or in the pharynx. The resistance of the thermistor changes as it is warmed and cooled by the subject's breathing. For further description of such systems, reference is made to Gordon, D. H., Thompson, W. L.: "A new Technique for Monitoring Spontaneous Respiration," *Med Instrum*, Vol. 9, January/February 1975, pp. 21–22; Gulleminault, C. et al: "Abnormal Polygraphic Findings in Near-Miss Sudden Infant Death," *The Lancet*, Vol. 1, June 19, 1976, p. 1326; *HEALTH DEVICES*, Evaluation: Infant Apnea Monitors, Vol. 4, November 1974, p. 3; Lipton, E. L. et al: "A Respiratory Alarm for Infants," *J. Pediatr.*, Vol. 65, August 1964, pp. 294–296; Pope, J. M., Dimeff, J., Abraham, S.: "A Wireless Respiration Failure Detection System," Med. Biol. Eng., May 1974, pp. 348–354; and Rigatto, H., Brady, J. P.: "A New Nosepiece for Measuring Ventilation in Preterm Infants," *J. Appl. Physiol.*, Vol. 32, March 1972, pp. 423–424. Other methods, involving the subject breathing into a face mask include the reverse plethysmograph (wherein volume changes in a reservoir is measured with a strain gauge), a spiro meter (wherein the volume of air exhaled into a reservoir is measured) and a wet-test meter. For more complete descriptions of these respiration sensing techniques reference is made to Avery, M. E., O'Doherty, N.: "Effects of Body Tilting on the Resting End-Expiratory Position of Newborn Infants," *Pediatrics*, Vol. 29, February 1962, pp. 255–260 and Miller, H. C., Snull, N. W.: "Further Studies on the Effects of Hypoxia on the Respiration of Newborn Infants," *Pediatrics*, Vol. 16, 1955, pp. 93–103. A pneomotachograph, that is a fine mesh screen which senses pressure drops has also been used to sense respiration. Reference in this regard is made to Polgar, G.: "Comparison of Methods for Recording Respiration in Newborn Infants," *Pediatrics*, Vol. 36, December 1965, pp. 861–868; Stark, A. R., Thach, B. T.: "Mechanisms of Airway Obstruction Leading to Apnea in Newborn Infants," *J. Pediatr.*, Vol. 89, December 1976, pp. 982–985; and Warburton, D., Stark, A. R., Taeusch, H. W.: "Apnea Monitor Failure in Infants with Upper Airway Obstruction," *Pediatrics*, Vol. 60, November 1977, pp. 742–744.

Other direct respiration sensing techniques include monitoring the biometric pressure changes in a closed chamber within which the subject is disposed, (see Polgar, G.: "Comparison of Methods for Recording Respiration in Newborn Infants," *Pediatrics*, Vol. 36, December 1965, pp. 861–868); measurement of the partial pressure of carbon dioxide ($CO_2$) in the subject's exhilation (end-tidal $PCO_2$) and disposing a microphone on the subject's neck to sense the sound of air movement in the throat has been utilized.

Other methods provide signals indicative of respiration by sensing body motion. For example, air mattresses (wherein movement displaces air to cool a heated thermistor), air filled rubber vests, capacitance pneumography (wherein the subject lies between two conductive plates such that breathing movements change the capacitance between the plates), capacitance mattresses, displacement magnitometers, displacement transducers, electret pressure transducers, permanent magnetic motion transducers, peizo resistive mattresses, radar movement sensors, ultrasonic movement sensors, and strain gauges have been utilized to provide signals indicative of respiration. Further description of capacitance phneumography is provided in Barrow, R. E., Colgan, F. J.: "A Noninvasive Method for Measuring Newborn Respiration," *Respir. Care*, Vol. 18, 1973, pp. 412–414; Franks, C. I., Brown, B. H., Johnston, D. M.: "Contactless Respiration Monitoring of Infants," *Med. Biol. Eng.*, Vol. 14, May 1976, pp. 306–312 and Sigdell, J. E.: "A Theoretical Study of Capacitive Plethysomography," *Med. Biol. Eng.*, Vol. 9, September 1971, pp. 447–457. Description of displacement magnetometers are provided in Knill, R. et al: "Respiration Load Compensation in Infants," *J. Appl. Physiol.*, Vol. 40, March 1976, pp. 357–361 and Mead, J. et al: "Pulmonary Ventilation Measured From Body Surface Movements," *Science*, Vol. 156, 1957, pp. 1383–1384. The electret pressure transducer and permanent magnets motion sensors are described in Franks, C. I., Brown, B. H., Johnston, D. M.: "Contactless Respiration Monitoring of Infants," *Med. Biol. Eng.*, Vol. 14, May 1976, pp. 306–312 and *HEALTH DEVICES*, Evaluation: Infant Apnea Monitors, Vol. 4, November 1974, pg. 3. For a description of a suitable piezo resistive mattress, reference is made to Smith, J. E., Scopes, J. W.: "A New Aponea Alarm for Babies," *Lancet*, Vol. 2, 1972, pp. 545–546. Strain gauge techniques are described in Paulev, P. E. et al: "Strain-Gauge Versus Water Plethysmography: Description of Simplified Systems and Analysis of Differences and Accuracy," *Med. Biol. Eng.*, Vol. 12, July 1974, pp. 437–445 and Polgar, G.: "Comparison of Methods for Recording Respiration in Newborn Infants," *Pediatrics*, Vol. 36, December 1965, pp. 861–868. Radar sensing techniques are described in Bloice, J. A., Caro, C. G.: "Contactless Apnoea Detector Using Low Energy Radar," *J. Physiol.*, Vol. 223, February 1972, pp. 3–4; Caro, C. G., Bloice, J. A.: "Contactless Apnoea Detector Based on Radar," *Lancet*, Vol. 2, October 30, 1971, pp. 959–861 and Franks, C. I., Brown, B. H., Johnston, D. M.: "Contactless Respiration Monitoring of Infants," *Med. Biol. Eng.*, Vol. 14, May 1976, pp. 306–312. And in U.S. Pat. No. 3,993,995 (Kaplan et al, 1976). Ultrasonic motion sensors are described in "Ultrasonic Recording of Fetal Breathing," H. B. Meire et al, *British Journal of Radiology*, Vol. 48, No. 570, pp. 477–480, January 1975, patent associated literature B010-7506-B and U.S. Pat. Nos. 3,802,253 (Lee, 1974), 3,856,985 (Yokoi et al, 1974) and 3,864,660 (Ranalli et al, 1975).

Other respiration sensing techniques include the use of an electromyograph, which senses electrical activity associated nerve and muscle activation during breathing; use of a catheter placed in the esophagus to measure intra-esophageal pressure (reflecting intrathoracic pressure) during breathing; and use of photoelectric plethysomograph (hemodensitometer) which senses the absorption of particular wavelengths of incident light by the subject's blood. For a description of intra-esophageal pressure measurement techniques reference is made to Stark, A. R., Thach, B. T.: "Mechanisms of Airway Obstruction Leading to Apnea in Newborn Infants," *J. Pediatr.*, Vol. 89, December 1976, pp. 982-985 and with respect to the hemodensitometer, Wallace, J. D., et al: "Observation of Pulse and Respiration in the Neonate, A Preliminary Report," *IEEE Trans. Biomed. Eng.*, Vol. 20, September 1973, pp. 388-391.

Still another respiration sensing technique is that of impedance pneumography. Impedance pneumography involves sensing the changes in impedance across the thorax during respiration. A 10 kHz–100 kHz electric current on the order of 50 $\mu$a is passed through electrodes taped on the subject's thorax. A voltage is developed and measured. The voltage, proportional to the transthoracic impedance, varies directly in accordance with the respiratory cycle. The change in impedance is believed to be caused by a change in blood volume in the vessels supplying blood to the lungs and in part to the volume of air in the lungs themselves.

All of the above noted sensing techniques provide electrical signals which are directly indicative of the respiration cycle. The respiration cycle is then analyzed and apneic episodes detected, respiratory rate computed, or both.

Other apnea monitors sense various short term physiological effects of apnea. When respiration ceases, changes in the partial pressure of arterial oxygen ($P_{AO_2}$), arterial $CO_2$($P_{AOC_2}$), arterial pH, heart rate, skin color and blood pressure are evidenced. For example, heart rate generally decreases during apnea. Some intensive care units utilized heart rate monitors rather than respiration monitors to detect apnea.

Use of apnea monitors is particularly wide spread in infant intensive care units. Newborn infants with respiratory problems are particularly subject to apneic episodes. Often only a mild stimulus such as a noise or light body contact (e.g., squeezing the infants foot), is necessary to induce the infant to resume breathing. In other instances, only a vigorous shake or body repositioning is necessary to induce resumption of breathing. In other cases, use of resuscitator mechanisms are necessary to reinitiate breathing. However, while resumption of breathing may often easily be induced, irreversible damage to the infant can occur if the apneic episode is not promptly detected. Apnea undetected for as little as 30 seconds can cause irreversible damage to the infant and can be fatal if undetected for as little as a minute.

The problems with presently available commercial respiration monitors and apnea detectors are addressed in "Evaluation Infant Apnea Monitors," *HEALTH DEVICES*, Vol. 4, No. 1, 1974 by the Emergency Care Research Institute, and in the final report "An Investigation to Determine the Risks and Hazards Associated with Apnea Monitors," E.C.R.I. 410-276, July 1978 presented to the Bureau of Medical Devices of the Federal Food and Drug Administration. In the final report, it is noted that the primary shortcoming of the presently available apnea monitors is that the monitors tend to fail to discriminate between artifacts and the actual respiration waveform.

Commercially available apnea detectors are particularly subject to detection of signals not related to breathing (artifacts) and erroneously identifying the artifact signals as the respiratory waveform. Artifacts commonly arise from cardiovascular activity, electromagnetic interference, self-noise, vibration, line voltage fluctuation, poor electrode contact and placement and neuromuscular activity. Detection of artifact signals as the respiration waveform is referred to as a "false negative."

With respect to the problems of false negatives, reference is made to Blake, A. M. et al, "Clinical Assessment of Aponea-Alarm Mattress for Newborn Infants," *Lancet*, July 1970, pp. 183-185; Edwards, N. K. et al, "Phantom Breathing in Monitored Infants," *Am. J. Dis. Child.*, Vol. 125, May 1973, pp. 684-685; Guilleminault, C. et al, "A Polygraphic Study of the Sleep and Respiration Patterns of Apneic Premature Infants On and Off an Oscillating Water Bed," In Apnea of Prematurity, Report of the Seventy-First Ross Conference on Pediatric Research, Lucey, J. F., Shannon, D. C, Soyka, L. F., eds, Columbus, Ohio, Ross Laboratories 1977, pp. 29-34; Guilleminault, C. et al, "Apneas During Sleep In Infants: Possible Relationship with Sudden Infant Death Syndrome," *Science*, Vol. 190, November 1975, pp. 677; *HEALTH DEVICES*, Evaluation: Infant Apnea Monitors, Vol. 4, November 1974, p. 3; Lewak, N., "Sudden Infant Death Syndrome in a Hospitalized Infant on an Apnea Monitor," *Pediatrics*, Vol. 56, 1975, pp. 296-298; Mangat, D., Orr, W. C., Smith, R. P., "Sleep Apnea, Hypersomnolence, and Upper Airway Obstruction Secondary to Adenotonsillar Enlargement," *Arch Otolarygol*, Vol. 103, July 1977, pp. 383-386; Peabody, J. L., Philip, A. G. S., Lucey, J. F., "Disorganized Breathing - an Important Form of Apnea and Cause of Hypoxia," *Society for Pediatric Research Annual Meeting*, San Francisco, CA, April 27-29, 1977. Abstracted, Pediatr. Res. 11: 540, 1977; Peabody, J. L. et al, "Failure of Conventional Respiratory Monitoring to Detect Hypoxia," *Society for Pediatric Research*, San Francisco, CA, April 27-29, 1977. Abstracted, Pediatr. Res. 11:539, 1977; Rolfe, P., "Monitoring in New Born Intensive Care," *Biomed. Eng.*, Vol. 110, November 1975, pp. 399-404; Stark, A. R. et al, "The Pediatric Pneumogram: A New Method for Detecting and Quantitating Apnea in Infants," *J. Pediatr.*, Vol. 89, December 1976, pp. 982-985; and Warburton, D. et al, "Apnea Monitor Failure in Infants With Upper Airway Obstruction," *Pediatrics*, Vol. 60, November 1977, pp. 742-744.

It has been further noted that available apnea monitors which utilize sensors which do not measure the actual exchange of air are inadequate in detecting upper airway obstructions.

Conversely, a second shortcoming of the presently available apnea monitors is a tendency to trigger false apnea alarms while the infant is breathing normally (false positive). False positive alarms do not pose an immediate threat to the subject. However, such failures tend to undermine the operator's confidence in the machine, sometimes causing personnel to ignore or disable the alarms. In this regard, reference is made to Edwards, N. K. et al, "Phantom Breathing in Monitored Infants," *Am. J. Dis. Child.*, Vol. 125, May 1973, pp. 684-685; Henning L., "Impact of the Apnea Monitor on Family Life," *NICHD*, Prenatal Biology and Infant Mortality Branch, 1974, pp. 19-22; Rolfe, P., "Monitoring in New Born Intensive Care," *Biomed. Eng.*, Vol. 10, November 1975, pp. 399-404; and Stein, I. M. et al, "The Pediatric Pneumograph A New Method for Detecting and Quantitating Apnea in Infants," *Pediatrics*, Vol. 55, May 1975, pp. 599-603. Systems using sensors which directly measure air exchange, however, are often not suitable for use on infants. For example, monitoring techniques using face masks obscure the view of the nose and mouth. The face mask in and of itself, tends to cause a resistance to breathing and an increase in anatomical dead space. The face masks are generally too large and cumbersome for use on infants and entail a likelihood of rebreathing. In addition, the masks are often difficult to clean.

The various mattress and transducer pad monitoring techniques are extremely sensitive to body movements and vibration artifacts. The mattress sensors are often extremely susceptible to physical damage and deterioration and are hard to clean.

Irrespective of the method of respiration sensing utilized, the respiration monitor must be compatible for use with other diagnostic machinery such as an ECG, X-ray machines or defibrillating apparatus. For example, where an infant is in an intensive care situation, respiration and ECG are normally monitored. If the infant is removed from the monitor in order to take X-rays, there is a clear and present danger that the infant will have an apneic episode or cardiac arrest during the period when the X-rays are being taken. In graphic terms, there is a likelihood that good X-ray pictures will be taken of a dead infant. Accordingly, it is desirable that all diagnostic analysis be provided by a single monitor, compatible with an X-ray machine.

In addition, it is often desirable to utilize a respiration monitor for triggering an X-ray machine. For example, X-ray pictures for study of the lungs should be taken at points of maximum inhalation when the lungs are fully inflated. Similarly, X-ray pictures for examination of the area surrounding the lungs should be taken at points of maximum exhalation, when the lungs are fully deflated. Such instances of maximum inhalation or exhalation shall hereinafter be collectively termed "respiration extrema." X-ray pictures for examination of other thoracic areas are also taken at points of respiration extrema to minimize motion artifacts. However, triggering an X-ray machine at the proper time within the respiratory cycle is exceedingly difficult with respect to an uncooperative subject such as an infant. Examples of respiration monitor apparatus used for triggering an X-ray machine in synchronism with the respiratory cycle are described in the aforementioned U.S. Pat. Nos. 3,993,995 (Kaplan et al, 1976) and 3,524,058 (Robertson et al, 1970).

SUMMARY OF THE INVENTION

The present invention provides a respiration monitor, and X-ray trigger apparatus which is not subject to erroneous identification of non-breathing related artifacrs as the respiration waveform, or subject to false indication of apnea.

A DC coupled, frequency insensitive preamp provides a true, non-phase distorted representation of the sensed analog respiration signal. An undistorted representation of the ECG signal (diagnostic quality) is also provided. An adaptive DC offset correction whereby a predetermined percentage (e.g., 90%) of the DC offset is subtracted from the analog signal is performed. The adaptive DC offset correction, in effect, improves the information to DC offset level (percent modulation) by a factor of 10, and reduces the voltage range of the analog signal to a point where digitalization becomes practicable. A digital representation of the respiration cycle is thus provided. The ECG signal is also digitized.

The digital signals are analyzed to determine respiration extrema, respiration rate and heart rate. Apnea episodes are indicated and/or other alarms actuated when the detected respiratory rate decreases by a predetermined precentage (e.g., 50%), in successive breaths, accompanied by a predetermined number (e.g., 4) of successive periods of heart rate deceleration; if the respiration period exceeds a predetermined duration; if the respiratory rate exceeds operator set maximum and minimum threshold values; if the heart period exceeds a predetermined duration; if the heart rate exceeds operator set maximum or minimum threshold values; or if the detected respiratory rate approximately equals the detected heart rate for more than a predetermined number of periods.

Artifact rejection is provided by the DC coupling of the system and by amplitude, slew rate and time domain discrimination based upon known physical parameters of the respiration waveform and cardiac components. Generation of an alarm if detected respiration and heart rates are equal provides a failsafe against erroneous identification of the cardiac component as the respiration waveform. In addition, an indication of the relative quality of electrode contact and thus of the data is provided.

BRIEF DESCRIPTION OF THE DRAWING

A preferred exemplary embodiment will hereinafter be described in conjunction with the attached drawings, wherein like numerals denote like elements, and:

FIG. 2b is a schematic diagram of a suitable overvoltage protection circuit 210 and differential amplifier 212;

FIG. 2d is a schematic diagram of a suitable amplifier 218 and low pass filter 220;

FIG. 2e is a schematic diagram of a suitable phase synchronous modulator 230;

FIG. 3i is a schematic diagram of suitable voltage follower 344;

FIG. 3j is a schematic diagram of suitable amp 346 and low pass filter 348;

FIG. 5a is a diagram illustrating the time relationship of various signals associated with time discriminator 500;

FIGS. 6a, 6b, 6c and 6d are a block diagram of respiration tachometry circuit 600;

FIG. 6g is a schematic diagram of suitable timing logic 612;

FIG. 6j is a timing diagram relating to selective averaging logic 624;

FIG. 7 is a schematic block diagram of X-ray trigger circuit 700;

FIGS. 10a, 10b and 10c are a block schematic of physiological apnea detector 1000;

DETAILED DESCRIPTION OF A PREFERRED EXEMPLARY EMBODIMENT

Figure 1:
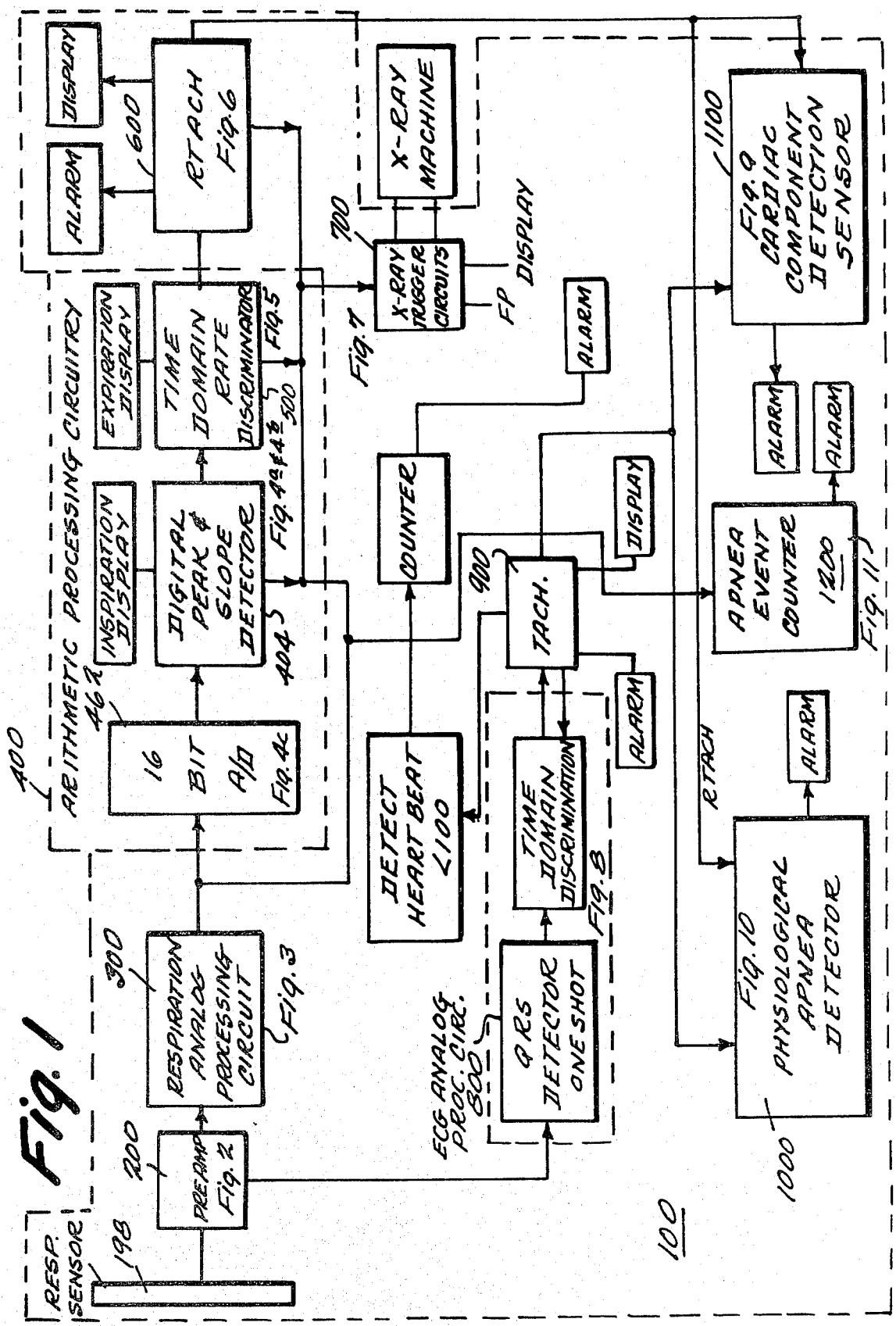
FIG. 1 is a block diagram of a respiration monitor in accordance with the present invention.

Referring now to FIG. 1 there is shown a block diagram of a respiration monitor in accordance with the present invention. A respiration sensor 198 provides output voltage directly indicative of the respiration cycle of a patient. Respiration sensor 198 may be any device which provides a signal, directly indicative of respiration. However, in the preferred embodiment, respiration sensor 198 is an impedance pneumograph. An impedance pneumograph sensor 198 is particularly advantageous in that measurement of the ECG can be effected through the same electrodes.

In impedance pneumography, a low level, high frequency carrier signal is injected into the thorax. A voltage is developed which is indicative of the transthoracic impedance of the subject. The transthoracic impedance changes as a function of the respiration cycle. The injected carrier may be of a wide range of frequencies and amplitudes, limited primarily in that the signals should be below neural response levels. Sinusoidal, squarewave or triangle waveform signals are suitable.

In the presently preferred exemplary embodiment a 30 kHz squarewave pulse train of 10 μsec. Width pulses is used. The carrier provides a constant current level on the order of 200 μa. A squarewave carrier modulation waveform is utilized to facilitate use of a phase synchronous demodulator, as will be explained.

As noted above, the transthoracic impedance varies in accordance with the respiration cycle. The transthoracic impedance includes a resistive component generally associated with pulmonary blood flow. The transthoracic impedance also includes a capacitive component generally associated with the changing capacitance of the thorax as the volumed mass ratio of the thorax changes during the respiration cycle.

The carrier signal is injected and the resultant voltage is sensed through electrodes electrically coupled to the patient's thorax. A bipolar (two electrode) configuration wherein the same set of electrodes both inject the carrier and sense the resultant voltage, or a tetrapolar (four electrode) configuration, using separate sets of electrodes for excitation and voltage sensing may be utilized.

The signal provided by impedance pneumograph comprises an AC information (respiration waveform) signal with a large DC offset. The resting impedance of the thorax (measured on a bipolar electrode configuration) is generally on the order of 400–1000 ohms at frequencies between 50 Hz and 1 MHz. The AC varying component of the impedance signal representing the respiratory cycle is generally between 0.2 ohms to 5 ohms. Thus, there is only on the order of 0.05% modulation. Breathing rates vary from on the order of six breaths a minute to on the order of 180 breaths a minute. Thus, the AC information component of the respiration signal is of relatively low frequency ranging from nearly DC.

In addition, the AC component of transthoracic impedance, includes a "cardiac component" artifact, attributable to the operation of the heart, rather than respiration. The cardiac component has a frequency in accordance with heart rate and normally has an amplitude equating to from approximately 0.02 ohms to 0.2 ohms.

The respiration signal from sensor 198 is applied to a preamplifier 200. Preamplifier 200 provides a high input impedance to the respiration sensor, and, in effect, DC couples the respiration sensor to the remainder of the monitor system. Preamp 200 operates both on the respiration impedance signal and the ECG signal. Preamp 200 demodulates the information signal from the carrier to develop a raw analog respiration waveform signal. Similarly, the ECG waveform signal is derived from the sensor output. Historically, respiration monitors have been AC coupled to the respiration sensor. A large capacitance (RC time constant on the order of 8 seconds) has been coupled across the monitor inputs to filter out DC offsets in the input signal. However, intelligence in the signal is often at frequencies as low as 0.1 Hz. Where the signal is AC coupled into the monitor, the frequency response of the monitor is typically −3 db at 0.5 Hz. Accordingly, the information components at low frequencies are greatly attenuated. When respiration rate decreases to, for example, 30 breaths per minute, the frequency response of conventional respiration monitors is such that only approximately 70% of the signal amplitude is sensed by the monitor. Thus, a 0.3 ohm transthoracic impedance would appear to be only 0.21 ohms to the detector. Similarly, when the respiratory rate falls to, for example, 15 breaths per minute, the response has fallen on the order of −6 db. Accordingly, the apparent transthoracic impedance registered by the monitor is only on the order of half the actual value. Thus, as the subject's respiratory rate decreases, the magnitude of the transthoracic impedance registered by the monitor steadily decreases. In addition, the frequency response of the prior art monitor tends to cause erroneous interpretation of the cardiac component of transthoracic impedance as the respiratory waveform. During apnea $P_{aCO_2}$ increases, (hypercapnea) causing a steady deceleration of heart rate from an initial value on the order of 140 beats per minute (approximate upper frequency $-6$ db point) to rates as low as 60 breaths per minute. By virtue of the frequency response of the system, the decreasing heart rate effects a two-fold increase in the registered magnitude of the cardiac component of transthoracic impedance. This phenomena is complemented by an actual increase of cardiac component amplitude resulting from the increase stroke volume of the heart at lower rates. The cardiac component thus drops into the frequency range normally associated with respiration and increases in amplitude to values as much as 0.2 ohms. In prior art AC coupled systems, a low pass filter ($-3$ db at 1.5 Hz) is generally used to discriminate against the cardiac component. However, during hypercapnic periods frequency discrimination becomes ineffectual and the cardiac component becomes indistinguishable from the respiratory component of transthoracic impedance. Accordingly, apneic episodes are often masked by erroneous detection of the cardiac component as the respiratory waveform. In fact, FDA regulations require all presently available impedance pneumograph sensor apnea monitors to include a warning to the effect that there is a possibility that the apparatus will monitor heart rate during severe apneic episodes. In addition, the respiration waveform is both time and amplitude distorted by the passband of the prior art systems. The typical passband of conventional respiration monitors peak at frequencies corresponding to 60 breaths per minute (having a nominal voltage equivalent to 1 ohm of transthoracic impedance). However, a wide range of respiration rates are exhibited by, for example, an infant (6 breaths per minute to 180 breaths per minute). It has been found that in most commercially available systems the electrical signal after coupling lags the actual respiration cycle by on the order of 30%–45% at 30 breaths per minute and undergoes a full phase reversal at on the order of 120 breaths per minute. DC coupling the respiration waveform to the monitor avoids distortion and phase shift in the respiration signal.

Preamp 200 also provides over voltage protection to guard the system against damage in the subject while respiration is being monitored. In the preferred exemplary embodiment, preamp 200 also includes provisions for common mode rejection, a preamplifier shield and a shield driver to eliminate radiated power line frequency signal problems. Preamp 200 will be described more fully in conjunction with FIG. 2.

The respiration waveform produced by preamplifier 200 is applied to a respiration analog processing circuit 300. Respiration analog processing circuit 300, provides waveshaping and DC offset compensation for the signal. Adaptive substraction of approximately 90% of the DC component in the respiration wavefrom signal is performed. It has been calculated from the human physiology that as much as 91.6% of the DC component of the respiration waveform could be substracted without entering into the range of values affected by the intelligence (AC) component. However, the DC base line very often drifts. Accordingly, an adaptive subtraction technique must be utilized. Respiration analog processing circuit 300 will be described in more detail in conjunction with FIG. 3.

The processed analog signal is applied to arithmetic processing circuitry 400. Arithmetic processing circuitry 400 includes a 16-bit analog-to-digital A/D converter, digital peak and slope detector 404 and a time domain rate discriminator 500. Peak detector 404 and time domain rate discriminator 500 operate as artifact rejection circuitry. The theory of operation is based upon knowledge of human physiology, to wit, limitations on the amount and rate of change of transthoracic impedance during the respiratory cycle and the relative timing of respiratory events. Digital peak and slope detector 404 provides signals indicative of inspiration and expiration states during the respiratory cycle. These signals may be utilized to provide audio/visual indicia of the subject's respiration. Changeovers between inspiratory and expiratory periods are indicative of maxima and minima in the respiratory cycle.

Digital peak and slope detector 404 is also, in effect, a digital filter, providing amplitude discrimination against changes in impedance not of sufficient magnitude to be associated with respiration. In particular, the resolution of the monitor with respect to respiration extrema is chosen to be 0.3 ohms. Impedance changes of less than 0.3 ohms are effectively filtered out by digital peak and slope detector 404 and a divide-by-2 counter. Assuming the electrodes to be properly positioned, the digital filtering successfully discriminates against cardiac components of the signal. The cardiac component is generally on the order of 0.1 ohm. In addition, the maximum rate of change of thoracic impedance (or respiration) has been empirically determined for various populations of subjects. Accordingly, digital peak and slope detector 404 also rejects impedance changes exceeding the maximum possible change during a sampling period. For an infant, the maximum respiration rate is 180 breaths per minute (equating to a respiration rate of 3 Hz). A 25 msec. sample period is chosen in accordance with Shannon sampling theorum. Accordingly, if the signal changes at a slew rate greater than 1 ohm per 25 second sample, the signal can not relate to physical respiration and accordingly, the system is reset.

Time domain discriminator circuit 500 is responsive to the minima and maxima signals from peak detector 404 and operates to inhibit the monitor with respect to signals not occurring within the known time constraints of human physiology. Digital peak and slope detector 404 and time domain discriminator circuitry 500 will hereinafter be more fully described in conjunction with FIGS. 4 and 5.

A time discriminated extrema signal is applied to a respiration tachometry circuit 600. Respiration tachometry circuit 600 computes the actual respiration rate of the subject. The respiration tachometry circuit 600 is used to selectively activate an audio visual alarm if the respiration rate drops below or exceeds preset limits, and further, drives displays indicating the average or instantaneous respiration rate. Respiration tachometry circuit 600 also provides artifact rejection by discriminating against respiration period counts differing from the just previously measured period by more than a predetermined amount. The predetermined amount can be fixed, or can be adaptive, based upon a predetermined percentage of the previous period.

Digital peak and slope detector 404, time domain discriminator 500 and respiration tachometry circuit 600 all provide input signals to an X-ray trigger circuit 700. X-ray trigger circuit 700 will be described in conjunction with FIG. 7. X-ray trigger circuit 700 triggers the X-ray machine slightly before a selected respiration extrema. X-ray trigger circuit 700 provides for triggering of an X-ray machine only at a predetermined point in the respiratory cycle during a valid respiration measurement. It is first determined that a steady state of respiration exists, and no alarm conditions are present. In addition, the changes in successive respiratory periods must be within acceptable limits. Physiologically, the human respiratory system can not change rate by more than a predetermined percentage, e.g., ±20%, from the preceding period. It has been determined that the percentage can be equated to a predetermined number of breaths per minute for various population groups, e.g., infants, children, adults, etc. For infants, it has been found that 20 breaths per minute is an effective upper limit on rate changes between breaths. Further, the amplitude variations must be within prescribed limits, i.e., within a prescribed percentage of the last measured respiration cycle or an equivalent maximum or minimum change. Lastly, the X-ray technician must maintain the trigger circuit in an armed state by maintaining a switch in a depressed condition. If all of these criteria are met, trigger circuit 700 detects the transthoracic impedance at a point in the respiration cycle corresponding to the desired specie of respiration extrema, adjusts the measured impedance by a predetermined account to provide lead time for the X-ray machine, then triggers the X-ray machine when the adjusted value of impedance is next sensed in the respiratory cycle. X-ray trigger circuit 700 thus provides for accurate triggering of the X-ray machine at a desired level of respiration. The accuracy of triggering, as a practical matter, reduces the total exposure necessary to provide good X-ray pictures. X-ray trigger circuit 700 is also designed to prevent the X-ray machine from taking more than one exposure without rearming. In addition, if a valid trigger point is not detected in five successive breaths, the arm cycle will terminate and rearming (i.e., again depressing the rearm button) necessitated. The ECG signal developed by preamp 200 is applied through suitable analog processing circuitry 800 to a cardiotachometer 900.

Heart rate tachometry circuit 900 is similar to respiration tachometer 600 and provides a signal indicative of heart rate. The heart rate signals utilized to drive an audio visual alarm when the heart rate exceeds or drops below respective maximum and minimum threshold values. A display of the heart rate is also provided.

Respiration monitor system 100 generates apnea alarms when any of the following circumstances are detected: (a) when an apneic period (time period between respective inspirations) exceeds a preset time period; (b) when a respiration period exceeds the preceding respiration period by a predetermined factor and a predetermined number of successive decreases are detected in the heart beat period (physiological apnea); and (c) if the respiration rate and heart rate detected are equal for more than one sample (indicative of erroneous detection of the cardiac component as respiratory waveform).

As previously mentioned, alarms indicative of improper respiration and heart rates are also provided. In addition, an apnea alarm is also generated if a predetermined number of successive heart beats are at rates less than 100 (for infants).

Monitoring system 100 includes a number of provisions for preventing false alarms, without denigrating the sensitivity of the system to physical apnea. Amplitude, slew rate and time domain discrimination based upon empirical determinations of maximum and minimum values of physical parameters are utilized. For example, in the analog processing circuit 300, any voltage change corresponding to a change greater than, for example, ±20 ohms from the instantaneous DC base line is rejected as not being associated with normal respiration, i.e., an artifact and the system reset. Similarly, digital peak and slope detector 404, in the capacity of a digital filter, rejects any amplitude changes corresponding to less than, e.g., 0.15 ohms. Similarly, slew rate discrimination is provided based on the premise that it is physically impossible for the respiration waveform to increase at greater than a predetermined maximum rate. Accordingly, changes in transthoracic impedance greater than, for example 1 ohm during the course of a sample period (e.g., 25 msec.) are rejected. Further, time domain discrimination relating to the relative timing of particular events during the course of the respiratory cycle is provided by time domain rate discriminator 500. Similarly, an upper limit on respiratory rate has also been empirically determined. Accordingly, an upper threshold for valid respiratory rate measurements is established in respiratory tachometry circuit 600.

In addition, provisions are made to prevent erroneous interpretation of the cardiac component as the respiration waveform. Respiration monitor 100 is DC coupled, that is, presents a perfectly flat frequency response with respect to low frequency respiration signals. Accordingly, the amplitude drop off evidenced in the prior art systems at low respiration rates does not occur in monitor 100. Further, the amplitude discrimination of digital peak and slope detector 404 effectively prevents mistaken identification of the cardiac component as the respiration waveform. Assuming the apparatus to be properly used and electrodes properly disposed on the subject, the cardiac component never reaches the 0.3 ohm sensitivity level of monitor 100 and, erroneous identification of the cardiac component as the respiratory waveform can not occur.

In addition, as a fail-safe, an apnea alarm is energized if the respiration and heart rates (as sensed by monitor 100) are equal for more than a predetermined number of sequential sample periods. The heart rate and respiration rate are physically asynchronous, and accordingly, in terms of statistical analysis should not track. Accordingly, if the sensed respiration rate and the cardiac rate appear to be equal, it is assumed that the cardiac component has been mistakenly identified as the respiration waveform. Such mistaken identity can occur not withstanding the amplitude discrimination for example, in the event that electrodes are improperly placed, resulting in an abnormally high cardiac component.

It should also be appreciated that DC coupling of monitor 100 to the respiratory sensor provides a faithful, substantially unphase-shifted respiration waveform, to facilitate accurate measurement of inspiration to expiration (I/E) ratios. The inspiration to expiration (I/E) ratio is a parameter desirable for adjustment of artificial ventilators for use on infants. Where the ventilator is adjusted to provide inspiration/expiration ratio not in accordance with the natural I/E ratio of the infant, the infant tends to fight or resist the ventilator. Monitor 100 determines an average I/E ratio for the subject used only with valid data and exclusing all statistically significant false information.

In addition, monitor 100 can readily be adapted to control the ventilator. The parameters of the subject's respiration cycle are determined during normal breathing periods by monitor 100. When the breathing significantly varies from those parameters, i.e., breathing becomes labored, the respirator is set up in a feedback loop with monitor 100 to rematch the normal respiration of the subject.

The respirator/respiration monitor control accommodates the problem of weaning the infant from a respiratory. The respirator can be programmed to turn off the respirator at intermittent periods, reactivating the respirator at the end of a predetermined period or in response to a particular physiological effect, such as decreasing heart rate.

Figure 2:
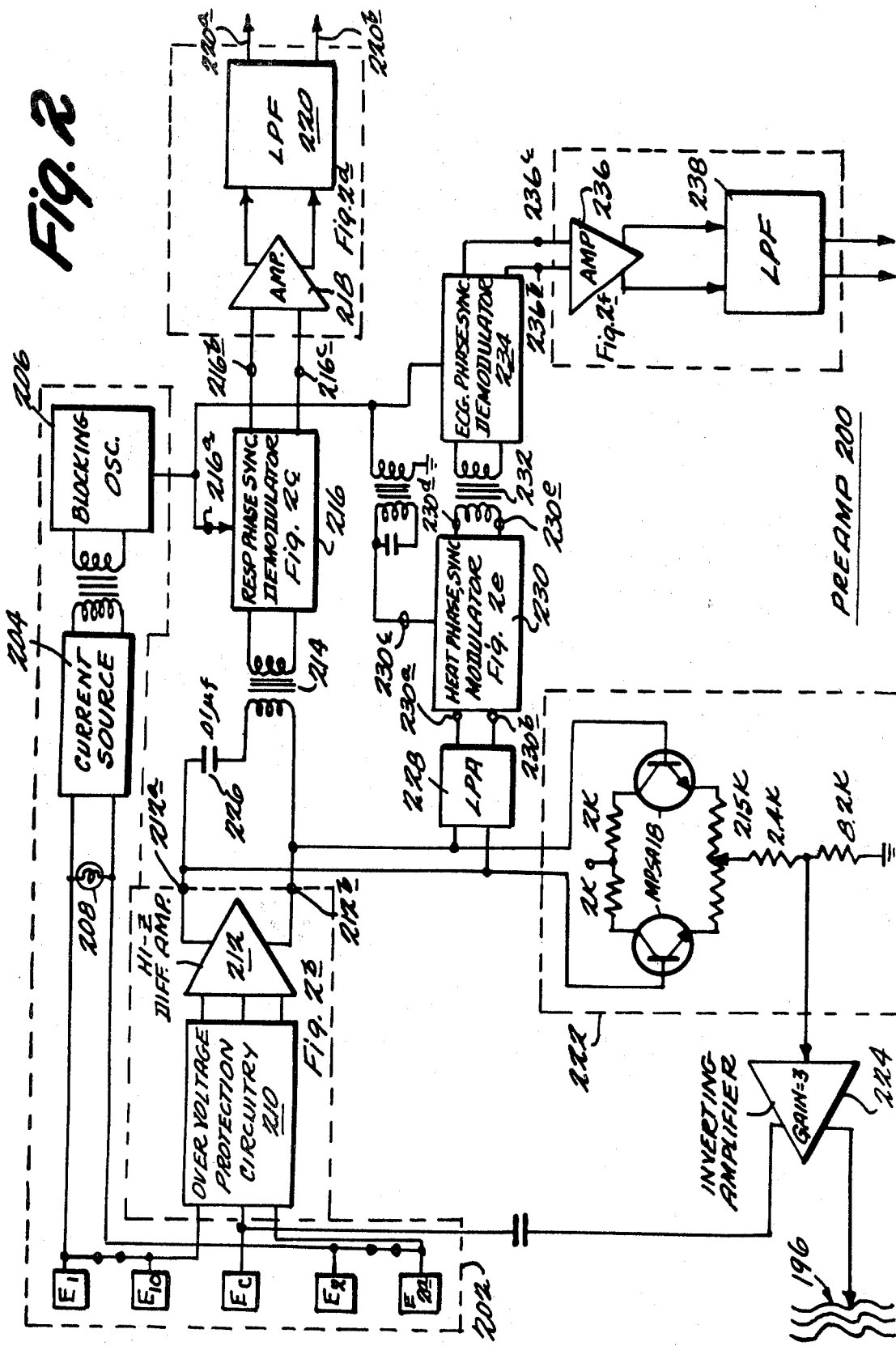
FIG. 2 is a block diagram of preamplifier 200.
Figure 2A:
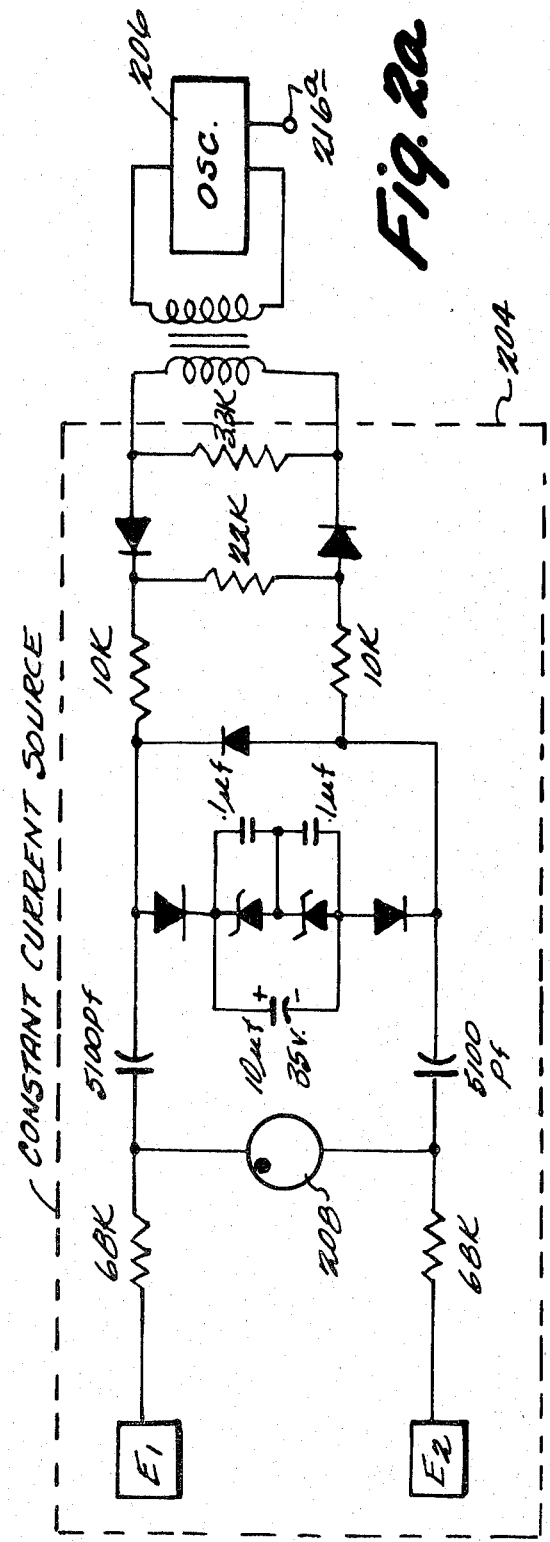
FIG. 2a is a schematic diagram of a suitable constant current source 204.

Referring now to FIG. 2, a more detailed description of a preferred preamplifier 200 will be provided. As previously noted in the preferred embodiment, respiration sensor 198 comprises an impedance pneumograph. A constant current pulse train is applied across the varying thoracic impedance to generate a voltage which varies in accordance with the transthoracic impedance. A set of electrodes 202 are disposed on the subject in a conventional bipolar or tetrapolar configuration. In a bipolar configuration, a set of electrodes, e.g., E1 and E2, are disposed on the mid-auxiliary lines over the sixth intercostal space. Electrode E1 is connected to one connector of a constant current source 204. Constant current source 204 is inductively coupled to an oscillator 206. Oscillator 206, in effect, on/off modulates current source 204 to provide a 300 kHz squarewave modulated signal of constant current pulses on the order of 200 $\mu a$ in amplitude and 125 $\mu sec$. pulse width. An exemplary current source 204 is shown in schematic form in FIG. 2a. The second electrode, e.g., E2 disposed on the opposite side of the thorax is connected to the other conductor of constant current source 204. A neon lamp 208 is coupled across the output lines of current source 204 to provide for over-voltage protection in the event of application of defibrillation signals to the subject. A third electrode, E3 is disposed on the subject, preferably equidistant to electrodes, to provide for detection of common mode signals.

Electrodes E1, E2 and EC are all coupled to suitable over-voltage protection circuitry 210. Over-voltage protection circuitry 210 is primarily to protect against damage to the monitor in the event of defibrillation procedures on the subject. The over-protection circuitry, in effect, couples electrodes E1 and E2 and the common reference electrode EC to the respective input terminals of a high input impedance differential amplifier 212. Suitable over-protection circuitry 210 and high input impedance amplifier 212 are shown in schematic form in FIG. 2b.

The output signal or differential amplifier 212, provided across output terminals 212a and 212b, comprises an on/off modulated constant current carrier (125 sec. pulses and duty cycle 30 Hz) amplitude modulated by the changing thoracic impedance. The output terminals 212 and 212a are coupled across the primary of an isolating transformer 214 (1:1).

The secondary of transformer 214 is coupled to a conventional phase synchronous demodulator 216. Demodulator 216 is also receptive of a signal indicative of the excitation carrier waveform from blocking oscillator 206. Phase synchronous demodulator 216, in effect operating as an homodyne demodulator, provides a demodulated output signal indicative of the respiratory waveform without any substantial phase shifting.

Figure 2C:
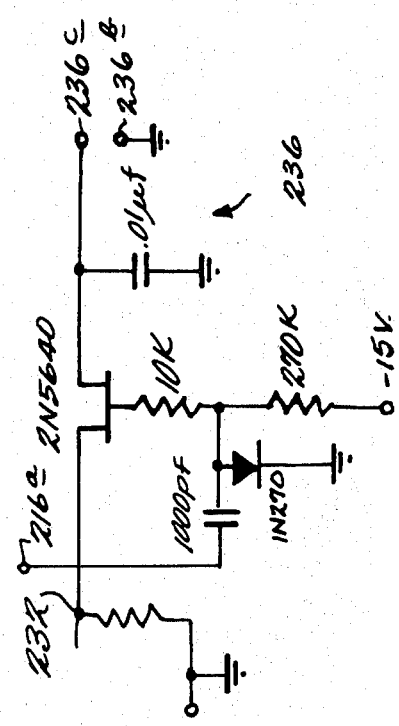
FIG. 2c is a schematic diagram of a suitable phase synchronous demodulator 216.

A suitable synchronous demodulator is shown in schematic form in FIG. 2c. In effect, demodulator 216 operates on the principle of turning an FET on and off in synchronism with the pulses of oscillator 206, storing a charge on a capacitor indicative of the peak value of the squarewave. The voltage across the capacitor is representative of the demodulated waveform without any significant phase shift.

The demodulated signal, generated across terminals 216b and 216c are applied to an amplifier 218 and low pass filter 220 to provide a differential analog singal to respiration analog processing circuit 300. Suitable amplifier 218 and low pass filter 220 are shown in schematic form in FIG. 2d. Amplifier 218 is adjusted to provide a sensitivity of 10 mV per ohm. Low pass filter 220 filters out high frequency transients in the demodulated waveform. At the frequencies associated with respiration, low pass filter 220 injects essentially no phase shift into the signal. The amplified, filter, demodulated signal is provided at ouput terminals 220a and 220b for application to respiration analog processing circuit 300.

Preamplifier 200 includes provisions for compensating for common mode signals (60 cycle noise). In effect, the common mode signals are measured and negatively fed back to the input of the preamp. The output terminals of amplifier 212 are coupled to a balanced differential amplifier 222, which provides an output singal equivalent to the common mode signal. The common mode signal is then inverted by an inverting amplifier 224 and capacitively coupled to reference electrode EC. Negative feedback is thus established to cancel common mode signals.

To further eliminate any outside electromagnetic interference in monitor 100, monitor 100 is encased in a three layer driven shield schematically illustrated and denoted in FIG. 2 as 196. Shield 196 suitably comprises an internal shield of 0.015 hydrogen annealed 2680 premalloy. The common mode voltage is applied to the internal shield as a driving signal. An intershield of $\frac{1}{8}''$ teflon or equivalent high di-electric material and an outer layer of fine mesh copper screen tied to earth are also utilized. It has been found that driven shielding 196 substantially eliminates electromagnetic interference with monitor 100.

ECG signals are also derived from the output of amplifier 212. The ECG is a biopotential present on the subject's body. The ECG signals generally comprises voltage having frequency components ranging from DC to on the order of 100 Hz. The ECG signals are blocked from respiration demodulator 216 by 0.1 $\mu f$ blocking capacitor 226, interjected between one lead of the primary of transformer 214 and output terminal 212a of differential amplifier 212. Capacitor 226 and the primary of transformer 214 cooperate as a high pass filter, blocking frequencies above the order of 100 cycles. The output terminals of amplifier 212 are connected to a low pass filter 228. Low pass filter 228 suitably comprises a pie-section filter comprising a 10 mH inductor and 0.1 $\mu f$ capacitor. The output of low pass filter 228 is taken across the capacitor. Low pass filter 228, in effect, filters out the carrier components of the signal and generates a slowly timed variant DC voltage having a frequency content ranging from zero to on the order of 100 Hz.

It is desirable that the patient be electrically isolated from power ground to prevent electrical shock and for greater common mode rejection at power line frequencies. However, the output of low pass filter 228 is a very slowly varying signal not generally compatible with passage through a transformer. Accordingly, the ECG signal is, in effect, chopped by a phase synchronous modulator 230, driven by a signal derived from blocking oscillator 206. Thus, the output of modulator 230 is essentially the low frequency (DC) output signal of low pass filter 228 chopped at a rate synchronous with blocking oscillator 206. A suitable phase synchronous modulator is shown in schematic form in FIG. 2e. The chopped signal is applied across transformer 232 to a phase synchronous demodulator 234, similar to phase synchronous demodulator 216.

Ringing between modulator 230 and demodulator 234 is prevented by utilizing field effect transistors having different threshold voltages, e.g., 2N5654 FET's having a pinch-off of −8 volts are utilized in modulator 230 and on FET-type 2N5664 (having a pinch-off voltage of −6 volts) is utilized in demodulator 234. By appropriate choice of relative pinch-off voltages demodulation is effected during relatively noise free (transient) periods in the output signal of modulator 230.

Figure 2F:
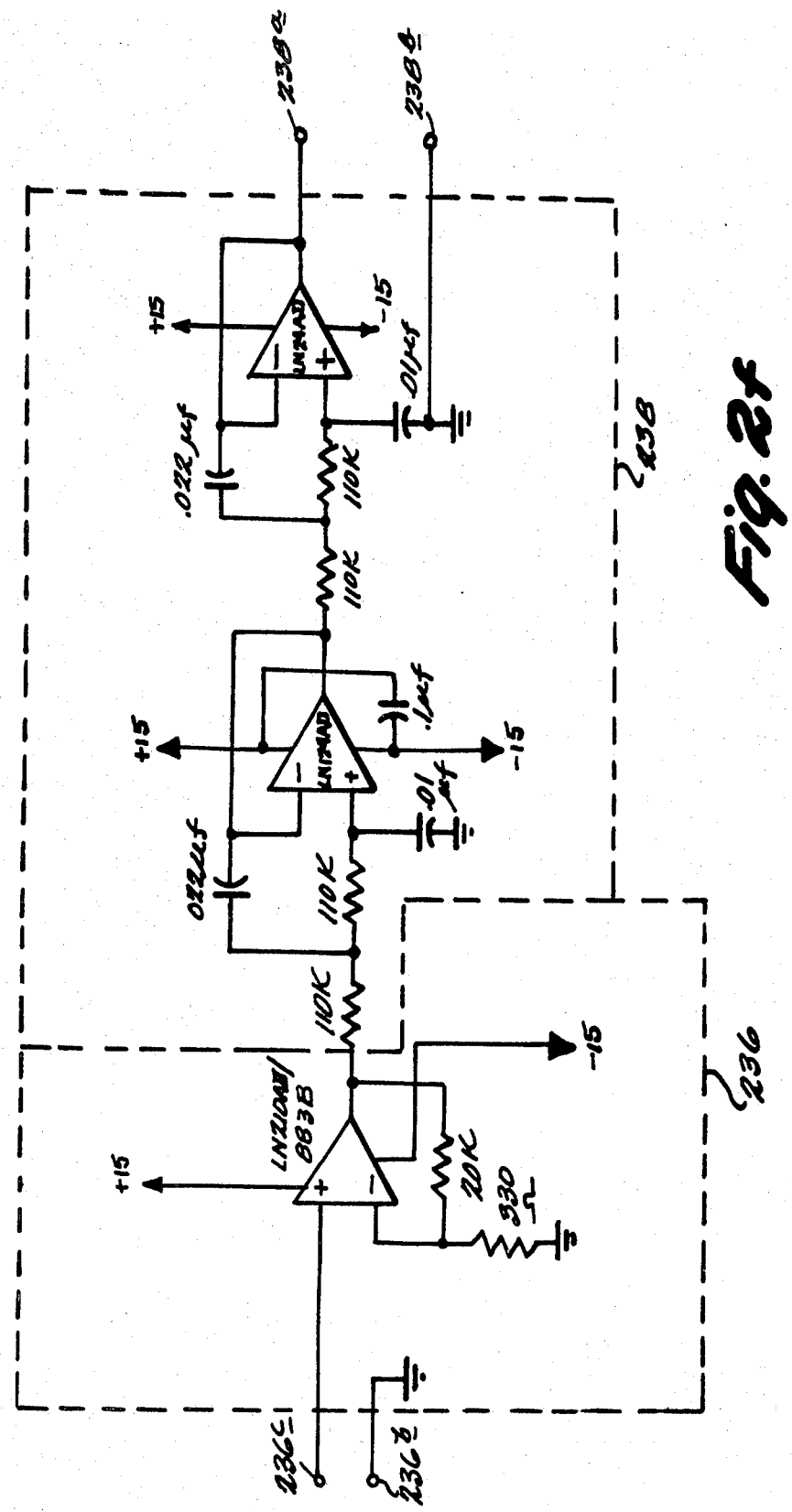
FIG. 2f is a schematic diagram of a suitable amplifier 236 and low pass filter 238.

The output of the ECG demodulator 234 is applied to a suitable amplifier 236 and a low pass filter 238. Amplifiers 236 and 238 are shown in schematic form in FIG. 2f. The frequency response of filter 238 is essentially flat with respect to frequencies from DC to 100 Hz, the −3 db point being at 100 Hz. When the frequency is above 500 Hz, the response rolls off at 80 db per decade. The frequency response may be generally categorized as a Butterworth flat frequency response. While some phase shifting is effected by the filter, the shifting does not significantly effect the geometry of the ECG waveform. It should be appreciated that the common mode rejection scheme, driven shield and high isolation impedance described above, provide for generation of an ECG waveform without requiring 60 cycle filtering. Accordingly, the output signal from low pass filter 230 is of diagnostic quality.

The respiration waveform provided across outputs 220a and 220b of low pass filter 220 is applied to respiration analog processing circuit 300. Respiration analog processing circuit 300 provides signal conditioning, adaptive subtraction of a predetermined percentage (e.g., 90%) of the DC offset level and indicia of the relative quality of electrode connection. The signals from preamp LPF 220 are applied to a variable gain differential amplifier 302. The single ended output of amplifier 302, provided at output terminal 302a, is connected to an inverting amplifier 304 and to one leg of a summing circuit 306, as will be explained. Variable gain differential amplifier 302 standardizes and linearizes the sensitivity response of monitor 100. Sensitivity is adjusted to exactly 10 mV per ohm, with 1 V equivalent to 100 ohms and 10 V corresponding to 1000 ohms transthoracic impedance. Variable gain differential amplifier 302 and inverting amplifier 304 are together shown in schematic form in FIG. 3c. Linearity and temperature stability of response are ensured through use of military grade LH2101AD/833B monolithic operational amplifiers.

The output (raw analog) of inverting amplifier 304 (provided at 304a) is analyzed with respect to impedance level to determine the relative quality of the electrode connections to the subject. The raw analog signal at terminal 304a is applied to a plurality of comparators 308–311. The other inputs to comparators 308–311 are receptive of respective voltages corresponding to predetermined impedances. For example, comparator 308 has applied a 10 V reference corresponding to a measured transthoracic impedance of 1000 ohms. Comparators 309 and 310 operate with reference voltages corresponding to, for example, 700 ohms and 400 ohms transthoracic impedance, respectively. Comparator 311 operates with reference voltage corresponding to just under 100 ohms (e.g., 0.98 V), the low end of acceptable transthoracic impedance values. The respective outputs a–d of comparators 308–311 are applied to a conventional decoder 312, which selectively drives indicator lamps corresponding to quantitized electrode connection ratings. Under normal operating conditions the minimum thoracic impedance encountered is on the order of 100 ohms. Accordingly, where the respiration waveform indicates a thoracic impedance of less than 100 ohms, a malfunction exists. For example, the electrodes may be shorted together. Similarly, where transthoracic impedances over 1000 ohms are encountered, an improper electrode connection to the subject or a system malfunction exists. A truth table for decoder 312 is provided in Table 1.

TABLE I

| Z>1000 A | Z>700 B | Z>400 C | Z>100 C | Indicator |
|---|---|---|---|---|
| 0 | 0 | 0 | 0 | Low Z, bad electrode connection |
| 0 | 0 | 0 | 1 | Excellent electrode connection |
| 0 | 0 | 1 | 1 | Good electrode connection |
| 0 | 1 | 1 | 1 | Fair electrode connection |
| 1 | 1 | 1 | 1 | High Z, bad electrode connection |

It should be appreciated that the indication of the relative quality of electrode contact is also an indication of the validity of the data. In addition, the output of comparator 308 (indicative of transthoracic impedance greater than 1000) and the inverted output of comparator 311 (the inverted output being indicative of transthoracic impedances of less than 100) are applied to an OR gate 314. The output of OR gate 314 may be termed the Z out-of-limits signal.

The Z out-of-limits signal is applied to a master clear one-shot 316, which generates a negative going pulse output signal to reset the system in the event of an impedance measurement out of physiological limits. Master one-shot 316 is also triggered upon powering up of the system by suitable circuitry 318 to initiate the system. Power-on clear circuitry 318 suitably comprises a RC timing circuit which provides a high level signal through OR gate 314 to master clear one-shot 316 until the capacitor in the circuit charges after a predetermined period whereupon the output assumes a low level. Master clear 316a synchronizes the respective system components upon powering up and resets the respective contents upon an indication of an out-of-limits impedance.

As noted above, respiration analog processing circuitry 300 compensates for DC offset. In effect, 90% of the DC voltage (a percentage determined not to impinge upon any information signal) is subtracted from the raw analog signal. The raw respiratory analog signal provided at terminal 304a is applied to a voltage divider 316. Voltage divider 316 is adjusted to provide an output signal equal to 0.9 (90%) of the applied input signal. The 90% signal from voltage divider 316 is applied through a low pass filter 318 to a voltage follower buffer amplifier 320. Low pass filter 318 filters out any high frequency noise transients. Voltage follower 320 operates as a buffer and provides a greater current capability. Exemplary circuitry for voltage divider 316, low pass filter 318 and buffer amplifier 320 is shown in schematic form in FIG. 3d. Buffer amplifier 320 is of linear response with no DC offsets. To this end, in the preferred embodiment, a military grade LH2101AD/8838 operational amplifier is utilized.

Figure 3A:
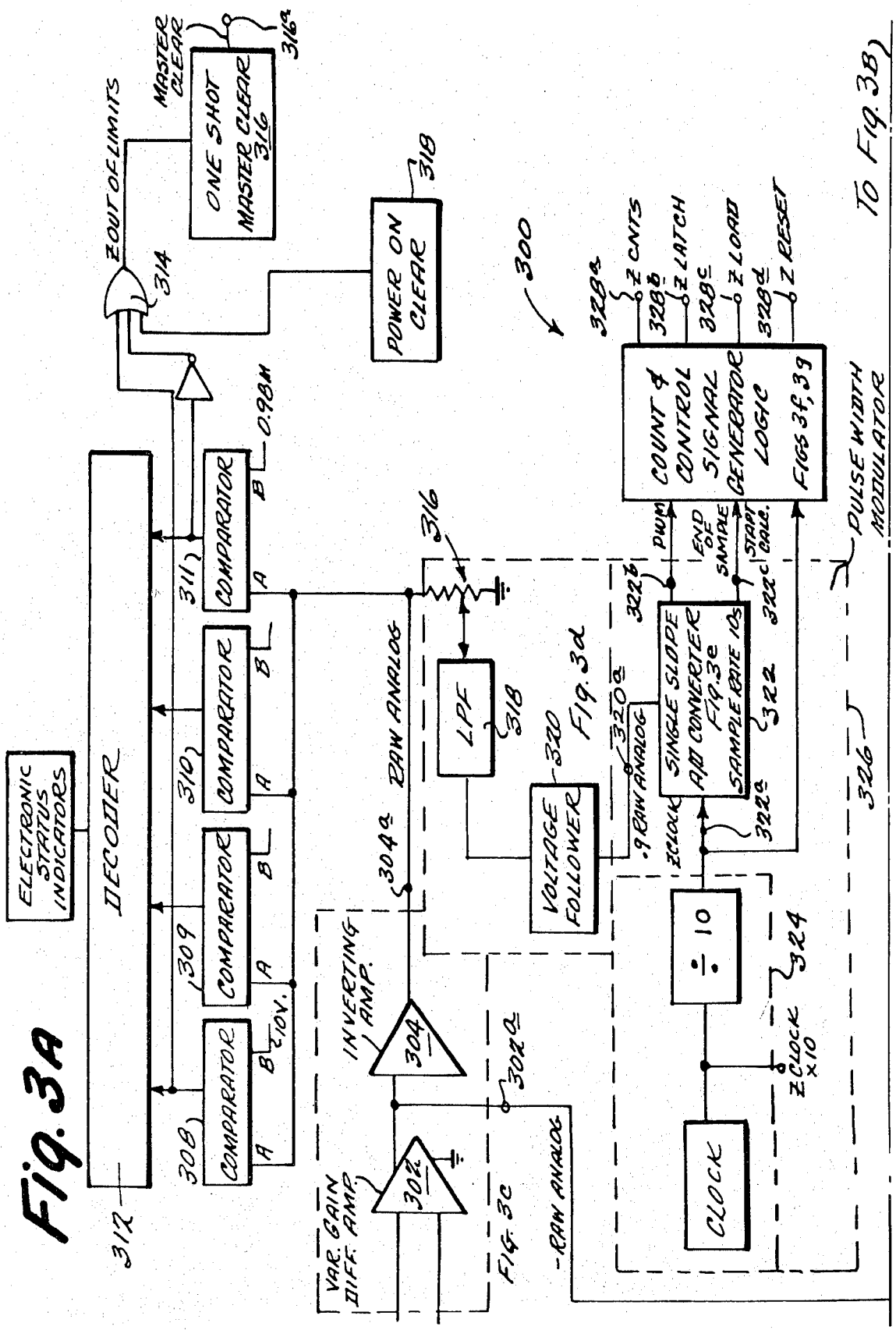
FIGS. 3a and 3b are block diagrams of respiration analog processing circuitry 300.
Figure 3B:
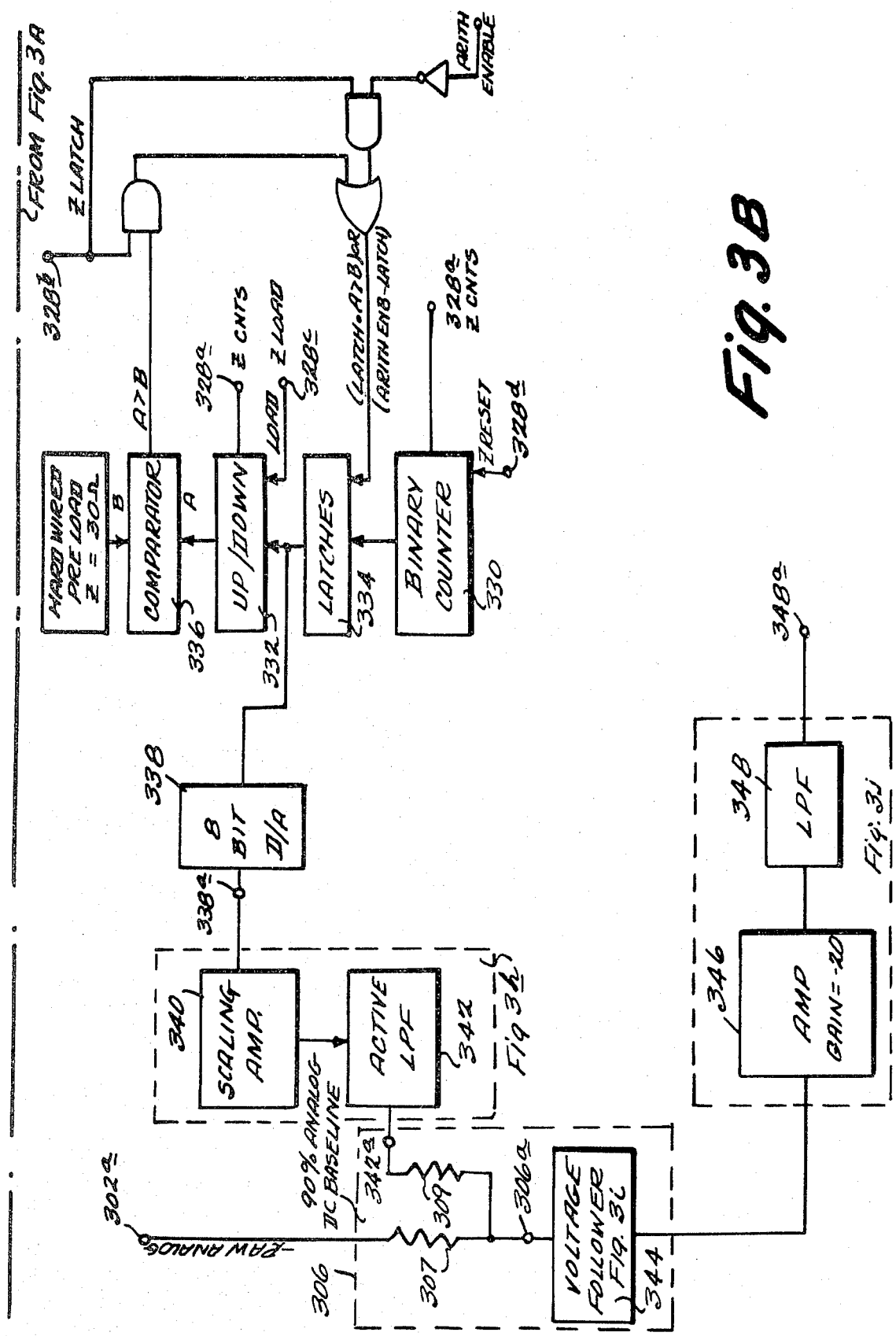
Figure 3C:
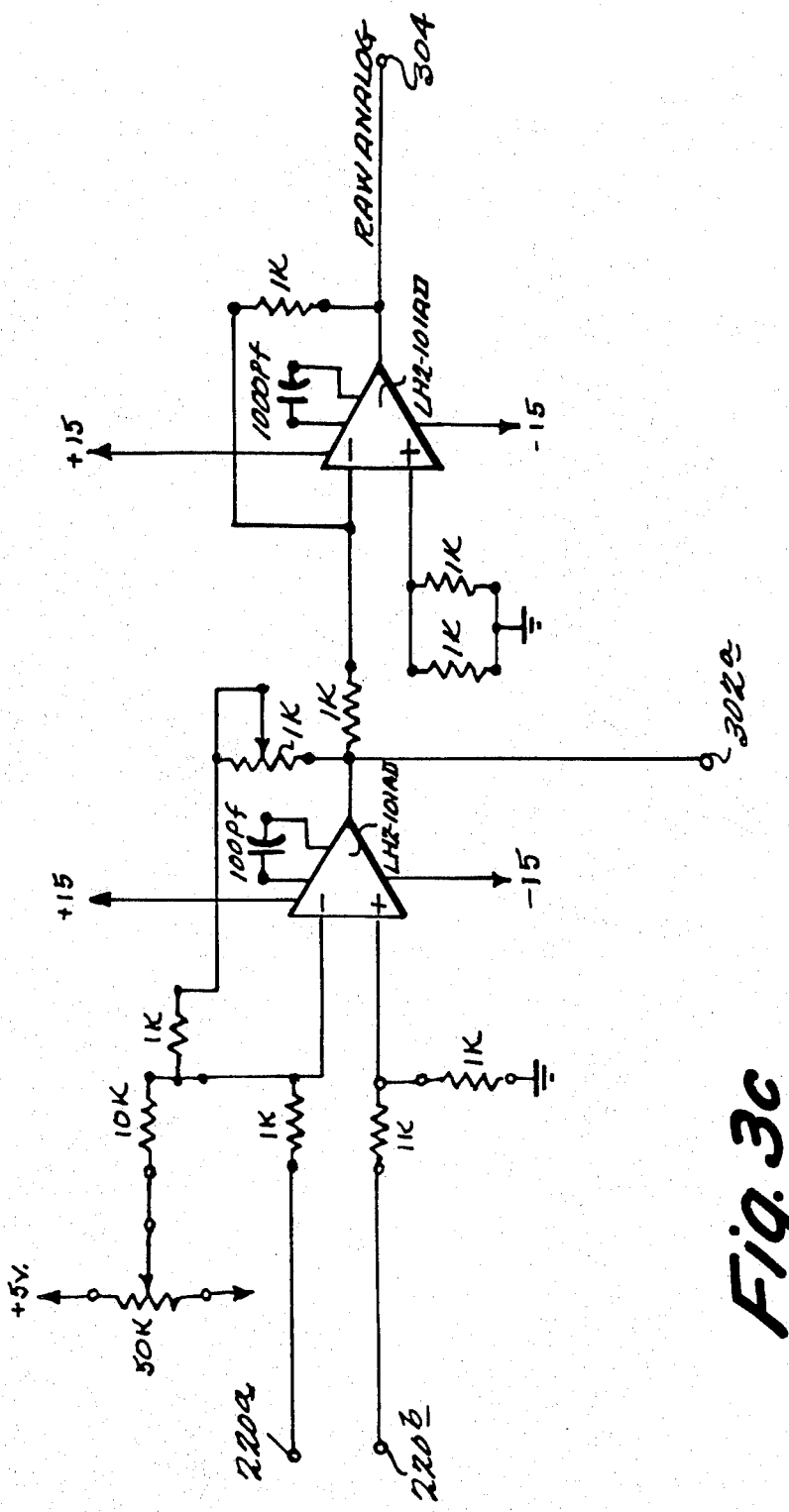
FIG. 3c is a schematic diagram of suitable amplifier 302 and 304.
Figure 3D:
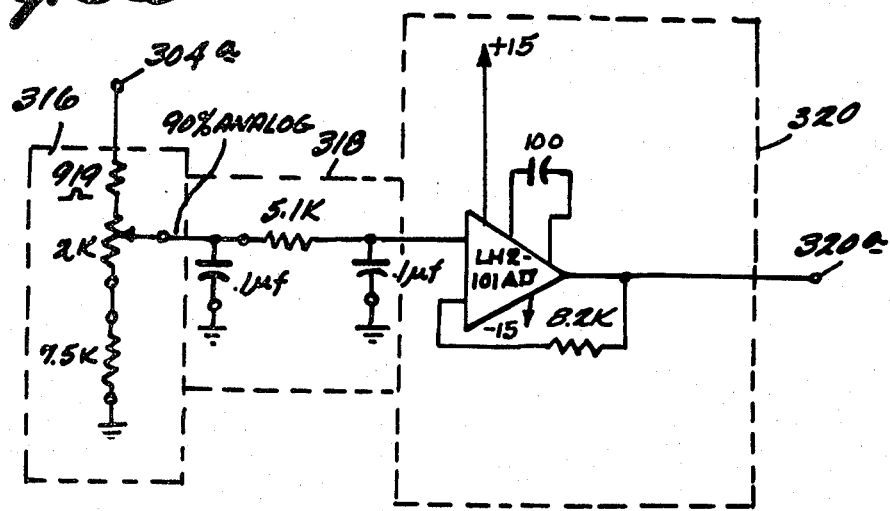
FIG. 3d is a schematic diagram of suitable voltage divider 316, low pass filter 318 and voltage follower 320.
Figure 3E:
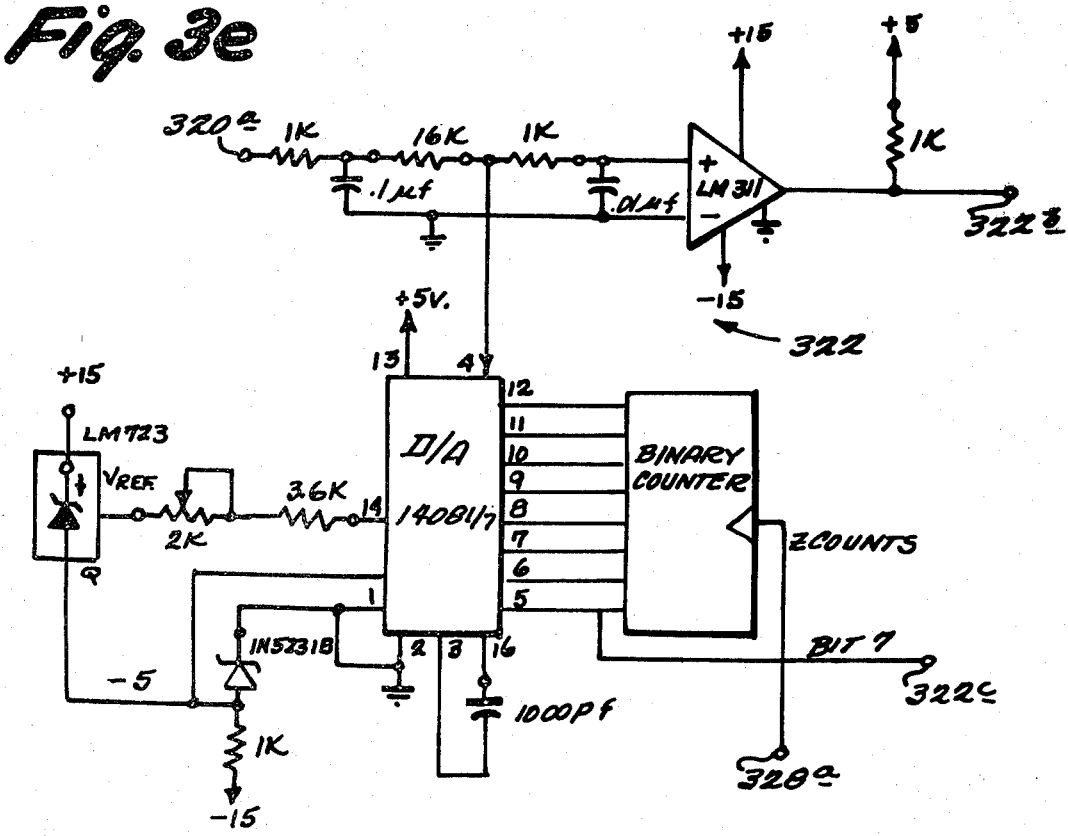
FIG. 3e is a schematic diagram of suitable A/D converter 322.

The output of buffer amplifier 320 provided at output terminal 320a is applied to a single slope A/D converter 322. A/D converter 322 generates a pulse width modulated output signal indicative of the amplitude of the 90% signal. In effect, A/D converter 322 compares a digitally generated linear ramp signal to the 90% signal, and generates a pulse having a first transition at the beginning of the sample period and a second transition when the ramp voltage equals the sample. The sample rate is chosen to be once every 10 seconds. The digital slope generator is driven by a clock signal developed from a free running oscillator and divider 324. An exemplary A/D converter 322 is shown in FIG. 3e.

Clock 324 and single slope A/D converter 322 together operate as a pulse width modulator 326 providing a pulse width modulated signal and a signal indicative of the end of the 10 second sampling period.

Figure 3F:
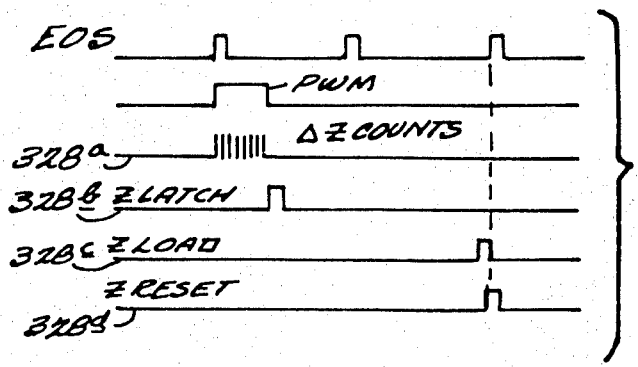
FIGS. 3f and 3g are timing diagrams, and schematic diagrams of a suitable control signal generator logic 328.
Figure 3G:
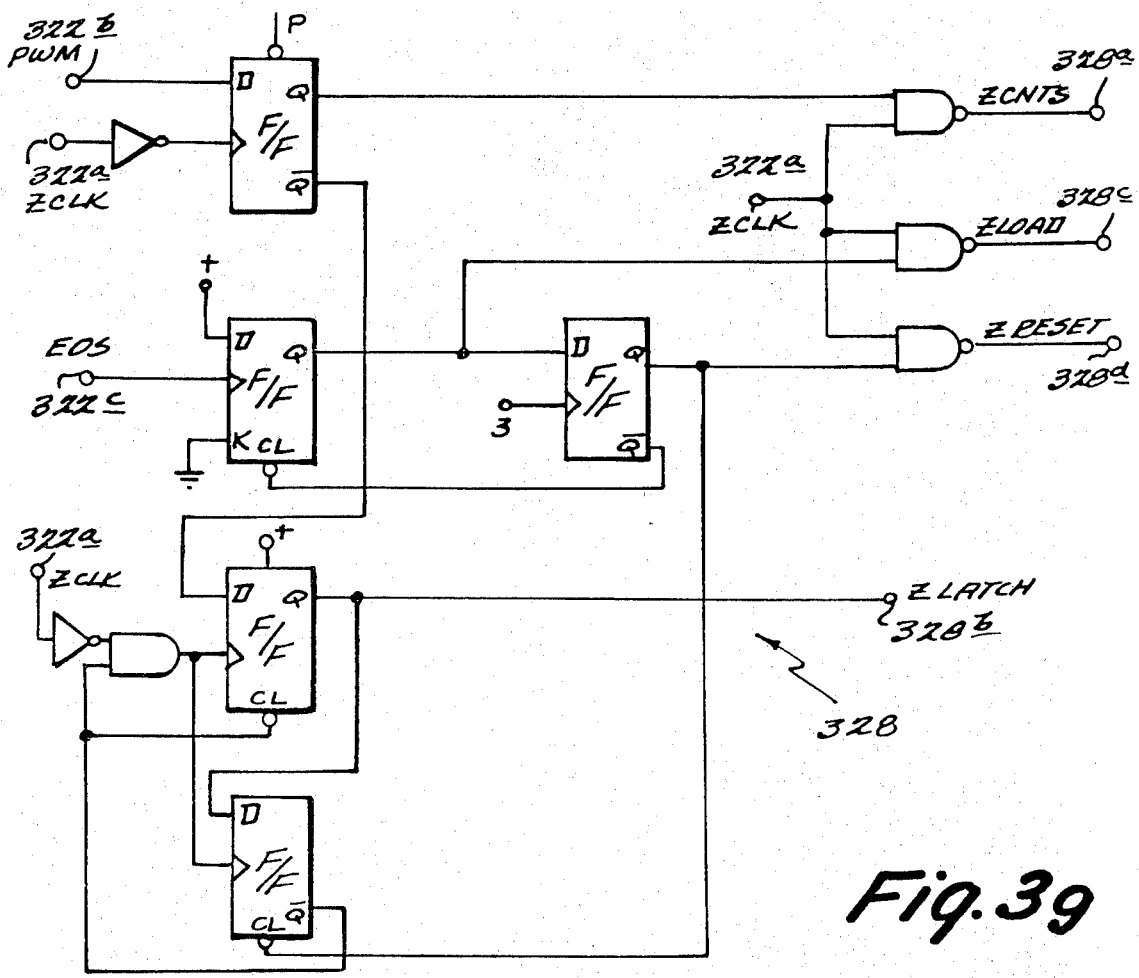
Figure 3H:
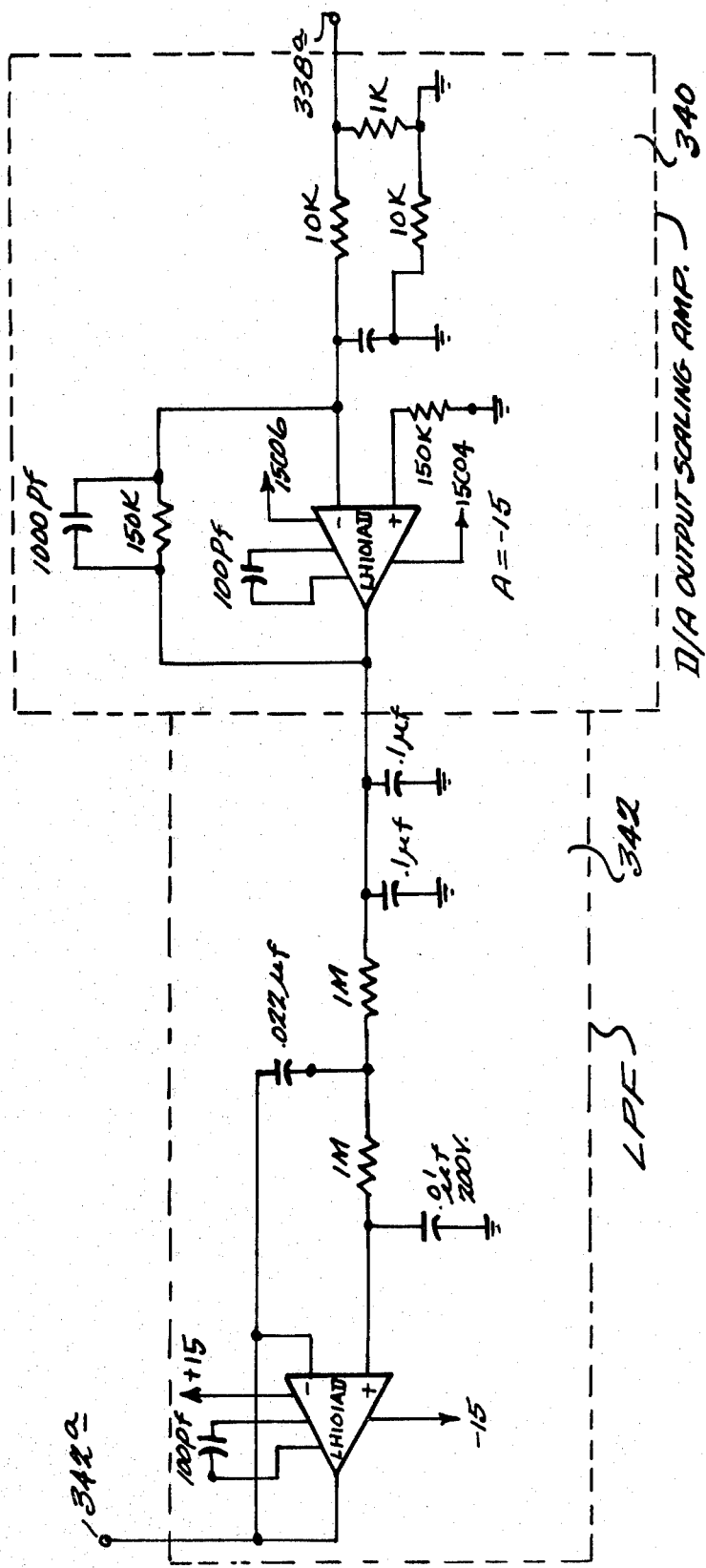
FIG. 3h is a schematic diagram of suitable scaling amp 340 and filter 342.
Figure 4A:
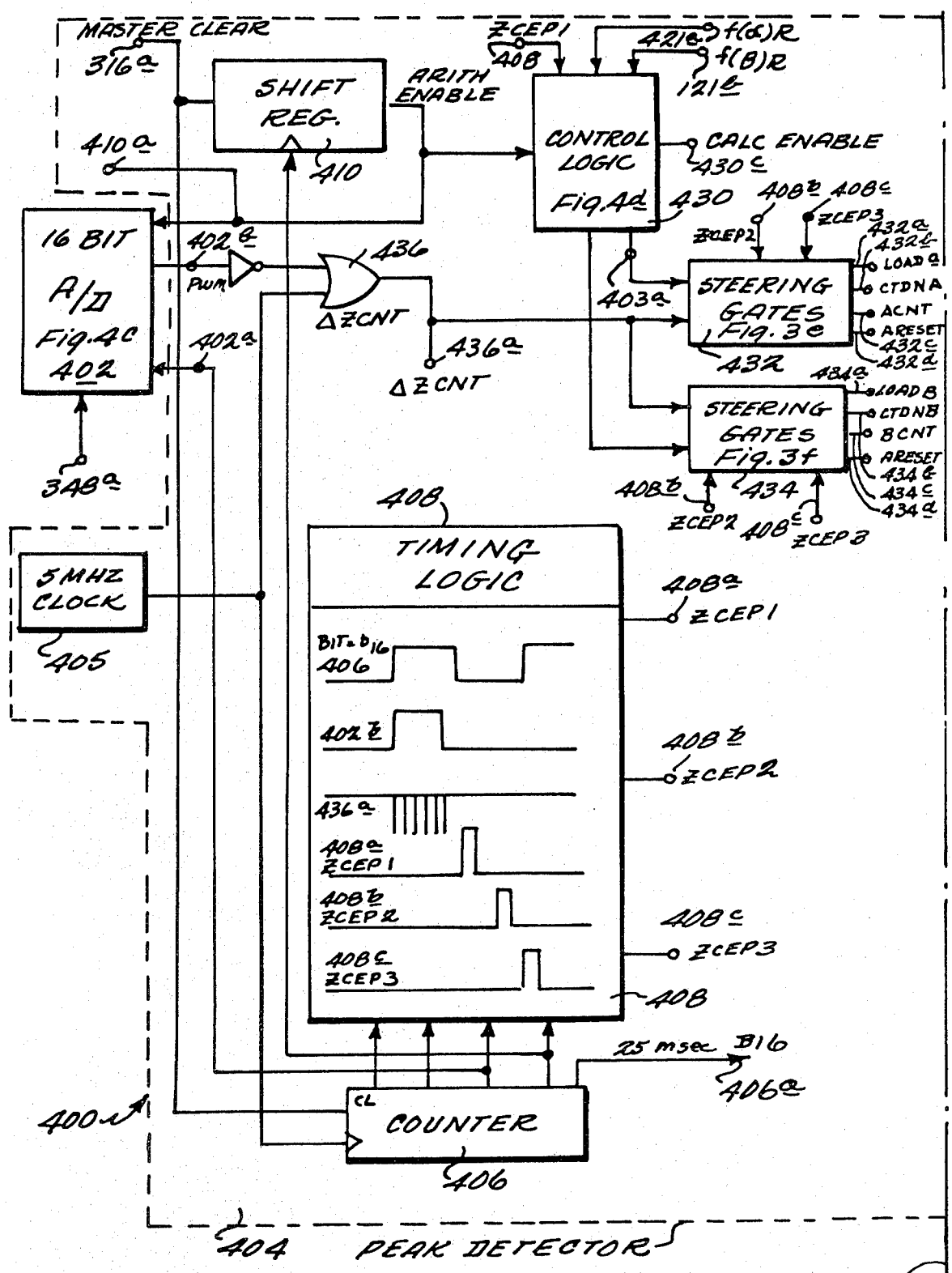
FIGS. 4a and 4b are a block diagram of digital peak and slope detector 404.
Figure 4B:
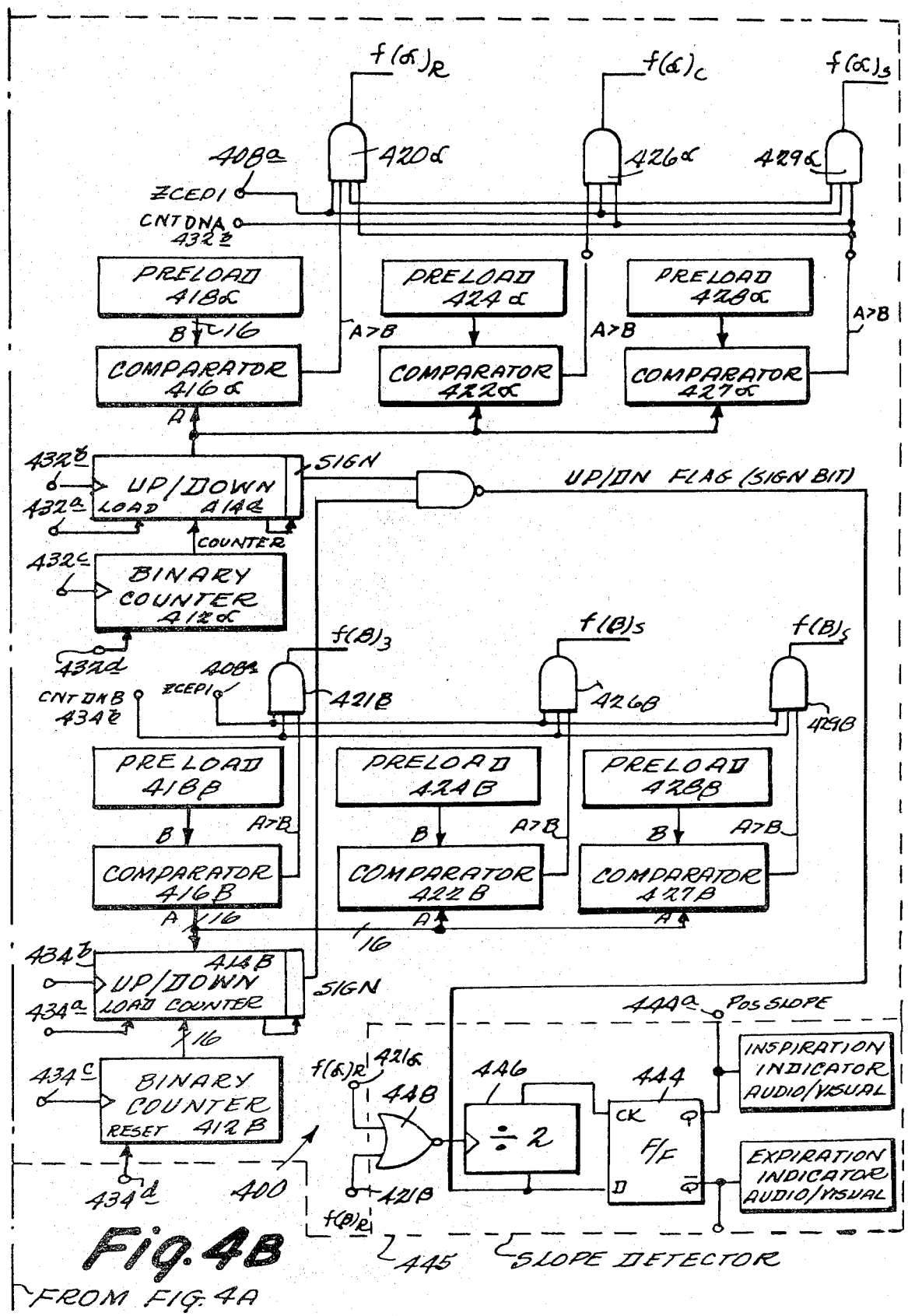
Figure 4C:
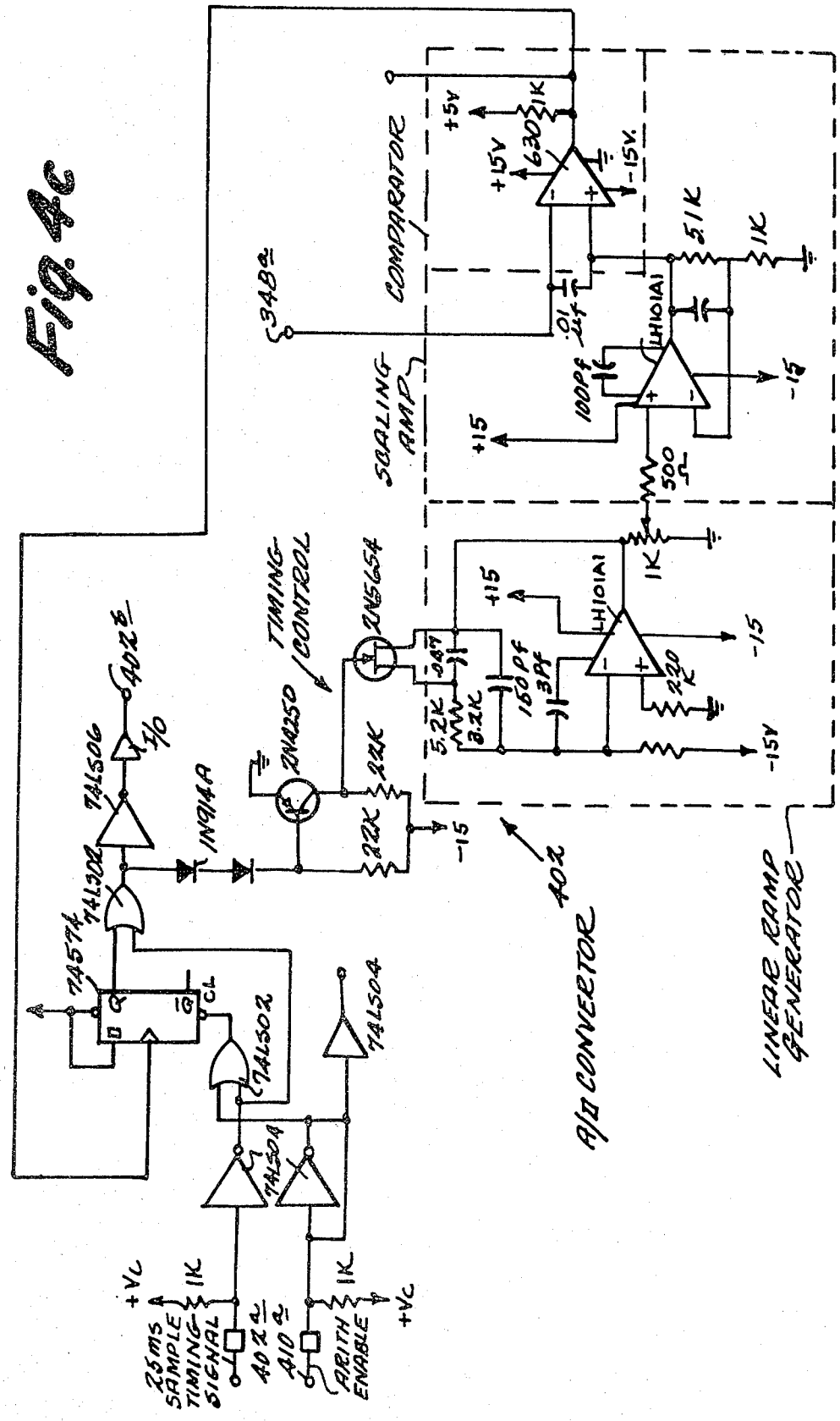
FIG. 4c is a schematic diagram of suitable A/D converter 402.
Figure 4D:
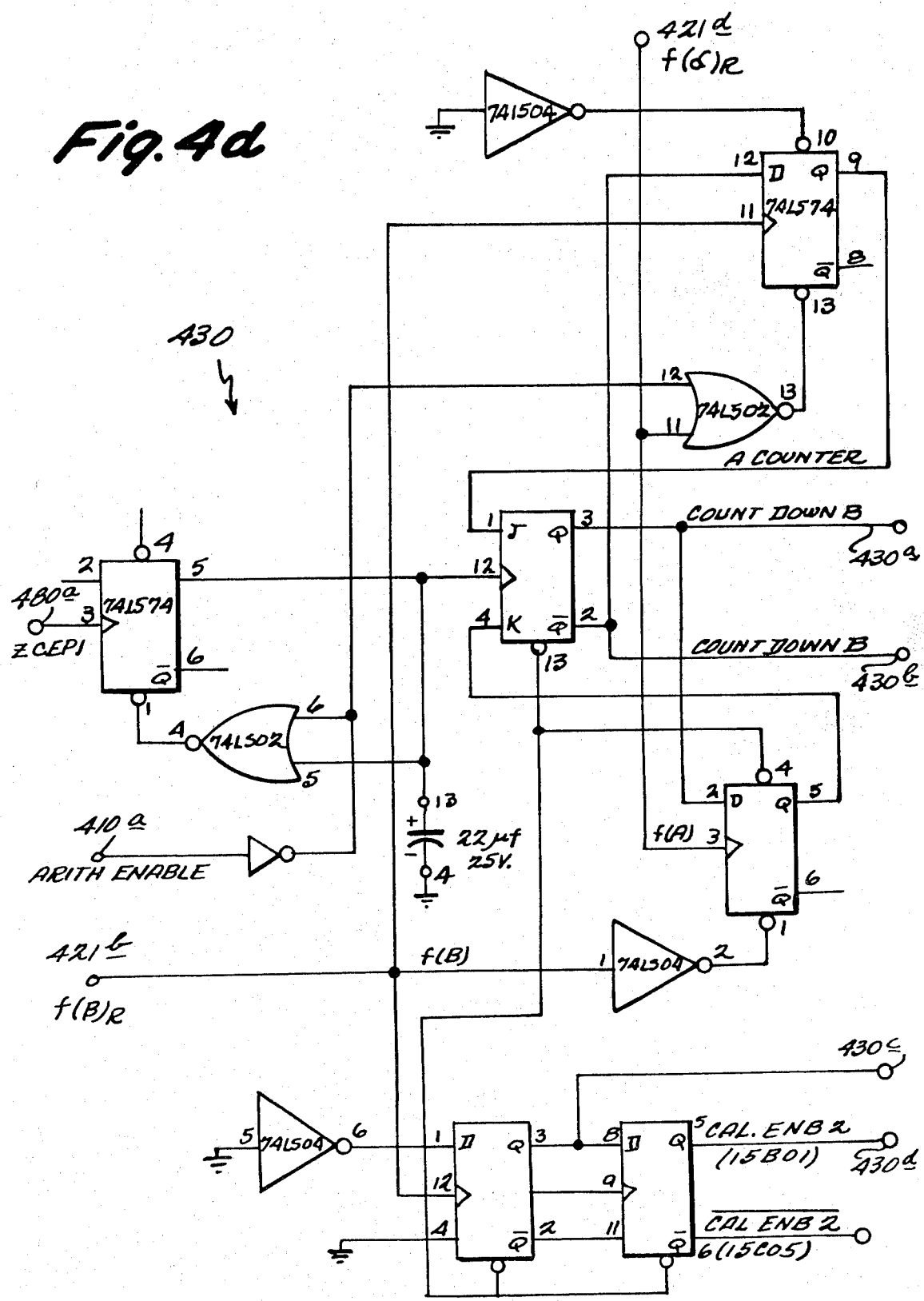
FIG. 4d is a schematic diagram of a suitable control logic 430.
Figure 4E:
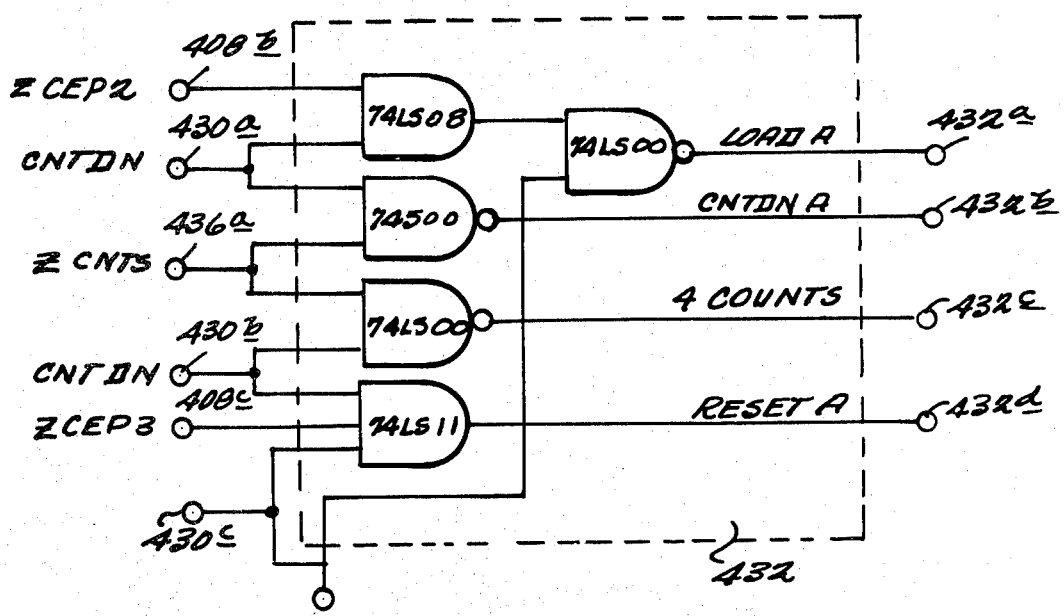
FIGS. 4e and 4f are schematic diagram of suitable steering gates 432 and 434.
Figure 4F:
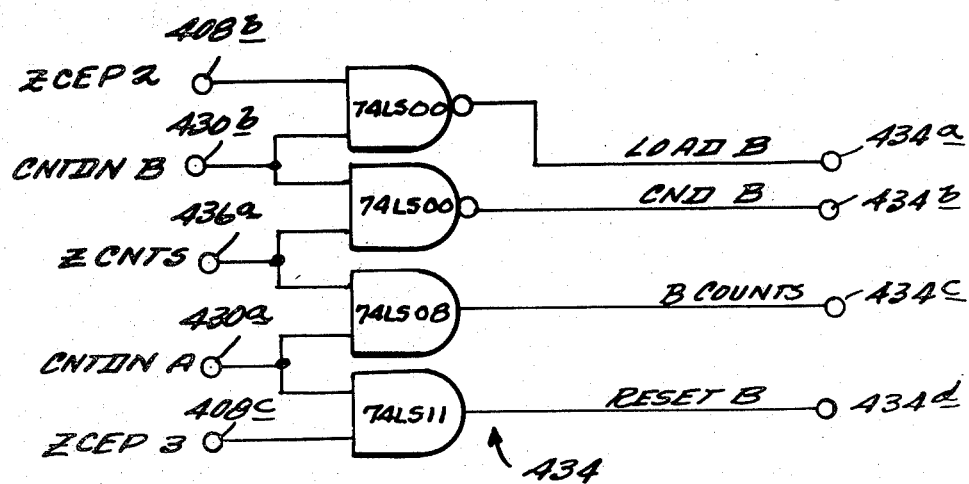

The pulse width modulated signal, provided at output 322b, the end of sample signal, provided at terminal 322c and the Z clock signal, provided at terminal 322a, are applied to suitable count and control logic 328. Logic 328 generates, at respective output terminals 328a, 328b, 328c and 328d, respective signals designated Zcount, Zlatch, Zload, and Zreset. These signals are illustrated in FIG. 3f. Briefly, the clock signals from terminal 322a are gated during the duration of the pulse width modulated signal provided at terminal 322b, to produce the Zcount signal at terminal 328a. Zlatch, Zload, and Zreset are sequential signals generated in timed relation with the operational cycle of respiration analog processing circuit 300. Suitable logic for 328 is shown in FIG. 3g.

The Z counts provided at terminal 328a increment a binary counter 330. The Z counts are also applied as clock signals to an up/down counter 332. Up/down counter 332 and binary counter 330 are connected in parallel through a register of latches 334, as will hereinafter be explained. Latches 334 are used to store a count representative of the DC base line for the respiration waveform. Latches 334 are selectively loaded with the binary count when the 90% count of a particular sample differs from the previous base line count by a predetermined amount. More particularly, the parallel outputs of up/down counter 332 are applied as one set of inputs to a magnitude comparator 336. The other set of inputs of comparator 336 are hardwired to correspond to a predetermined value in accordance with the maximum excursion of information. For example, the thoracic impedance doesn't generally change by more than ±5 ohms. Accordingly, a value equivalent to an impedance of 10 ohms can be utilized as the threshold value. In the preferred embodiment, a value equivalent to 30 ohms is utilized to prevent resetting of the system by spurious noise. At the end of the pulse width modulated signal a count has been accumulated in binary counter 330 indicative of the 90% analog value. Latches 334 are initially loaded with the contents of binary counter 330 in response to the next Zlatch signal from logic 328 in coincidence with an arithmetic enable signal generated, as will be explained, by arithmetic processing circuitry 400 in predetermined timed relation with the master clear one-shot pulse from one-shot 316. Thereafter, in response to the Zload signal, up/down counter 332 is loaded with the contents of latches 334. As previously noted, the contents of latches 334 represent the 90% level at sample time. Binary counter 330 is thereafter reset in response to the reset signal from logic 328. During the next sampling period, binary counter 330 is incremented and up/down counter 332 is decremented in response to the Z counts. At the end of the accumulation period, the count in up/down counter 332 is indicative of the magnitude of the difference between the previous count, i.e., the 90% base line, and the instantaneous sample. Accordingly, if the difference exceeds the predetermined threshold, the instantaneous sample is then loaded in response to the Zlatch control signal into latches 334 to update the DC base line, and a pulse is applied through OR gate 314 to trigger master clear one-shot 316 and reset the system. If the difference between the sample and base line count does not exceed the predetermined threshold, it is assumed that the difference is attributable to information and the 90% DC base line in latches 334 maintained. Thus, the contents of latches 334 are indicative of the sampled 90% level.

The contents of latches 334 are also reconverted into an analog signal by an 8-bit D/A converter 338. The analog signal is applied through a suitable scaling amplifier 340 and active low pass filter 342 to the second leg of summing junction 306. Scaling amplifier 340 restores the output signal from D/A converter 338 to the 90% analog level. Scaling amplifier 340 is suitably an operational amplifier having a high input impedance. Filter 342 blocks any switching transients in the output signal of D/A converter 338. An exemplary scaling amplifier 340 and active low pass filter 342 are shown in schematic form in FIG. 3h.

Summing circuit 306, adds the 90% DC base line and the raw analog signal from terminal 302a. Summing junction 306 is formed by precision metal film resistors 207 and 309. Summing junction 306a is coupled to a voltage follower buffer amplifier 344. A suitable buffer amplifier 344 is shown in FIG. 3i.

The output of voltage follower 344 is applied to an inverting amplifier 346, having a gain of −20. Inverting amplifier 346 provides an output signal of proper polarity. Amplifier 346 is connected to a low pass filter 348 to further reject any transients in the signal, without providing any appreciable phase shifting of intelligence. A suitable inverting amplifier 346 and low pass filter 348 are shown in schematic form in FIG. 3j.

The output of low pass filter 348a represents the raw analog signal minus 90% of the sampled DC signal level. More particularly, the signal represents the instantaneous signal $(ac_i + dc_i)$ minus 90% of the signal $(Ac + Dc)$ at sample time divided by two, times the gain of amplifier 346. Assuming the AC component to be negligible with respect to the DC component at sample time, it is found that the signal is approximately equal to ten times the AC component (information) plus the DC component. Thus, the intelligence to DC offset radio is increased by a factor of 10. The output of analog processing circuit 300 provided at terminal 348a will hereinafter be referred to as the 1% analog signal.

It is significant that the entire circuit is DC coupled and that very little phase shifting is effected on the signal. The frequency response of all of the low pass filters were chosen to have virtually no effect on the AC intelligence signals.

The output of analog processing circuitry 300 provided at output terminal 348a is applied to arithmetic processing circuitry 400. Arithmetic processing circuitry 400 develops signals indicative of the occurrence of respiration extrema, and performs, amplitude, slew rate and time domain discrimination on the data to reject artifacts.

The 1% analog signal is applied to a 16-bit single slope A/D converter operating, in effect, as a pulse width modulator. A suitable 16-bit A/D converter is shown in schematic form in FIG. 4c.

As previously noted, arithmetic processing circuitry 400 includes a digital peak and slope detector 404. Digital peak and slope detector 404 includes a 5 MHz oscillator 405, cooperating with a 24-bit binary counter 406. The parallel outputs of counter 406 are applied to suitable timing decoder logic 408. Timing decoder logic 408 generates respective sequential timing signals ZCEP1, ZCEP2, and ZCEP3 at output terminals 408a, 408b and 408c, respectively.

A shift register 410 is clocked by signals from the last bit of counter 406. Shift register 410 is utilized to ensure that the processing circuitry reaches steady state before calculations are performed and generates the previously mentioned arithmetic enable signal at terminal 410a.

Digital peak and slope detector 404 is initialized by the master clear pulse from master clear one-shot 316. The master clear one-shot pulse is applied as a clear signal to counter 406 and to shift register 410. As previously described, the master clear one-shot is generated in response to powering up of the system, and out-of-limits impedance (indicative of improper electrode connections to the subject) or a change in the DC offset level. Shift register 410 effects a delay from initialization to ensure that all counters in the system have reached steady state, i.e., the counters have had time to be purged of false initial noise counts.

A 40 Hz sampling rate is established by the signal from bit 16 of counter 406. Bit 16 is coupled to input 402a of 16-bit A/D converter (pulse width modulator) 402. More specifically, bit 16 has a period of 25 msec., thus establishing 12.5 msec. convert period and a 12.5 msec. calculation period within the overall sampling period. At the beginning of the 12.5 msec. convert period, a linear ramp is generated in A/D converter 402. When the linear ramp reaches the value of the 1% analog signal at terminal 348a, the convert period is terminated, thus providing a pulse width modulated output signal at terminal 402b of 16 bit A/D converter 402. The pulse width modulated signal is inverted and applied to one input terminal of a two input NOR gate 436. The other input of NOR gate 436 is coupled to the 5 MHz clock signal. Thus, the pulse width modulated signal gates the clock signals to provide a number of pulses (hereinafter referred to as a Zcount) indicative of the 1% analog signal. The Z count is provided at terminal 436a.

The Z count and the respective timing signals from timing logic 408 are applied to suitable control logic 430 and steering gates 432 and 434, which alternately apply the Z counts and the timing signals from timing logic 403 to respective banks A and B of computation apparatus. Suitable control logic 430 and steering gates 432 and 434 are shown in schematic form in FIGS. 4d, 4e and 4f, respectively.

Computation apparatus A comprises a binary counter 412a, coupled in parallel with an up/down counter 414. Up/down counter 414a is in turn coupled in parallel with a plurality of comparators 416a, 422a, and 427a. Comparators 420a, 422a and 427a have coupled to the second set of inputs thereof hardwired preload values 418a, 424a and 428a, respectively. The A>B outputs of comparators 416a and 422a and the A<B output of comparator 428, are respectively applied to input terminals of a 4-input AND gate 420a, and three 3-input AND gates 426a and 429a. The second and third input terminals of AND gates 420a, 426a and 429a have applied thereto the ZCEP1 signal and the ZCTDNA signal generated at terminal 432a of steering gates 432, respectively. The fourth input terminal of AND gate 420β is responsive to the A<B output of comparator 428a.

The second computation apparatus (computation apparatus $\beta$) comprises a binary counter 412β, up/down counter 414β, comparators 416β, 422β and 427β and hard-wired preload 418β, 424β and 428β, 4-input AND gate 420β and 3-input AND gates 426β and 429β. Comparation apparatus $\beta$ is essentially identical to computation apparatus A, with the exception that AND gates 420β, 426β and 429β are responsive to the CNTDN$\beta$ signal generated at terminal 434b of steering gates 434, and in the control signals to counter 412β and up/down counter 414β.

Counters 412a and 412b are each 16-bit counters to accommodate numbers up to 65,000 (corresponding to a 10 V maximum 1% analog signal at sensitivity 10 ohms per volt, and A/D ramp timing such that 650 counts are generated per 100 mV).

Computation apparatus A and computation apparatus $\beta$ are utilized to provide amplitude discrimination against signals not associated with respiration, and in particular, the cardiac component. Two banks of calculation apparatus are utilized to provide for comparison of each sample to the just preceding sample. Control logic 430 and steering gates 432 and 434 apply the respective control signals to calculation apparatus A and calculation apparatus $\beta$ to effect the following operation. The counters are initially reset in response to the arithmetic enable signal from terminal 410a. Assuming computation apparatus A to be initially addressed, in response to the ZCEP2 control signal, the contents of binary counter 412a will be parallel loaded into up/down counter 414a. Binary counter 412b is reset by ZCEP3 from terminal 402c. During the next sampling period, the Z count is applied to increment binary counter 412b and to decrement up/down counter 414a. Thus, at the end of the conversion period: up/down counter 414a contains a count indicative of the absolute difference between the successive samples. The final state of the sign bit indicates whether the absolute difference is a positive or negative number; the binary counter 412b contains a count indicative of the last taken sample.

The difference count in up/down counter 414a is compared to the hardwired preload value of 418a. Preload 418a is chosen to be equivalent to 0.15 ohms, one-half the smallest amplitude change typically encountered in the physical respiration waveform. Comparator 416a provides a signal indicative of whether the Z count sampled has changed sufficiently from the last Z count to be considered valid.

As noted above, the A greater than B output (A>B) of comparator 416a is applied to a one input of 4-input AND gate 420a. The other inputs of AND gate 420a are the ZCEP1a signals from timing logic 408 and terminal 408a, the countdown A (CTDNA) control signal from steering gates 432 (originating in control logic 430), and the A<B output signal from comparator 427a, as will be explained. The output terminal 421a of AND gate 420a is coupled to control logic 430. The output of AND gate 420a will hereinafter be referred to as F(A)r. Generation of the F(A)r signal causes control logic 430 to toggle, in effect, reversing the roles of computation apparatus A and computation apparatus B.

If the difference count in counter 422 is not greater than the preload threshold count corresponding to 0.15 ohms, the relative roles of computation apparatus A and computation apparatus B are maintained as they were. The previous contents of binary counter 412a are again loaded into up/down counter 414a for comparison against the next successive sample (Z count) while the next sample is accumulated in binary counter 412b in computation apparatus B. Thus, one of computation apparatus A or computation apparatus B accumulate the Z count sample while the other subtracts the Z count from the previously accumulated sample and compares the difference to the predetermined count corresponding to one-half the desired sensitivity of the system. Any change between samples less than the preload threshold is thus, in effect, filtered out. Upon detection of a valid sample, calculation apparatus A and calculation apparatus B change roles, under the control of control logic 430 and steering gates 432 and 434. Computation apparatus A and computation apparatus B are to all effects and purposes identical, and, for the purposes of simplicity, the corresponding elements for the respective calculation banks will hereinafter be referred to generically by their numerical designation. For example, it will be understood that when comparator 416 is referred to as providing an A greater than B output to AND gate 420, that reference is made to analogous connections between comparator 416a and GATES 420a and between comparator 416b and AND gate 420b.

Differing sensitivities can be provided by comparing the difference between successive samples against different sensitivity preloads. For example, preloads 424 can be chosen to establish a sensitivity of 0.01 ohms. Accordingly, by gating in AND gate 426, the respective A greater than B (A>B) outputs of comparators 422 with ZCEP1 from terminal 408a of timing logic 408 and the countdown A control signal (CTDNA) from terminal 432b of steering gates 434 (or countdown B from terminal 434b), the cardiac component can be monitored to digitally develop a heart rate signal in a manner analogous to the analysis of the respiration waveform, as will be explained. It should be appreciated that such digital generation of a heart rate signal completely eliminates 60 cycle interference. With respect to monitor 100, this is a moot point in view of the shield driver previously described. However, in some instances certain cardiac diseases or anomalies greatly distort the ECG waveform; conventional ECG monitoring systems reject the waveforms as artifacts. In some instances, a digital generation of an heart rate signal could be desirable.

A still further comparison can be made against a preloaded threshold value equivalent to the maximum amount allowable change. That is, a comparison can be made to a count corresponding to the maximum slew rate physiologically possible in the human respiratory cycle. To this end, the A less than B (A<B) output of comparators 427 are used as inputs to AND gates 429 and 420. Assuming a maximum breath rate of 180 breaths a minute, the maximum change in transthoracic impedance during the sample period is less than 1 ohm. Accordingly, by setting the preload 428 threshold value at 1.5 ohms and inhibiting generation of the valid sample signals, F(A)r or F(B)r when the difference count exceeds the threshold by AND gates 420, high slew rate artifacts are rejected. A sample is therefore accepted as valid only in the event that it differed from the preceding valid sample by an amount exceeding one-half the sensitivity level of the system as established by preload 418, but also within acceptable maximum limits as determined by preload 428. Thus, both amplitude and slew rate discrimination are provided against artifacts.

Digital peak detector 404 provides an indication of the occurrence of respiration extrema. Signals indicative of the sign (zero crossover) of the difference counts in up/down counters 414a and 414b are applied to the respective inputs of a 2-input NAND gate 442. It should be appreciated that the sign of the difference between successive samples is indicative of the direction of slope of the respiration waveform between those sampling instances. Accordingly, the zero crossovers in up/down counters 414 and 422 are indicative of the occurrence of a respiration extrema. When either of up/down counters 414 transition from down counting to up counting (crossover zero), a low level sign signal is generated to NAND gate 442, forcing the output thereof to go high. The output of NAND gate 442 will hereinafter be referred to as the up/down flag signal.

The up/down flag signal and the valid count signals F(A)r (421a) and F(B)r (421b) are applied to a slope detector 445. The up/down flag signal is applied to the data input of a D flip-flop 444 and to the clear input of a flip-flop 446 operating as a divide-by-2 circuit. Flip-flop 446 is clocked in response to transitions between the A and B computation apparatus. The clock signal to flip-flop 446 is provided by a 2-input NOR gate 448 having the respective inputs thereof connected to terminals 421a and 421b, respectively. Divide-by-2 flip-flop 446 adjusts the effective sensitivity of the system to 0.3 ohms (hence the setting of preload 418 at 0.15 ohms). The output of flip-flop 446 is utilized to clock flip-flop 444. The Q and $\overline{Q}$ outputs of flip-flop 444 are used to drive an inspiration indicator and expiration indicator, respectively.

So long as the samples are increasing in value, i.e., the slope is positive, a zero crossover (sign change) will occur. Similarly, if no zero crossover occurs, it is indicative that the successive samples are decreasing in value, i.e., the slope is negative. The output of D flip-flop 444 reflects the up/down flag signal and is thus indicative of the direction of slope of the respiration waveform. The Q input provides an indication of positive slope (terminal 444a) and the $\overline{Q}$ output provides an indication of negative going slope (terminal 444b).

Figure 5:
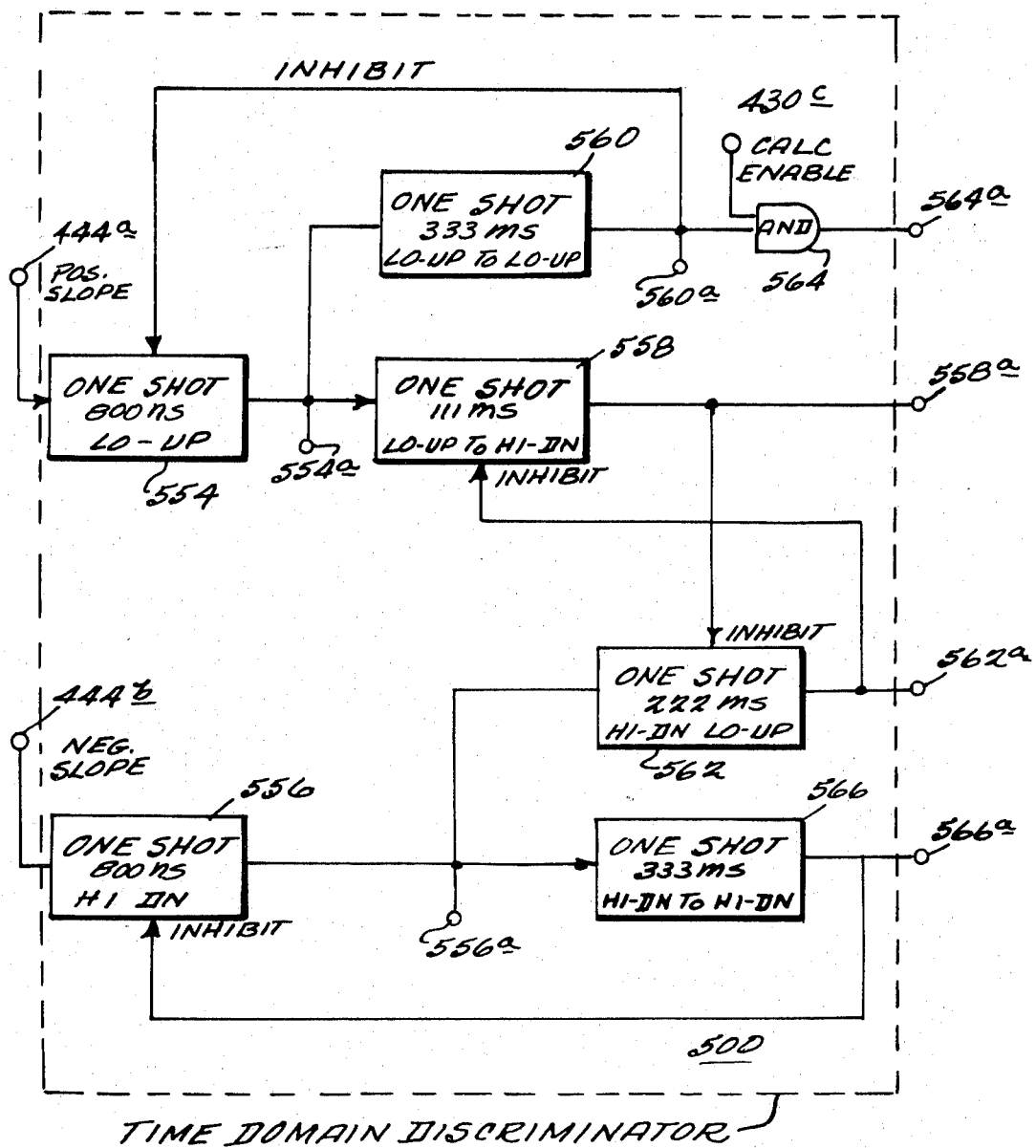
FIG. 5 is a block diagram of time domain discriminator 500.

The positive slope and negative slope output signals provide at terminals 444a and 444b of digital peak detector 404 are applied to time discrimination circuitry 500. Time discrimination circuitry 500 discriminates with respect to artifacts occurring outside the physiological time constraints of the respiration cycle. For example, maximum and minimum time periods between the relative events in the respiration cycle have been empirically established, and signals not falling within the physiological limits are rejected as artifacts. Referring now to FIG. 5, time domain discriminator 500 will be described in more detail.

Time domain discriminator 500 comprises a plurality of one-shots: two 800 nsec. one-shots, a 111 msec. one-shot 558, and a 222 msec. one-shot 562. All of the one-shots are enabled by the calculate enable signal provided at terminal 430c of control logic 430 (connections not shown). The pulse widths of the one-shot outputs are chosen in accordance with the particular subject population on which the apparatus is to be used. The pulse widths herein described, relate to infants. The pulse widths would differ for different subject populations such as older children or adults. The maximum physiologically possible breath rate can be established for the population (180 breaths per minute in infants). Accordingly, successive inspiratory or expiratory peaks can not reoccur within a period of on the order of 333 msec. Further, inspiratory to expiratory ratio are on the order of 1-to-2, that is, expiration time is twice the inspiration time. It therefore follows that a minimum period of on the order of 111 msec. occurs between an inspiratory peak and an expiratory peak. Similarly, a minimum period on the order of 222 msec. will pass between the occurrence of an expiratory peak (maxima) and inspiratory peak (minima). The relative time relationships are illustrated in graphic form in FIG. 5a.

When the slope of the respiratory waveform (1% analog signal) changes from negative to positive, indicative of a minima in the waveform (expiratory peak) flip-flop 444 changes state, generating a high output at positive slope terminal 444a. The positive going transition causes one-shot 554 to trigger (assuming one-shot 554 is not inhibited by one-shot 560, as will be explained). The 0.8 μsec. pulse generated by one-shot 554 at terminal 554a will hereinafter be referred to as the low-up pulse. It must be appreciated that in view of the 0.15 ohm preload in 418 (establishing a 0.3 ohm sensitivity) the occurrence of a low-up pulse corresponds to a point on the respiratory waveform within 0.3 ohms of the minima. Taking the worst case, the figure 0.3 arises as follows. Referring to the 1% analog respiration waveform of FIG. 5a, assume that the minima corresponds to a thoracic impedance of 100 ohms. Assume a first sample S1 is taken and a count corresponding to 98.85 ohms is accumulated in binary counter 512, and that a negative slope signal is provided by flip-flop 444. Assume the next successive sample S2 occurs at the peak (100 ohms). The difference is thus 0.15 ohms. When compared to the preload sensitivity threshold value 0.15, an A greater than B signal is not generated, and sample S2 ignored. The 98.85 count is thus retained in counter 412 and loaded into up/down counter 414 for differencing with the next successive sample S3. Assuming sample S3 to correspond to a transthoracic impedance of 98.85 ohms, that sample S2 will be filtered out by the amplitude discrimination. The next sample, however, S4 (here 98.6 ohms) will cause a zero crossover in up/down counter 414b causing generation of the up/down flag and a positive transition in the positive slope signal at terminal 444a. Thus, a low up pulse is generated at terminal 554a by one-shot 554. The low-up pulse triggers 111 msec. one-shot 558 and 333 msec. one-shot 560. The output of one-shot 560 is fed back to one-shot 554 as an inhibit signal to establish the minimum relative timing between the occurrences of low-up pulses (respiration minima). Any apparent negative to positive slope transition occurring within 333 msec. of the last previous negative to positive transition, must be due to an artifact, and accordingly, one-shot 554 is inhibited with respect to the second transition. One-shot 558 establishes the minimum relative time between the negative to positive transition and positive to negative transition.

Similarly, 0.8 μsec. one-shot 556 is triggered by positive going transitions in the negative slope by one-shot 556, at terminal 556a, is indicative of a positive to negative slope transition in the respiration waveform and will hereinafter be referred to as the high down pulse. One-shot 556 is similarly inhibited by 333 msec. one-shot 566 to discriminate against apparent positive to negative slope transitions occurring too soon after a previous negative to positive transition. One-shot 562, triggered by the high down pulse generates a pulse indicative of the minimum time between positive and negative and negative to positive slope transitions in the waveform. Further, since the time periods represented by one-shots 558 and 562 are mutually exclusive, the outputs of the respective one-shots are utilized to inhibit each other.

As previously noted, the one-shots of time domain discriminator 500 are enabled by the calculate enable signal from terminal 430c of control logic 430. The calculate enable signal is generated by a shift register within logic 430 and operates to insure that the system is in steady state before any alarm signals or X-ray trigger signals are generated.

The 333 msec. low-up to low-up pulse generated by one-shot 560 in response to the low-up pulse is gated to respiration tachometry circuitry 600. Respiration tachometry circuit 600, in effect, measures the period between the leading edges of successive low-up to low-up pulses, to determine the respiration rate. Both the instantaneous rate, (the rate during each successive interval), and an indication of the rate averaged over a predetermined number of events are provided.

Figure 6A:
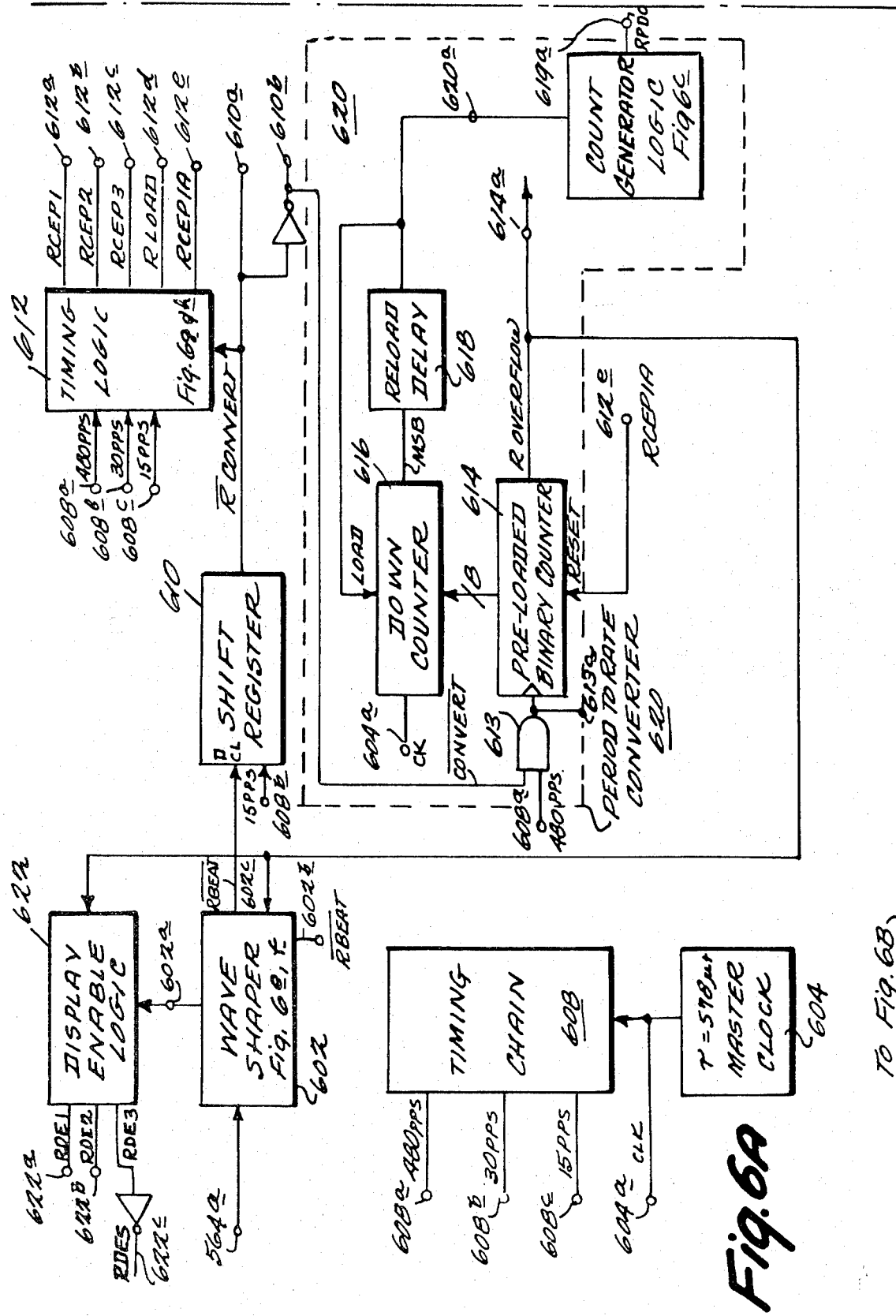

Referring now to FIG. 6, and in particular FIG. 6a, a more detailed description of respiration tachometry circuit 600 will be provided. The gated pulse indicative of the occurrence of low-up (terminal 564a) is applied to a waveshaper 602. A suitable waveshaper 602 is shown in schematic form in FIG. 6e. Waveshaper 602, in effect, standardizes the input signal at a proper logic voltage level. Waveshaper 602 generates at an output terminal 602a an "event" signal, synchronous with the leading edge of the one-shot pulse generated at terminal 564a. In addition, almost simultaneously with the generation of the event signal, waveshaper 602 generates a narrow pulse Rbeat at terminal 602b (and $\overline{\text{Rbeat}}$ at terminal 620b). Rbeat synchronizes the rest of the respiration tachometry circuit 600, generated in response to the first master clock signal occurring after the "event." The clock signals are generated by a master clock 604 having a time constant of 578 μsec. The timing of the output signals of the respective elements of waveshaper 602 are shown in FIG. 6f.

The master clock signal is also applied to a timing driver chain 608 which generates at respective output signals 608a, 608b and 608c, respective 480 pulse per second, 30 pulse per second, and 15 pulse per second signals.

The $\overline{\text{Rbeat}}$ output provided at terminal 602c of waveshaper 602 is applied to the clear input of a shift register 610. Shift register 610 is clocked by the 15 pulse per second signal from timing chain 608, and establishes a logically true signal Rconvert for a 66 msec. period following $\overline{\text{Rbeat}}$, hereinafter referred to as the convert period. The Rconvert signal is generated at terminal 610a and the $\overline{\text{Rconvert}}$ signal generated at terminal 610b. The Rconvert signal is applied to suitable timing logic 612, together with the 480, 30 and 15 pulse per second signals from timing chain 608, to generate respective control signals RCEP1 at terminal 612a, RCEP2 at terminal 612b, RCEP3 at terminal 612c, Rload at terminal 612d and RCEP1a at terminal 612e. Suitable timing logic 612 is shown in FIG. 6g. The relative time relationship of the respective signals are shown in diagrammatic form in FIG. 6h.

The $\overline{\text{Rconvert}}$ signal (610b) and the 480 pps signal (608a) are applied to a period to rate converter 620. In effect, converter 620 accumulates a count at the 480 pps rate indicative of the period between respective beat signals in a counter 614. The accumulated count is loaded into a down counter 616. Counter 616 is thereafter repetitively counted down at the clock frequency during the convert period. Each time down counter 616 counts down to zero, a most significant borrow bit is generated and passed through a delay 618 to count generator logic 619. The delayed most significant bit is fed back to down counter 616 to cause the counter to reload with the period count accumulated in counter 614. The number of times down counter 616 counts down (i.e., the number of msb bits generated) during the convert period is indicative of the instantaneous respiration rate.

In practice, the 480 pulse per second signal is gated through a NAND gate 613 to clock counter 614 only during the convert period. Accordingly, binary counter 614 is preloaded with a count corresponding to the known (66 msec.) duration of the convert period, i.e., 38 counts. Binary counter 614 is reset by the RCEP1a control signal generated at terminal 612a of timing logic 612.

Figure 6B:
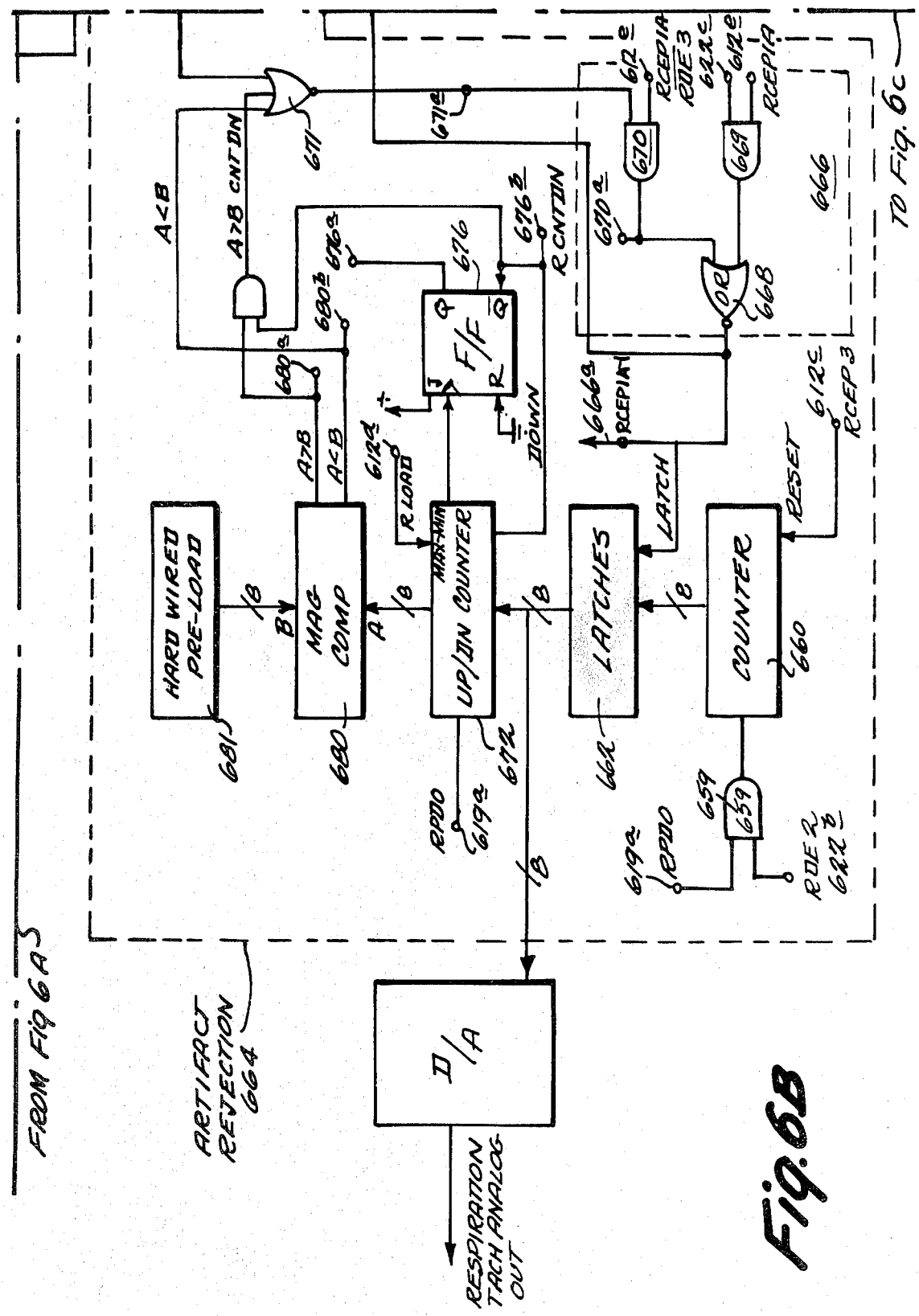
Figure 6D:
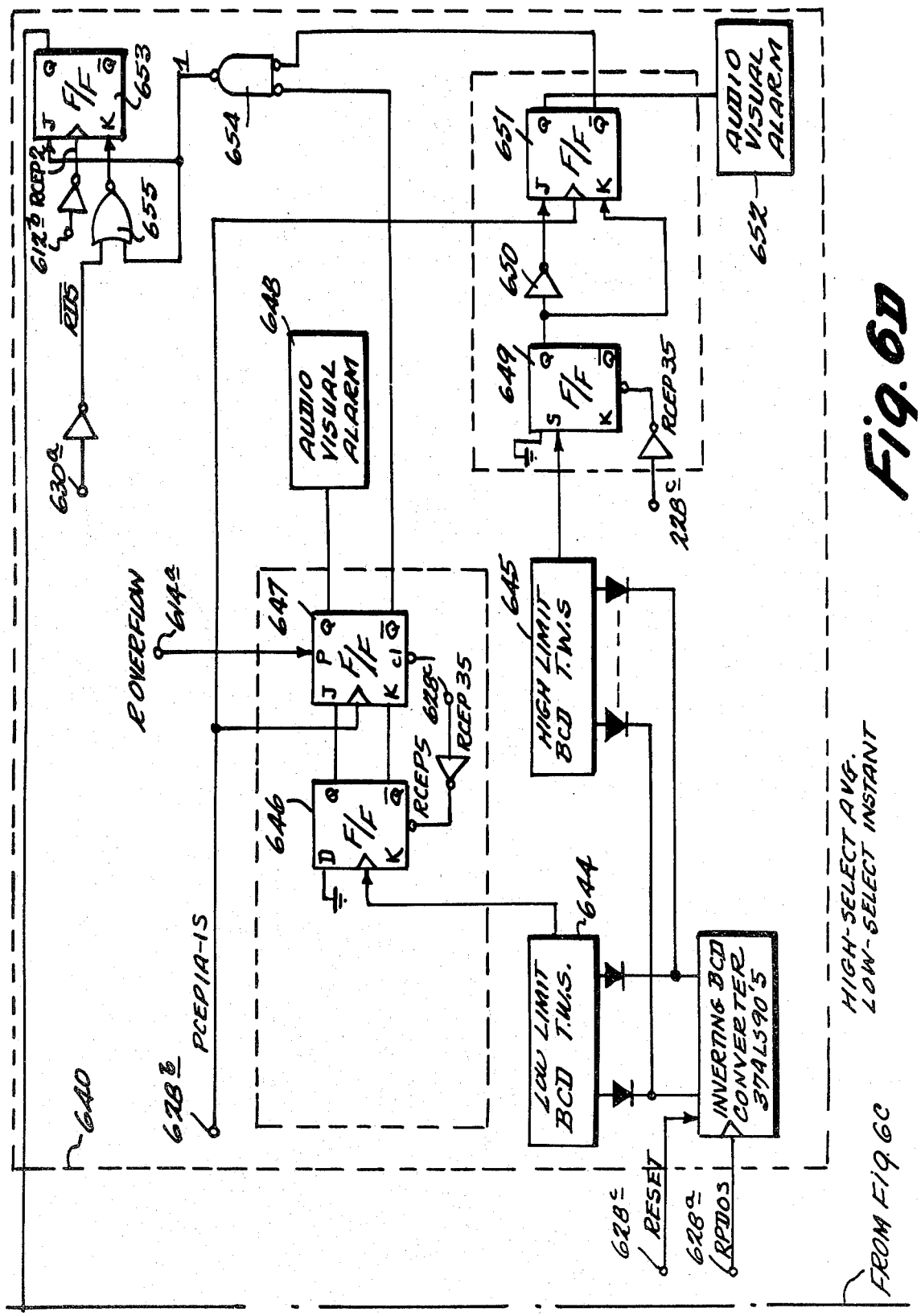
Figure 6F:
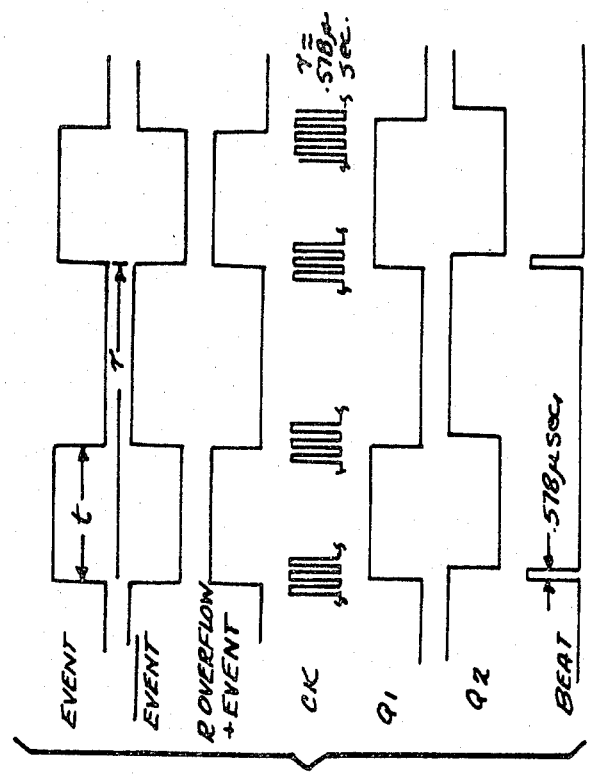
FIGS. 6e and 6f are a timing diagram and a schematic diagram of a suitable wave shaper 602.
Figure 6E:
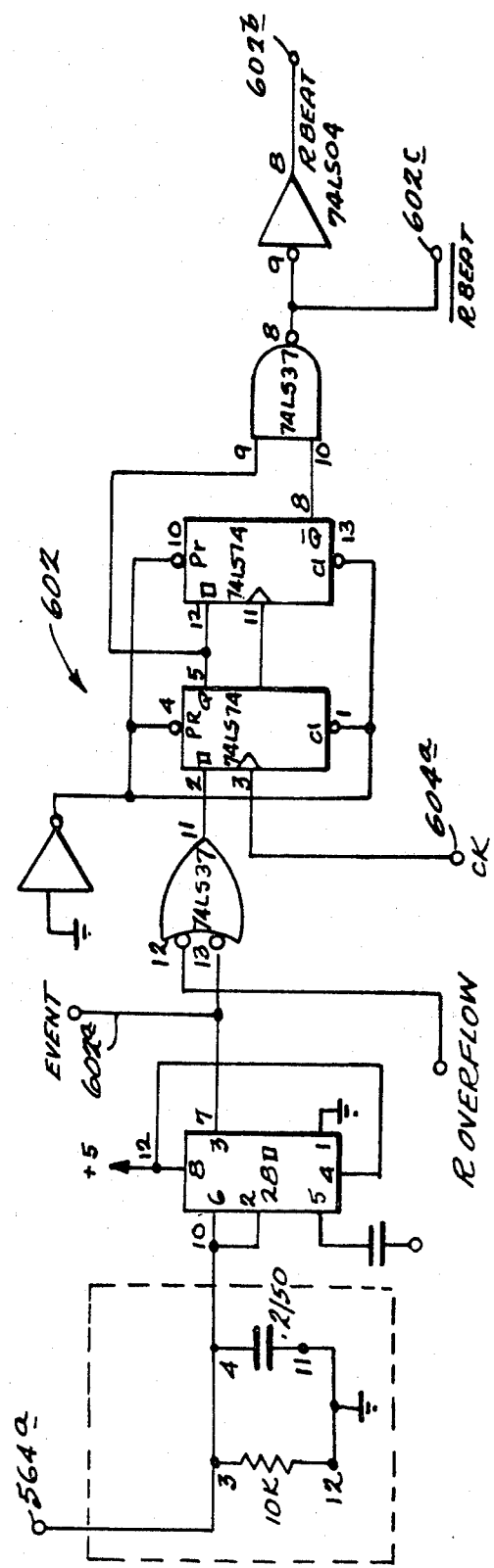
Figure 69:
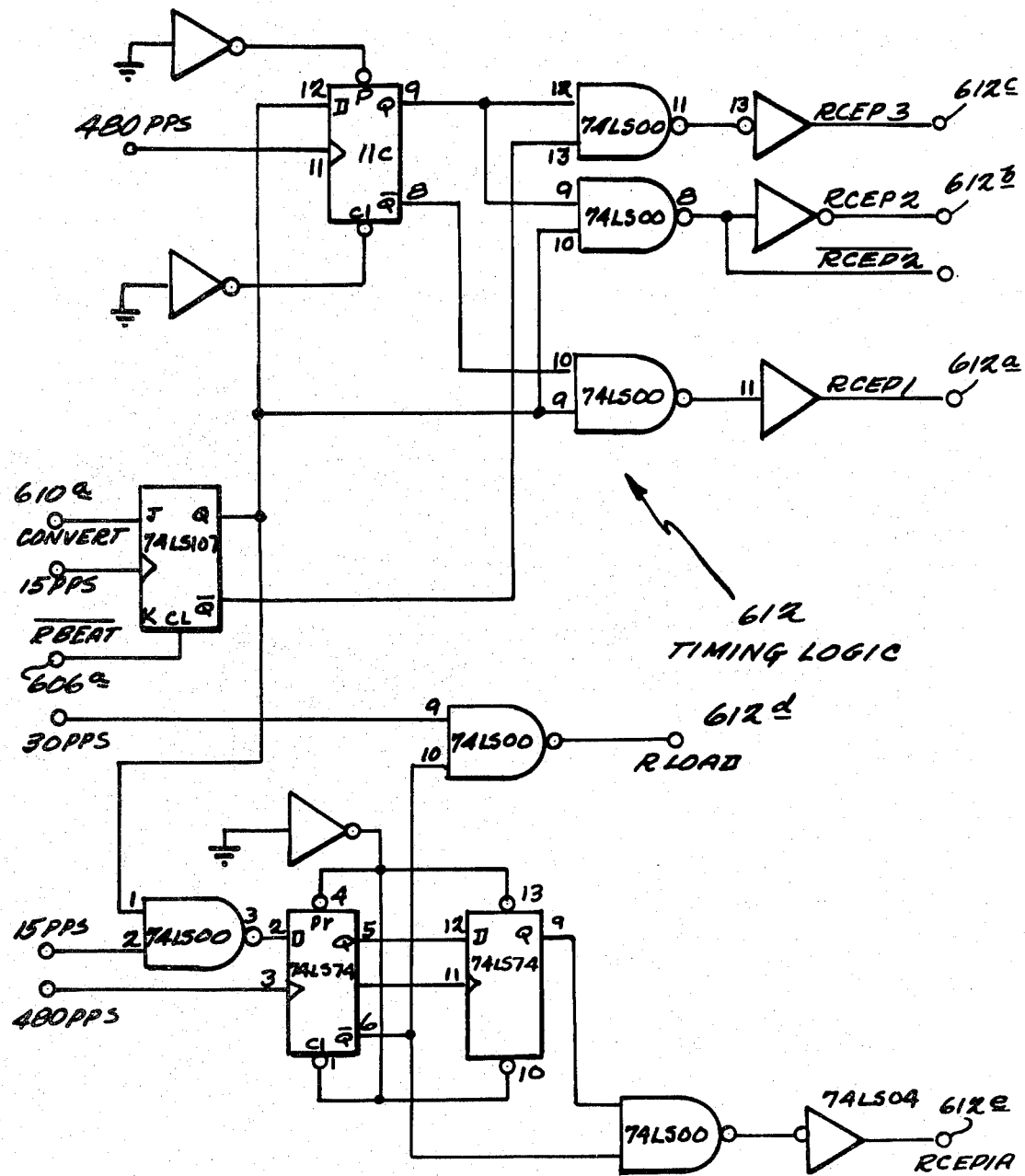
Figure 6H:
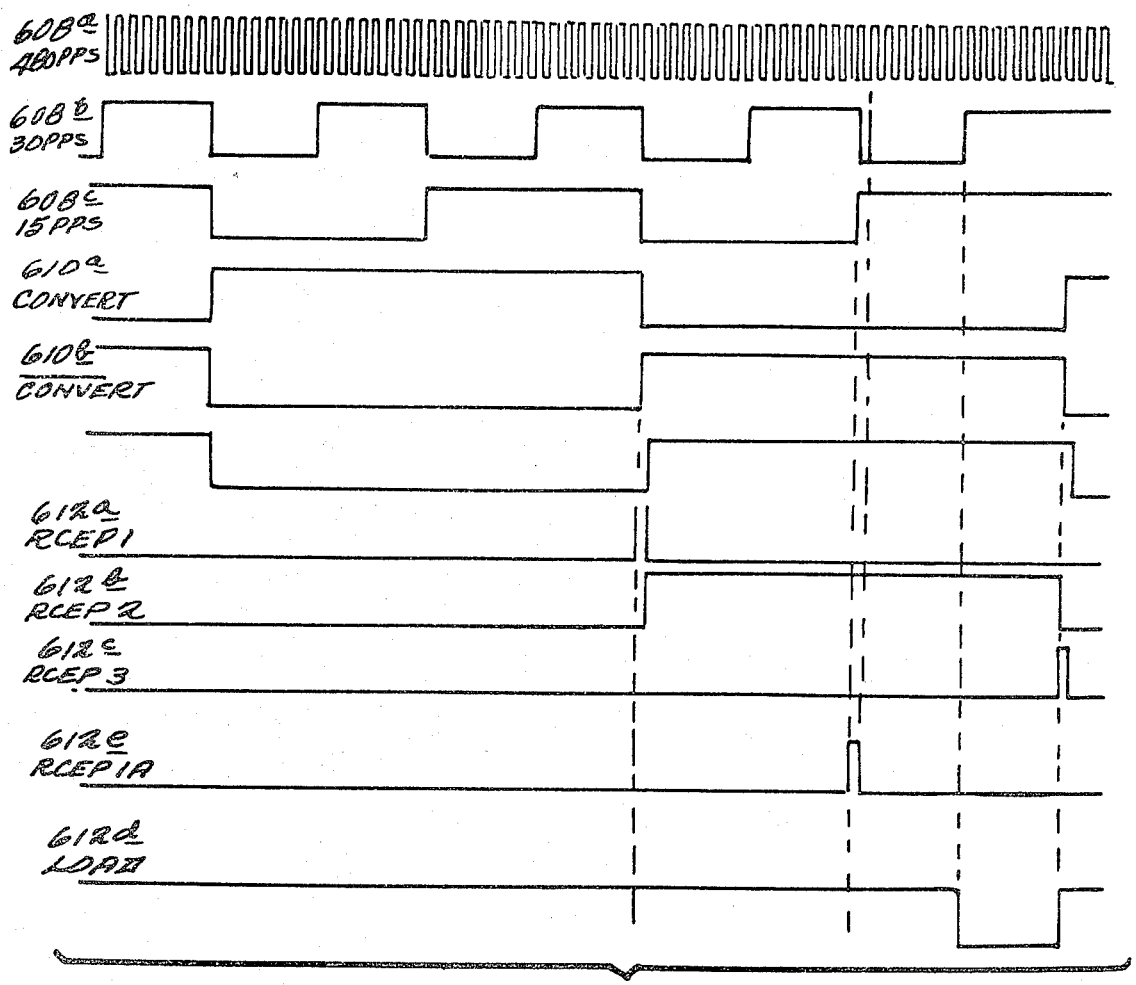
FIG. 6h is a schematic diagram and timing diagram relating to suitable timing logic 612.
Figure 6I:
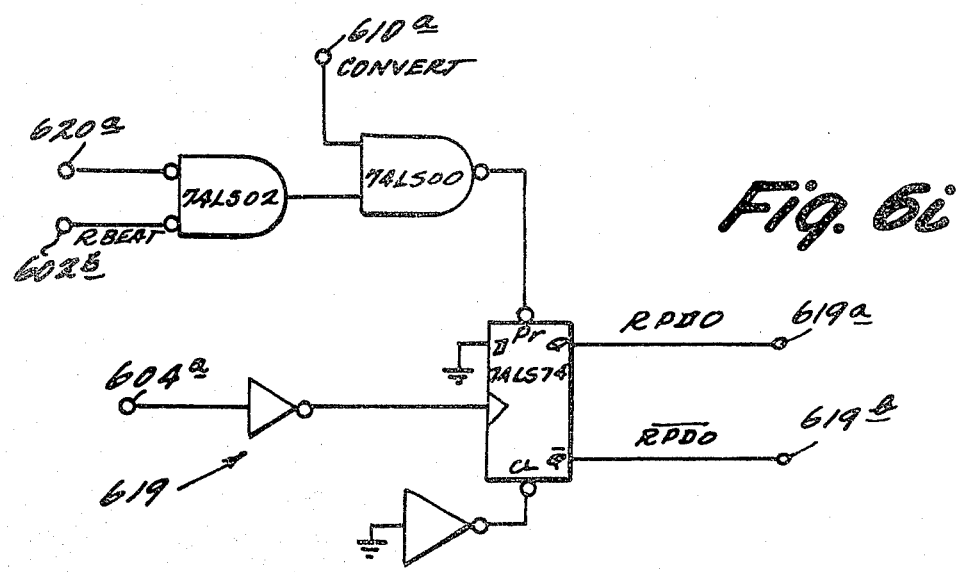
FIG. 6i is a schematic diagram of suitable unit generator logic 619.

Suitable count generator logic 619 is shown in FIG. 6i. Count generator logic 619, in effect, gates the most significant borrow bit from up/down counter 616 during the convert period to generate an RPDO count. The number of RPDO counts is indicative of the instantaneous respiration rate in breaths per minute.

It should be appreciated that other varieties of period to rate converters can be utilized. However, period to rate converter 620 is particularly advantageous in that 7-segment LED displays can be directly driven without the necessity of look-up tables, as will be explained.

Counter 614 also generates an R overflow signal in the case of an anomaly, that is, if the $\overline{\text{Rconvert}}$ period (indicative of the respiration period) extends beyond predetermined bounds. Counter 614 can accumulate a count up to 2048 (corresponding to 16 seconds). If the respiration period exceeds 16 seconds, an R overflow signal is generated at terminal 614a. Generation of R overflow resets the counters to zero, activates an apnea alarm and clears display enable logic 622 (as will be described).

It should be appreciated that it requires the occurrence of two events (low-up pulses) to provide a valid computation of respiration rate. Accordingly, the display is blanked until a valid calculation is attained. The display blanking function is performed by display enable logic 622. Display enable logic 622 is responsive to the event signal from waveshaper 602 and to the R overflow signal provided by counter 614 at terminal 614a. Display enable logic 622 generates respective control signals RDE1, RDE2, RDE3 at terminals 622a, 622b and 622c. Display enable logic 622 is essentially a shift register with data input tied high, clocked by the event pulses and reset by R overflow (614a) or master clear.

Artifact rejection, that is discrimination against spurious counts is also provided in respiration tachometry circuit 600 by artifact rejection logic 664, shown in FIG. 6b. It is physiologically impossible for the breath rate of a subject to increase by more than a predetermined amount during the course of a sampling period. The predetermined amount may be an empirically determined maximum for the particular population group of the subject, e.g., plus 20 beats per minute for an infant, or may be adaptively determined on a percentage of previous rate basis. Accordingly, when a rate count exceeds the previous rate count by more than the permissible amount, that rate count is deemed to be a spurious count and is rejected. Further, provisions must be taken not to incorporate the spurious count into the computation of average rates. However, it must be appreciated that the maximum change limit pertains only to increasing in respiratory rate; apnea may occur almost instantaneously.

In addition, the possibility of a spurious initial count must be considered. Accordingly, if a predetermined number of successive rate counts exceed the base count by more than the predetermined limit, the base count is assumed to be an error and the later rate counts used as a new base for computation.

With reference now to FIG. 6b, artifact rejection logic 664, will now be described. The RPDO counts from period to rate converter 620 (terminal 619a) are applied to one input of a 2-input NAND gate 659. NAND gate 659 gates the RPDO counts to clock an 8-bit binary counter 660. Counter 660 is reset by the RCEP3 signal generated at terminal 612c of timing logic 612. The parallel outputs of counter 660 are in turn applied to the inputs of an up/down counter 672. The outputs of up/down counter 672 are applied to one set of inputs of a magnitude comparator 680. The other set of inputs of magnitude comparator 680 cooperate with a hardwired preload 681 representative of a predetermined maximum limit on the amount of change physiologically possible between respective events (breaths). It should be appreciated that rather than a fixed maximum, an adaptive system whereby a difference is compared to a predetermined percentage of the preceding sample may be utilized.

After the system has warmed up, i.e., 2 events have occurred, NAND gate 659 gates the RPDO counts to counter 660. Thus, at the end of each convert period, counter 660 has accumulated a count indicative of the instantaneous respiration rate.

Latches 662 establish the base respiration count against which subsequent counts are compared. The base respiration count is the last occurring valid (within the system constraints) rate count sampled. As noted above, the rate count is deemed a valid sample if it does not differ from the preceding base rate count (contents of latches 662) by more than the predetermined limit established by preload 681. The rate count is similarly deemed to be valid if the sample differs from the preceding base count by more than the predetermined limit, but is a decreasing rate, or if a predetermined number (e.g., 5) of preceding rate samples have been deemed invalid as out-of-limits (indicating that perhaps the previous base count was spurious).

The accumulation of a valid count in counter 660, is signified by the generation of the RCEP1a-1 signal (valid count) generated at terminal 666a of logic 666. The accumulated count in counter 660 is selectively latched in latches 662 to update the base count in response to the RCEP1a-1. The RCEP1a-1 signal is generated by a 2-input OR gate 668. One input of OR gate 668 is receptive of the output signals from a 2-input AND gate 669. The inputs of AND gate 669 are responsive to the $\overline{RDE3}$ signal derived from terminal 662c of display enable logic 662 and the RCEP1a signal generated at terminal 612e of timing logic 612.

The other input of OR gate 668 is responsive to the output signal of a 2-input AND gate 670. One input of AND gate 670 is responsive to the RCEP1a signal at terminal 612e. The other input terminal of AND gate 670 is responsive to the output of a 3-input OR gate 671. The respective inputs to OR gate 671 are responsive to the output of a 2-input AND gate 694 operating upon the A greater than B (A>B) from comparator 670 and the countdown signal RCNTDN (as will be described); to the A less than b (A<B) signal generated by magnitude comparator 680 at terminal 680b; and to a "force" signal generated by the QE (bit 5) output of a shift register 690 (FIG. 6c). Shift register 690 is indexed by the RCEP1 signal of timing logic 612 and is reset by $\overline{RCEP1a\text{-}1}$. The QB (second bit) output is provided to X-ray trigger circuit 700 (arming logic 704), such that one spurious count will interrupt the arm cycle.

During the first three periods of operation (during initial start-up or after a reset), the contents of counter 660 is transferred to the output of latches 662 to establish an initial rate base count. For the first three periods, signal $\overline{RDE3}$ is high. A high $\overline{RDE3}$ forces AND gate 669 high. Accordingly, OR gate 668 generates a high level RCEP1a-1 signal, causing the content of counter 660 to be latched over into latches 662.

The difference between the instantaneous respiration rate sample and the base rate is established by up/down counter 672. After each convert period control signal Rload is generated by timing logic 612. The Rload signal is applied as a load command to up/down counter 672, causing the contents of latches 662 to be loaded into up/down counter 672. The up/down control of up/down counter 672 is effected through a JK flip-flop 676, having J input tied high and K input tied to ground. Flip-flop 676 is clocked by the max/min output (occurring at zero count) of counter 672 and is cleared by the Rload signal generated by timing logic 612. The Q output of flip-flop 676 is tied to the down control of up/down counter 672. The $\overline{Q}$ output of flip-flop 676 also provides the count down signal to AND gate 694. Thus, at the same time counter 672 is loaded with the contents of latches 662, flip-flop 676 is cleared to place up/down 672 in a down count mode. The next set of RPDO counts count up/down counter 672 down. At the end of the convert period, up/down counter thus contains a count equal to the difference between the stored count and the instantaneous period count. It should be appreciated that in the event up/down counter 672 reaches zero, flip-flop 676 is clocked, causing the Q output to go high and $\overline{Q}$ to go low. Up/down counter 672 will thus enter an up count mode. In addition, at the end of the convert period the instantaneous period count has been accumulated in counter 660.

The difference count in up/down counter 672 is compared to the preloaded threshold by magnitude comparator 680 and an A greater than B (A>B) or A less than B (A<B) signal generated accordingly. If A is less than B (A<B) the present count accumulated in counter 660 is latched by latches 662 at the RCEP1a time. That is, if A is less than B, OR gate 671 provides a high level output signal at terminal 671a to enable AND gate 670 with respect to the RCEP1a latch control signal. Accordingly, OR gate 668 generates the RCEP1a-1 output signal at terminal 666a, causing latches 662 to latch the accumulated count in counter 660.

It is desired, however, that the maximum limit on rate change be applied only to increases in respiratory rate. Accordingly, where the second rate is less than the previous rate count, the lesser value is latched into latches 662 irrespective of the absolute difference in the rates. A decrease in rate is signified by retention of the down count mode of operation by down counter 672 at the end of the convert period, and, thus by a count down signal (RCNTDN) generated at the $\overline{Q}$ output of flip-flop 676. Accordingly, when the difference between respective rate counts exceeds the maximum increase threshold(A greater than B) and a high level down count signal is provided by flip-flop 676 $\overline{Q}$, AND gate 694 generates a high level output signal, causing OR gate 671 to enable AND gate 670 with respect to the RCEP1a signal. Upon the next occurrence of the RCEP1a signal the RCEP1a-1 signal will therefore be generated at terminal 666a, causing latches 662 to latch the contents of counter 660 (the second rate count).

As noted above, a possibility exists that an erroneous base count is established in latches 662. An erroneous base count arises primarily through the initial establishing of the base count in latches 662 during the first three samples of operation after reset. Accordingly, if a predetermined number of sequential samples are deemed out of limits, it is assumed that the present base rate is in error and the subsequent rate latched as the new base rate. This is accomplished by shift register 690. Shift register 690 is indexed in response to each RCEP1 signal, indicative of each sample taken, and is reset by the RCEP1a-1 signal. Thus, if five samples are taken, that is, shift register 690 is indexed by five successive RCEP1a signals, without an intervening reset RCEP1a-1 pulse (indicative of a valid sample), the QE output of shift register 690 goes high to generate a "force" signal to OR gate 671. The high level output of OR gate 671 enables AND gate 670 with respect to the next occurring RCEP1a pulse. Accordingly, the next RCEP1a pulse is passed through AND gate 670 and OR gate 668 to generate the RCEP1a-1 signal causing the last rate count accumulated in counter 660 to be latched in latches 662 as the new base rate and resets shift register 690.

As previously noted, both an average respiration rate and the instantaneous respiration rate are selectively displayed. The selective averaging is provided by select averaging logic 624 shown in FIG. 6c. Selective averaging logic 624 comprises a divide-by-5 circuit 626 operative on the RPDO counts from period to rate converter 620. The RPDO counts and the output of the divide-by-5 circuit 626 are applied to multiplexed inputs of a multiplexer 628 to provide a selected RPDOS count at the output terminal of the 628a of the multiplexer 628. Similarly, the $\overline{\text{Rconvert}}$ signal (610b) from shift register 610 clocks a divide-by-t counter 630 to provide an RD5 output signal. The RD5 output signal is applied to one input of each of two 2-input NAND gates 632 and 634. The other input of NAND gte 632 is coupled to the output of (670a) of 2-input AND gate 670. The output (670a) of AND gate 670 will hereinafter be referred to as the valid RCEP1a-1 signal. The valid RCEP1a-1 signal is applied together with the output signal (valid RCEP1a-1D5) of NAND gate 632 to two multiplexed inputs of multiplexer 628 to provide a RECP1a-1S output signal at terminal 628b of the multiplexer. The second input of NAND gte 634 is receptive to the RCEP3 signal generated at terminal 612c of timing logic 612. The output of NAND gate 634 (RCEP3D5) and the RCEP3 signal are applied to two multiplexed inputs of multiplexer 628 to provide a RECEP3S signal at terminal 628c of the multiplexer. Counter 630 is reset by the output of a 3-input NAND gate 638. NAND gate 638 is responsive to the A greater than B signal generated by magnitude comparator 680, the R count up signal generated by flip-flop 676 at terminal 676a and the RCEP1a signal generated at timing logic terminal 612c.

The average is taken over five respiration periods. The five respiration period averaging interval is established by, in effect, dividing the $\overline{\text{Rconvert}}$ signal generated at terminal 610b of shift register 610, by five. It should be recalled that the RPDO counts are generated during the convert time, the number of counts generated during that time being indicative of the rate. Accordingly, the $\overline{\text{Rconvert}}$ signal from terminal 610b is applied to a divide-by-5 counter 630. Divider 630 generates a high level output signal RD5 during the fifth $\overline{\text{Rconvert}}$ period. The RD5 signal is applied to NAND gates 632 and 634 to gate one-in-five valid RCEP1a-1 pulses to generate the signal RCEP1a-1D5 and one-in-five RCEP3 pulses to generate the signal RCEP3D5. Simultaneously, divide-by-5 counter 626 is generating output pulses in response to one-in-five RPDO counts. Accordingly, during the averaging mode, multiplexer 628 provides at its outputs 628a, 628b and a pulse train indicative of one-fifth (1/5) of the RPDO counts, every fifth valid RCEP1a-D5 count (i.e., every fifth output pulse from AND gate 670) and every fifth RCEP3 reset pulse. The time relationship of the respective signals relating to selective averaging logic 624 are shown in FIG. 6j.

In the event of a spurious count (A>B and R counting up) the operation of selective averaging logic 624 is inhibited, by resetting divide-by-5 counter 630. Application of the reset pulse to divide-by-5 counter 630 causes counter 630 to assume all 1's generating a high RD5 signal until the next negative transition of $\overline{\text{Rconvert}}$. The high level RD5 signal resets counter 626 and causes generation of RCEP3D5 upon the next occurring RCEP3 pulse, to effect reinitialization of various components of an alarm circuit 640.

Alarm circuit 640, shown in FIG. 6d, comprises an inverting BCD counter 642. BCD counter 642 suitably comprises three 74LS90 integrated circuits. BCD counter 642 is clocked by the RPDOS signal provided at multiplexer output terminal 628a, and is reset by the RCEP3S signal provided at multiplexer output terminal 628c. The parallel outputs of BCD counter 642 are coupled through diodes to a low limit BCD thumb-wheel switches 644. The parallel outputs of BCD counter 642 are also applied through diodes to high limit BCD thumb-wheel switches 645. Thumb-wheel switches 644 and 645 generate high level output signals when the count in BCD counter 642 equals the respective setting on the thumb-wheel switches.

The output of low limit thumb-wheel switches 644 is applied to the clock input of a D flip-flop 646. The D input of flip-flop 646 is tied to ground, and the preset input responsive to $\overline{\text{RCEP3S}}$, generated from the RCEP3S signal at multiplexer terminal 628c. Flip-flop 646 is thus initially set, providing a high $\overline{Q}$ output signal, and is clocked low when the BCD count equals the low limit set in thumb-wheel switches 644. The Q output of flip-flops 646 is applied to the J input of a JK flop 647. The K input of flip-flop 647 is responsive to the inverted Q output signal ($\overline{Q}$) of flip-flop 646. JK flip-flop 647 is clocked by the RCEP1a-1 signal generated at multiplexer output 628b, and is preset by the R overflow signal generated by counter 614 at terminal 614a. The Q output of flip-flop 647 is applied as a control signal to an audio visual alarm 648.

The output of high limit thumb-wheel switches 645 is applied to the clock input of a D-type flip-flop 649. D-type flip-flop 649 is connected in a configuration identical to flip-flop 646 with D input tied to ground and preset responsive to the $\overline{\text{RCEP3S}}$ signal derived from the output of multiplexer terminal 628c. The $\overline{Q}$ output of flip-flop 649 is applied through an inverter 650 to the J input of a JK flip-flop 651, (so shown for emphasis in distinguishing from flip-flops 646 and 647). JK flip-flop 651 is clocked by the RCEP1a-1S signal provided at multiplexer output 628b. The K input of flip-flop 651 is receptive of the Q output signal from flip-flop 649.

In operation, when the count in BCD counter 642 equals the low limit set on thumb-wheel switches 644, flip-flop 646 is clocked, causing the Q output thereof to change from high to low. Accordingly, a low J-input and high K input are provided to flip-flop 647. Thus, upon the next subsequent RCEP1a-1S time, flip-flop 647 will generate a low Q output and a high $\overline{Q}$ output. Thus, if the count in BCD counter 642 exceeds the low limit set on thumb-wheel switches 644 during the appropriate accumulation time, no alarm is generated.

However, if at the end of the accumulation time, (convert or RD5) associated with RPDOS, the low limit set on thumb-wheel switches 644 has not been reached, no clock signal is applied to flip-flop 646, and accordingly, at the RCEP1a-1S time, the inputs to the J and K terminals of flip-flop 647 are values one and zero. Accordingly, when clocked by the RCEP1a-1S pulse and the Q output goes high and an audio visual alarm is initiated.

Audio visual alarm 652 is activated if the high limit threshold set in thumb-wheel switches 645 is reached by the count in BCD counter 642. If the count is not reached, no alarm is sounded. When the content of BCD counter reaches the high limit threshold, thumb-wheel switches 645 clock flip-flop 649 causing the Q output thereof to go low. Accordingly, at the RCEP1a-1S time, a one is applied to the J input and a zero applied to the K input of flip-flop 651. When clocked by the RCEP1a-1S pulse, flip-flop 651 therefore generates a high level Q output signal to initiate an alarm.

In normal steady state opertion, (no high or low alarm conditions present) the RCEP1a-1D5, RCEP3D5 and RPDOD5 signals are provided at multiplexer output terminals 628b, 628c and 628a. The alarm function therefore, is operating on the basis of a five breath averaged interval. However, in the event of a high or low limit alarm condition occurring, it is desirable to operate thereafter in response to the instantaneous respiraton rate until the averate rate returns to normal limits. To this end, the select input to multiplexer 628 operates in response to the Q output of a JK flip-flop 653. The J input of flip-flop 653 is responsive to the outut of a 2-input NOR gate 654. The inputs to NOR gate 654 are coupled to the $\overline{Q}$ outputs of flip-flops 647 and 651. The K input of flip-flop 653 is responsive to the output of a 2-input NAND gate 655. The inputs of NAND gate 655 are $\overline{RD5}$ (derived from the RD5 signal provided at output terminal 630a of selective averaging logic 624) and the output of NOR gate 654. Flip-flop 653 is clocked by the $\overline{RCEP2}$ signal derived from the RCEP2 signal provided at timing logic output terminal 612b. When no alarm condition exists, the $\overline{Q}$ outputs of flip-flops 647 and 651 are both low. Accordingly, the output of NOR gate 654 is high providing a high input to the K input terminal of flip-flop 653. The $\overline{RD5}$ signal is high and NAND gate 655 provides a low input at the K input terminal of flip-flop 653. Accordingly, the $\overline{RCEP2}$ signal clocks the Q output of flip-flop 653 high causing multiplexer 628 to select the appropriate inputs for the averaging mode operation.

However, if an alarm condition occurs, at least one of the $\overline{Q}$ outputs of the flip-flop 647 and 651 will assume a high value. The output of NOR gate 654 will therefore go low providing a low J input to flip-flop 653 and forcing NAND gate 655 to provide a low K input to flip-flop 653. Thus, the Q output of flip-flop 653 goes low at $\overline{RCEP2}$ time, causing multiplexer 628 to provide the instantaneous signals. RCEP1a-1, RCEP3 and RPDO at terminals 628b, 628c and 628a. Alarm circuit 640 thereafter operates under the control of the instantaneous rate signals.

When the alarm conditions no longer exist, it is desirable that the operation of alarm circuit 640 return to the control of the average signals. However, control cannot be returned to the average signals until the beginning of an averaging period as indicated by the RD5 signal. Accordingly, when a no-alarm condition is reassumed, and $\overline{RD5}$ goes low, high level signals are generated to the J and K inputs of flip-flop 653. Thus, when clocked by the $\overline{RCEP2}$ signal, flip-flop 653 toggles causing multiplexer 628 to select the average signals until the next averaged alarm condition.

Provisions are made for display at either the instantaneous or averaged respiration rate. A second multiplexesr 656 receives the same input signals (RCEP1a-1D5, valid RCEP1a, RCEP3D5, RCEP3, RPDO5, RPDO) as multiplexer 628. The respective output terminals are applied to conventional driver circuits which in turn provide an input to a conventional BCD to seven segment converter 657. BCD to seven segment converter 657 drives display 621.

Figure 6K:
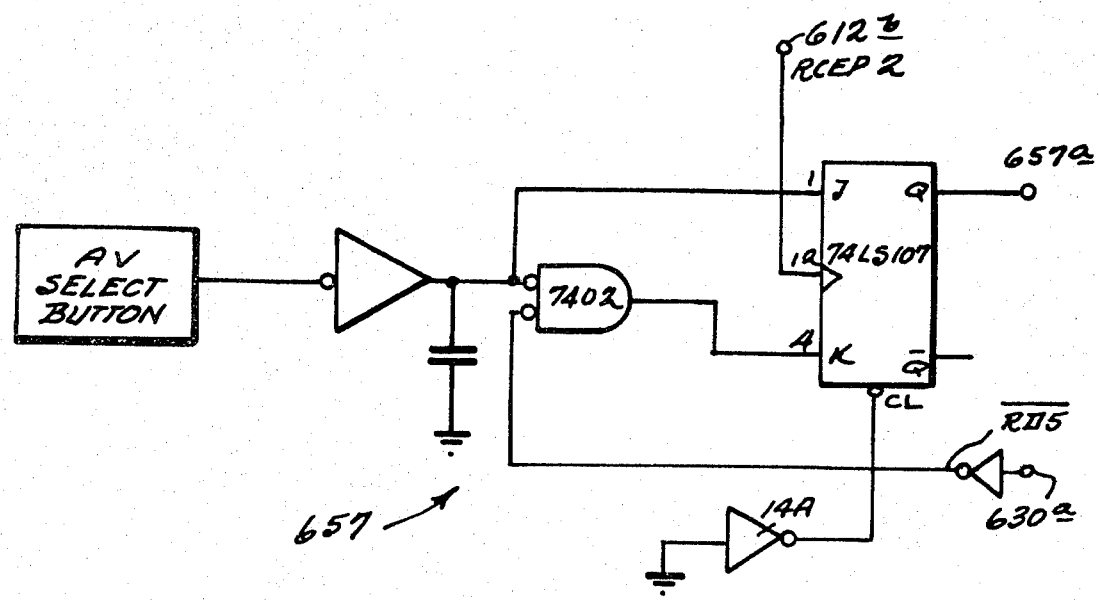
FIG. 6k is a schematic diagram of suitable MUX inhibit logic 651.

Multiplexer 651 is controlled by suitable MUX inhibit logic 657. MUX inhibit logic 657 is responsive to the RD5 signal generated by selective averaging logic 624 at terminal 630a, the RCEP2 signal generated at timing logic output terminal 612b, and to a pushbutton average select switch 658. Suitable MUX inhibit logic is shown in FIG. 6k. MUX inhibit logic 657 operates to ensure that transfer from display of instantaneous to average rates occurs at the beginning of an averaging period. The high down and low up pulses provided at terminals 554a and 556a are also applied to X-ray trigger circuit 700 shown in FIG. 7, to effect maxima and minima triggering, respectively.

As previously noted, it is often necessary that an X-ray picture be taken at a respiration extrema. Automatic triggering of the X-ray machine at the proper instant of time, particularly with respect to a subject incapable of cooperation such as an unconscious adult or an infant is therefore desirable. In addition, a finite time period is required after the application of a trigger signal to the X-ray machine for the actual charging and discharging of the high voltage on the anode which emits the X-rays. The period is a function if, inter alia, exposure time and intensity of the X-ray. Accordingly, it is desirable that the trigger voltage be generted at an instant leading the particular respiration extrema at which triggering is to take place. X-ray triggering circuit 700, in effect, stores a Z count corresponding to the sample occurring just after a chosen one of the high down or low up pulses are generated, and adds or subtracts therefrom a count equivalent to a predetermined amount (through appropriate preloading of the accumulator). Successive samples occurring after the next successive occurrence of the other of the high down or low up pulses are compared to the stored count and the trigger signal generated when the sampled Z counts favorably compare with the stored count. It should be appreciated that the amplitude, slew rate, Z out-of-limites and time domain discrimination are inherent in the X-ray triggering since the X-ray triggering derives from the high down and low up pulses. In addition, it is requisite that the X-ray machine be armed through an operator button, and the respiration rate must be constant within predetermined limits, e.g., varying less than ±20 breaths per minute.

Referring now to FIG. 7, there is shown a suitable maxima X-ray trigger circuit 700. In practice, multiplexing techniques are utilized such that the same circuitry performs both maxima triggering and minima triggering. However, for the sake of clarity, only maxima triggering will be addressed at this point.

Triggering circuit 700 is optically coupled to the X-ray machine through line receiver 702. An arm cycle is initiated when the operator depresses a spring loaded switch associated with the expose control of the X-ray machine. If, at any time prior to actual triggering, the switch is released the arm cycle will be inhibited. Thus, primary control of the X-ray machine is left in the hands of the operator.

When the operator's arm switch is depressed, line receiver 702 generates a high level signal to arm logic 704. Arm logic 704 suitably comprises, in effect, AND gate logic to ensure that, (1) the arm button is depressed, (2) that no alarm condition exists (as will be explained), and (3) that the respiratory waveform period variations are within predetermined limits (e.g., ± a predetermined percentage or equivalent count). The period variation determination is provided by respiratory tachometry circuit 600. Arm logic 704 also includes a synthetic arm provision for testing the triggering apparatus in the absence of a connection to an X-ray machine. Arm logic 704, when enabled, generates an $\overline{arm}$ signal at terminal 704a. The $\overline{arm}$ signal at terminal 704a is applied to the clear (cl) terminals of respective JK flip-flops 714, 718, 728, 730, 746 and 748, each flip-flop having J input tied high and K input tied low. The arm signal at terminal 704a is also applied as one input signal to a conventional 4-input AND gate 742 and is inverted and applied, through a 2-input OR gate 762, to a panel light rearm display 764. Thus, when the arm button is initially depressed and the system is in armed status, per arm logic 704, flip-flops 714, 718, 728, 730, 746 and 748 are initialized to zero.

Flip-flop 714 is clocked by the high down pulse generated at terminal 556a by one-shot 556. The Q output of flip-flop 714 is coupled to one input of a 3-input AND gate 716. The other input terminals of AND gate 716 are responsive to the ZCEP3 (reset) signal generated at terminal 408c of timing logic 408, and the $\overline{Q}$ output of flip-flop 718.

The output of AND gate 716 is coupled to the reset terminal of a 16-bit binary counter 732, to the clock terminal of 'D' flip-flop 730 and, through a delay 722 to the clock terminal of 'D' flip-flop 718. Counter 732 is clocked by the output of a 3-input NAND gate 720.

The inputs of NAND gate 720 are receptive of the Z counts from terminal 436a of digital peak detector 404, the Q output of flip-flop 730 and the $\overline{Q}$ output of flip-flop 728, respectively. The parallel outputs of counter 732 are coupled to one set of input terminals of a magnitude comparator 734. The second set of input terminals at magnitude comparator 734 are coupled to the parallel outputs of a second 16-bit binary counter 738.

Binary counter 738 is clocked by the output of a Q input NAND gate 736. NAND gate 736 is responsive to the Z count signal from terminal 436a of peak detector 404 and to the Q output of flip-flop 728. The clock input of flip-flop 728 is responsive to the output of a 2-input AND gate 726. AND gate 26, in turn, is responsive to the ZCEP2 signal generated at terminal 408b of timing logic 408 and to the Q output of flip-flop 718.

As previously noted, the $\overline{arm}$ signal from arm logic 704 is applied as an input signal to a 4-input AND gate 742. A second input of AND gate 742 is responsive to the outputs of a 2-input AND gate 740. AND gate 740 is responsive to the A less than B (A<B) output signal of magnitude comparator 734 and to the ZCEP1 control signal generated at terminal 408a of timing logic 408. The high down to low up 222 msec. pulse generated by one-shot 562 is responsive to generation of the high down pulse and is inverted by an inverter 744 and applied to a third input of AND gate 742. The fourth input of AND gate 742 is responsive to the Q output of flip-flop 746.

The clock terminal of flip-flop 746 is coupled to the output of a 2-input NAND gate 748. The inputs of NAND 748 are the low up pulses generated by one-shot 554 at terminal 554a and the Q output of flip-flop 714. The output of NAND gate 742 is applied to one input terminal of a further 3-input NAND gate 756. The other inputs of NAND gate 756 are responsive to the inverted (through inverter 754) output signal of a shift register 752 and to the $\overline{Q}$ output of JK flip-flop 748. Flip-flop 748 is clocked by the output of AND gate 756. The Q output of flip-flop 748 is coupled to a display lamp "exposed" on the indicator panel. Flip-flop 748 is initially cleared by the $\overline{arm}$ signal. Thus, when a trigger signal is generated, the Q output goes high to activate the "exposed" indicator and the $\overline{Q}$ output goes low, thereby inhibiting generation of additional trigger pulses. Shift register 752 is responsive to the high down pulse and is generated by one-shot 556 at terminal 556a. The output of shift register 752 is also applied as the second input to OR gate 762 to drive the rearm indicator 764. The output of NAND gate 756 is applied to a line driver 450 to optically couple a trigger signal to the X-ray unit.

In operation, assuming the system to be in armed status, when the operator depresses the arm button, the next successive high down pulse clocks flip-flop 714. The Q output assumes a high state upon the falling edge of the pulse. Recalling that flip-flop 718 was initially cleared, NAND gate 716 thus generates a high level pulse upon the next occurrence of control signal ZCEP3 (reset) from timing logic 408. The pulse generated by AND gate 716 resets counter 732.

Counter 732 is preloaded with a count corresponding to 0.3 ohms. The preloading of the count equivalent to 0.3 ohms, in effect, adds the count equivalent to 0.3 ohms to the Z count at the high down instant, to account for the resolution of the system. As previously explained, the high down (or low up) pulses are generted a maximum of 0.3 ohms after the occurrence of the peak. Thus, by adding the preload count to counter 732, the stored value corresponds to a point on the respiration waveform just preceding the inspiration maxima.

The ZCEP3 pulse gated by AND gate 716 also clocks flip-flop 730, and upon the negative going transition of the pulse a high level Q output signal is generted to NAND gate 720. Recalling that flip-flop 728 was initially cleared, counter 732 thus accumulates the ΔZ count associated with the sample immediately after the high down point. It should be appreciated that in view of storing the sample count occurring just subsequent to the high down point, the A less than B signal will be generted slightly before the maxima. Thus, time is provided for the X-ray machine to fire after generation of the trigger signal.

After the delay by delay 722, flip-flop 728 is also clocked and AND gate 726 enabled with respect to the next successive ZCEP2 (load) signal generated by timing logic 408 (terminal 408b). Flip-flop 728 is thus set, inhibiting NAND gate 720 and enabling NAND gate 736. Accordingly, counter 738 accumulates the Z count of the next sample. The count in counter 738 is compared to the count in counter 732 by comparator 734. Counter 738 is thereafter reset by the ZCEP3 pulse generated at terminal 408c of timing logic 408 in preparation for accumulation of the next sample Z count.

In effect, each successive sample is compared to the count stored in accumulator 732 until the respiratory waveform reaches the point corresponding to the stored count in the next respiratory cycle. When counter 738 accumulates a count greater than the count stored in counter 732 a signal is generated to enable AND gate 740 with respect to the ZCEP1 timing signal (generated at terminal 408a of timing logic 408). Assuming that the output pulse from AND gate 740 is not generated during the high down to low up period (as determined by one-shot 562a), and that a low up pulse has occurred during the interum (as determined by NAND gte 748 and flip-flop 746), a signal is generated to NAND gate 756. NAND gate 756 is enabled to trigger the X-ray pulse through line driver 450 if the X-ray has not previously been exposed (as determined by JK flip-flop 748), and no more than a predetermined number (e.g., 5 breaths) have passed since the initial arming of the system (as determined by shift register 752). However, once shift register 752 has indicated that 5 successive breaths have passed during the arm sequence, or flip-flop 748 has indicated that the X-ray film is exposed (i.e., the picture has already been taken), AND gate 756 is inhibited until such time as the system is rearmed. Thus, only a single X-ray picture will be taken during the course of an arm sequence irrespective of the arm button being depressed for a length of time after the X-ray has been taken. Further, an indication of a malfunction is provided if 5 breaths pass without a triggering, and rearming of the system is required.

Minima triggering would be established in a similar manner. However, the low up pulse generated at terminal 554a would be applied as a clock to flip-flop 714 and to shift register 754. Similarly, the high down signal generated at terminal 556a would be applied to AND gate 748, and the low up to high down one-shot pulse generated at terminal 558a would be applied through inverter 744 to AND gate 742. In addition, counter 738, rather than counter 732, would be preset with the count equivalent to 0.3 ohms. In practice, the 0.3 ohm preload is hardwired into counter 732 and a count equivalent to 0.6 ohms selectively preloaded into counter 738 through the multiplexers. The effect of the 0.6 ohm preload is to offset the hardwired 0.3 ohm preload in counter 732 and substract and additional 0.3 ohms from the count stored in counter 732 (effected during the comparison).

As previously noted, preamplifier 200 generates an analog signal indicative of the biopotential of the myocardia, commonly referred to as an ECG signal. The ECG signal is differentially provided at terminals 238a and 238b. A rate analysis similar to that performed on respiration is made on the ECG signal.

Figure 8:
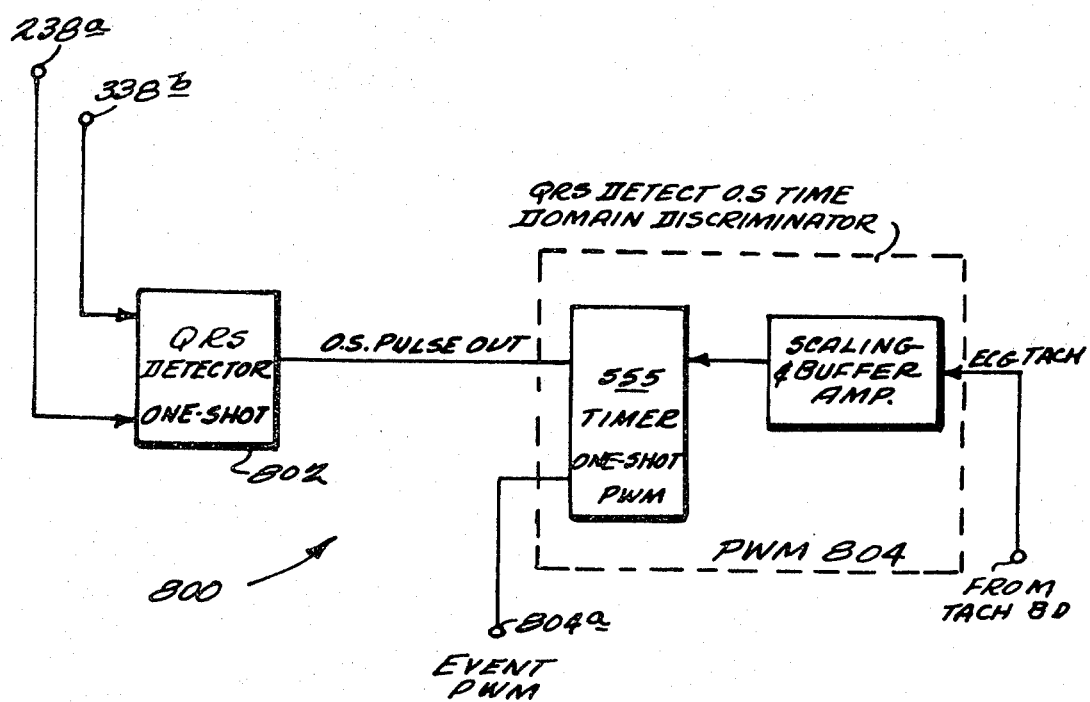
FIG. 8 is a block diagram of suitable cardiac analog processing circuit 800.

The ECG signal is applied to an ECG analog processing circuit 800 comprising a conventional QRS detector one-shot and time domain discrimination circuitry. ECG analog processing circuit 800 is shown in FIG. 8. The ECG signal provided at preamplifier output terminals 238a and 238b is applied to a conventional QRS detector one-shot 802. QRS detector 802 provides a 240 msec. pulse in response to each QRS complex. The QRS detector pulse train is applied to a pulse width modulator 84. Pulse width modulator 804 generates an output pulse at terminal 804a having a pulse width inversely related to the instantaneous heart rate. Pulse width modulator 804 comprises a 555 timer integrated circuit responsive to an analog signal indicative of the heart rte derived, as will be explained, from cardio-tachometry circuit 900.

Figure 9:
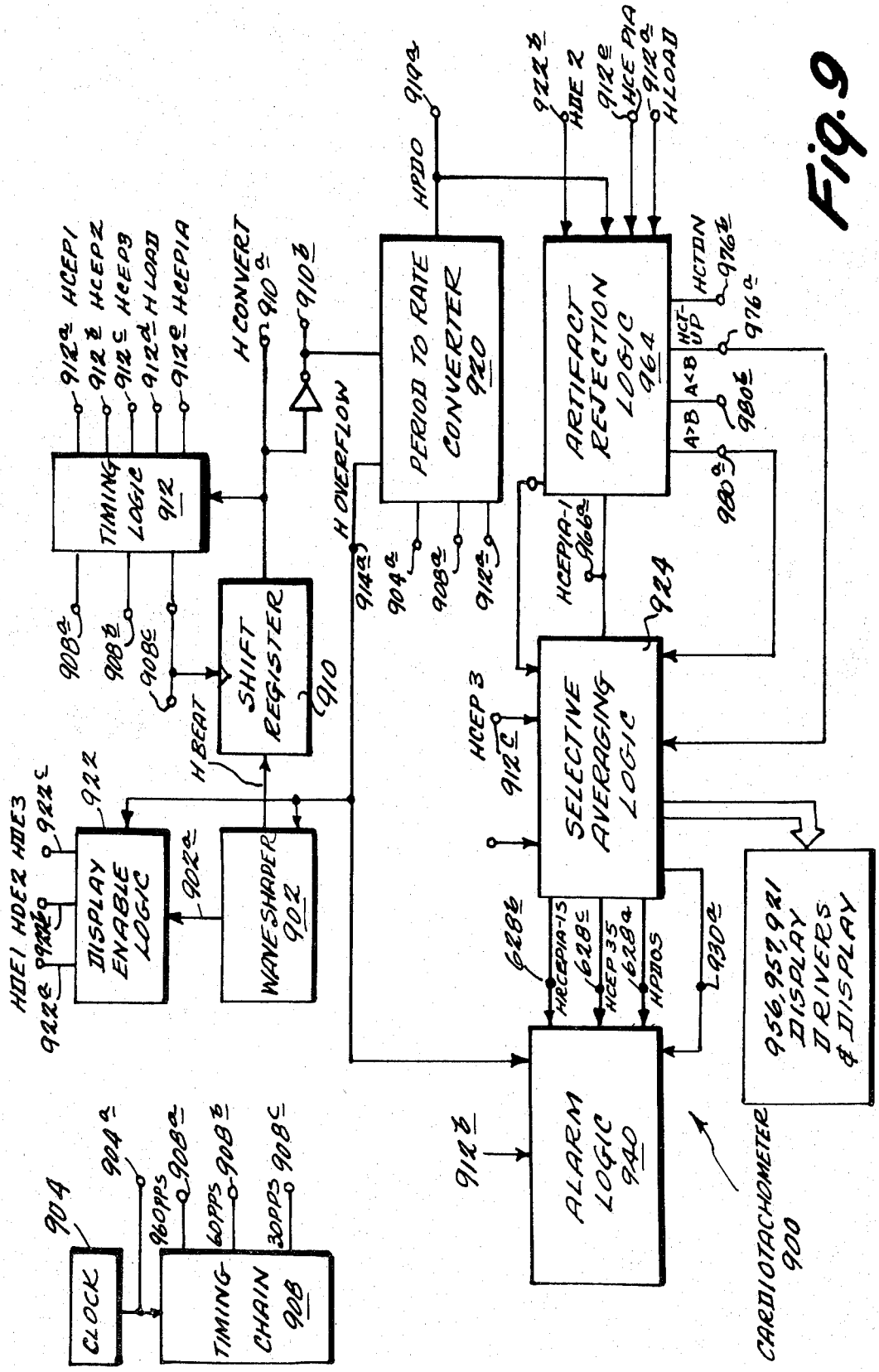
FIG. 9 is a block diagram of cardiotachometer 900.

The pulse width modulated signal is applied to cardio-tachometry circuit 900 shown in block diagram form in FIG. 9. Cardio-tachometry circuit 900 is substantially identical to the respiration tachometry circuit 600 except that the timing chain 908 (analogous to timing chain 608) generates respective output signals at twice the rate of the analogous signals in respiration tachometry circuit 600: 960 pps (used instead of 480 pps), 60 pps (used instead of 30 pps), and 30 pps (used instead of 15 pps). Further, the convert period generated by a shift register 910 analogous to shift register 610 is 33 msec. in length, rather than 66 msec. as in the respiration tachometry circuit 600. The preload count in the binary counter in a period to rate converter 920, corresponding to counter 614 in period to rate converter 620 of respiration tachometry circuit 600 therefore differs accordingly. In addition, the averaging function provided by selective averaging logic 924 analogous to selective averaging logic 624 provides for averaging over 10 heart beats rather than 5 breaths as in respiration tachometry circuit 600. Accordingly, the counters corresponding to counters 626 and 630 are divide-by-10 counters rather than dividie-by-5 counters. In addition, in the circuit 964 corresponding to artifact rejection circuit 664 components corresponding to AND gate 694 would be deleted such that the components corresponding to OR gate 671 is responsive to two input signals, A less than B and force (from the magnitude comparator and shift register). Thus, heart rate counts differing by ±20 beats per minute from the base rate are rejected. The output of the D/A converter responsive to the outputs of the latches corresponding to latches 662 in artifact rejection circuit 664 is utilized as the analog heart rate signal to time domain discrimination pulse width modulator 804.

It will be understood that when an element of the cardio-tachometry circuit 900 is hereinafter referred to, the designation will be the last two digits of the corresponding element of respiration tachometry circuit 600 prefaced with a 9 rather than 6. For example, the counter in cardio-tachometry circuit 900 corresponding to counter 660 of respiration tachometry circuit 600 will hereinafter be referred to as counter 960 and so forth. Similarly, analogous control signals in cardio-tachometry circuit 900 will be designated by the prefix H, replacing the R used with respect to tachometry circuit 600. For example, the signal in cardio-tachometry circuit 900 analogous to the signal RCEP1 will be designated HCEP1, and so forth.

As previously noted, monitor 100 generates an apnea alarm in response to a number of different detected conditions. An alarm is generated if the respiration period extends beyond a predetermined length, as detected by the generation of the signal R overflow by period counter 614 at terminal 614a. It should be appreciated that other bits of counter 614 besides the most significant bit, can be used to initiate an alarm. In the preferred embodiment, an alarm is generated if the respiration period exceeds 16 seconds. A similar alarm is provided in cardio-tachometry circuit 900 with respect to heart beat rate. The alarm is generated if the heart beat period exceeds 1.8 seconds.

An apnea alarm is generated if a physiological apnea occurs, that is, if the respiration period doubles in successive samples and four successive heart beat decelerations are detected. Physiological apnea detector 1000 will be hereinafter more fully described in conjunction with FIG. 10.

Referring now to FIG. 10a, circuit 1000 utilizes two identical banks of calculation apparatus, bank A and bank B. Calculation apparatus bank A comprises a preloaded (16 counts) binary counter 1002a, a preloaded (8) binary counter 1004a, a divide-by-2 counter 1006a, a magnitude comparator 1008a, and two 2-input AND gates 1010a and 1020a. Divide-by-2 counter 1006a is coupled to the clock input of binary counter 1004a. One input of 2-input AND gate 1010a is coupled to the A>B output of magnitude comparator 1-08a, and one input of 2-input AND gate 1020a is coupled to the A<B output of comparator 1008a.

Calculation apparatus bank B is essentially identical to calculation apparatus bank B and comprises a preloaded (16) binary counter 1002b, a preloaded (8) counter 1004b, a divide-by-2 counter 1006b, a magnitude comparator 1008b, and 2-input gates 1010b and 1020b.

Figure 10B:
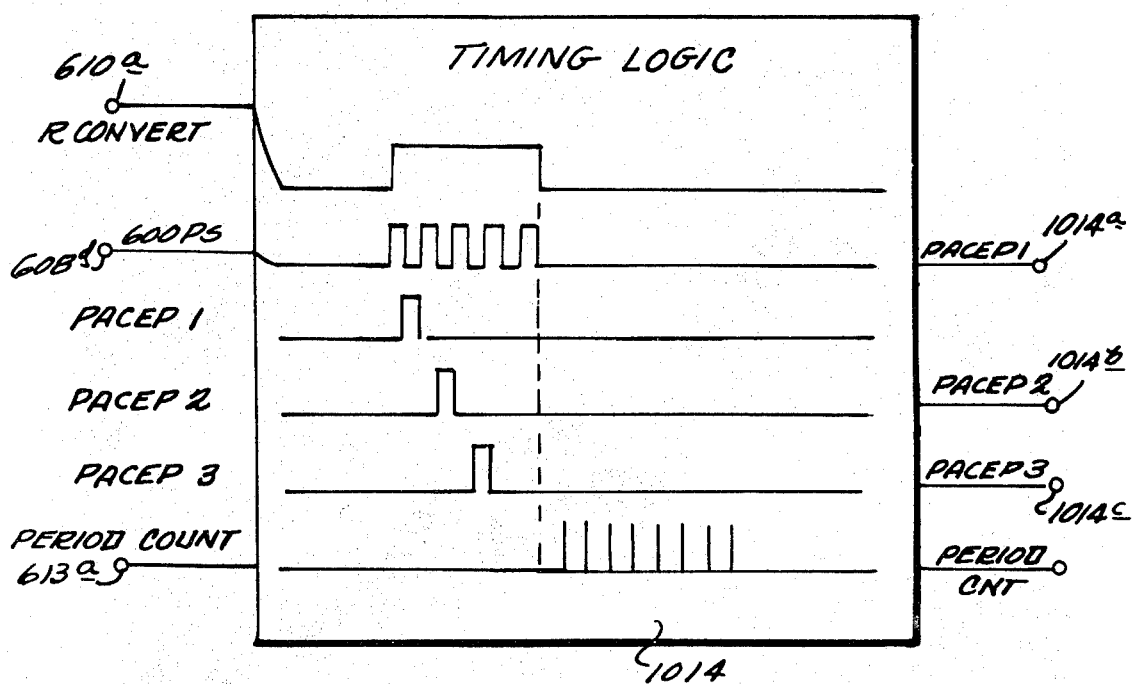
Figure 10C:
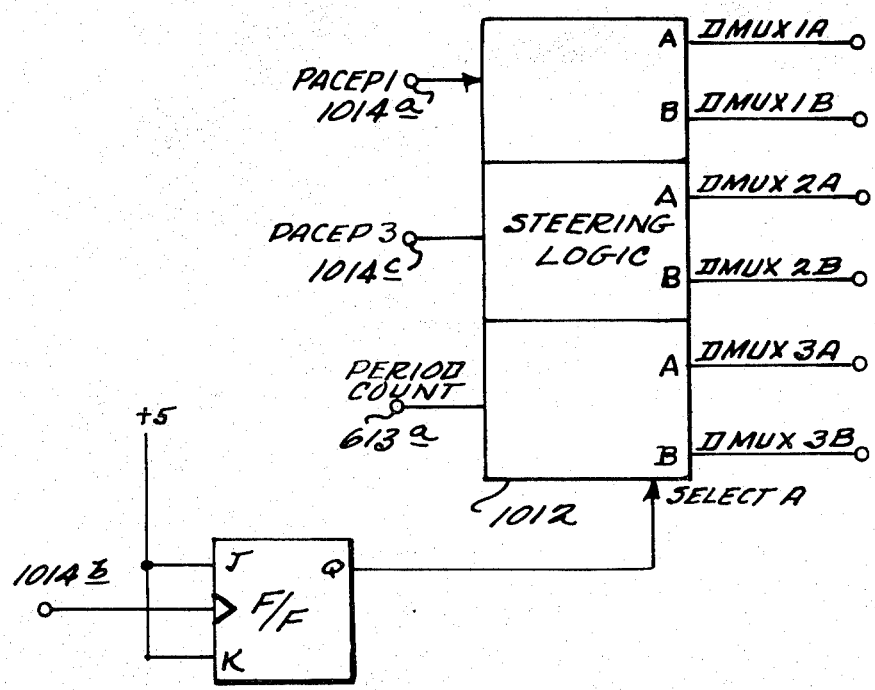

In operation, suitable timing logic 1014, illustrated diagrammatically in FIG. 10b, generates three sequential timing signals, PACEP1a on terminal 1014a, PACEP2 on terminal 1014b and PACEP3 on output terminal 1014c. Suitable steering logic 1012 (shown diagrammatically in FIG. 6c) alternately applies control signals generated by timing logic 1014 to the respective calculation apparatus banks A and B such that the period count is accumulated in the respective counter 1002 of a first bank during a first cycle, and such that during the next cycle, the period counts are applied through the respective divider 1006 to the respective binary counter 1004 of the first bank, while the period count is simultaneously accumulated in the binary counter 1002 of the other bank.

For example, assuming bank A to be initially addressed, steering logic 1012 provides the timing signals at the A output terminals thereof. A first period count would be accumulated in binary counter 1002a. The next period count generated would be applied simultaneously through divider 1006a to binary counter 1004a and to binary counter 1002b. Thus, at the end of the second count, binary counter 1002a contains a first period count and binary counter 1004a contains ½ of the second period count and counter 1002b contains the second period count.

The contents of binary counters 1002a and 1004a are compared by magnitude comparator 1008a. If the contents of counter 1004a (½ the second period count) are greater than the previous count contained in counter 1002a, the second period is twice the duration of the preceding period. Accordingly, the A greater than B signal enables AND gate 1010a with respect to a PACEP1 timing pulse generated by timing logic 1014 provided at steering logic terminal DMUX1a. The PACEP1 pulse is gated through an OR gate 1016 to clock a D flip-flop 1018. The D input of flip-flop 1018 is tied high, and accordingly, a high level Q output is provided. If A is less than B, that is, the second period count is not twice the previous period count, AND gate 1020a is enabled with respect to the PACEP1 pulse (provided at steering logic terminal DMUX1a) to clear flip-flop 1018.

In the next cycle, steering logic 1012, in effect toggles, providing the control signals on the B output terminals thereof to reverse the roles of calculation apparatus bank A and calculation apparatus bank B. Accordingly, the period count is applied through divide-by-2 counter 1006b to binary counter 1004b and is simultaneously accumulated in binary counter 1002a. Thus, at the end of the conversion, counter 1002b contains the previous period count, counter 1004b contains ½ of the instantaneous period count, and counter 1002a contains the instantaneous period count. The contents of counters 1002b and 1004b are compared by comparator 1008b and the A greater than B or A less than B signals generated accordingly.

As previously noted, when an A>B signal is generated, flip-flop 1018 assumes a high level Q output. The Q output is applied to a 1 μsec. one-shot 1026, initiating circuitry for detection of four successive decelerations in heart rate. Recalling that the up/down control flip-flop 976 for the up/down counter 972 in the artifact rejection portion 964 of cardiotachometer 900 provides an indication of whether the heart rate has increased or decreased with respect to the previous period, a high Hcountup (Q) signal, supplied at terminal 976a, is indicative of an increased heart rate. Similarly, in Hcountdown signal ($\overline{Q}$), supplied at terminal 976b is indicative of a decreased heart rate. Accordingly, the Hcountup signal (976a) is gated in an AND gate 1028 with the HCEP1a-1 signal (indicative of a valid rate count) provided at terminal 966a in the cardio-tachometer 900 and the gated signal applied along with the output of one-shot 1026 to the respective inputs of a 2-input NOR gate 1030. The output of NOR gate 1030 is coupled to the reset terminal of a shift register 1032. NOR gate 1030 generates a low level signal in response to a high level signal from either one-shot 1026 or AND gate 1028.

In operation, the one-shot pulse triggered by the Q output of flip-flop 1018 initially resets shift register 1032. Shift register 1032 is clocked by the output of a 2-input AND gate 1034 which gates the Hcountdown signal from terminal 976b of cardio-tachometer 900 with the HCEP1a-1 (valid rate count) signal from terminal 966a. Thus, shift register 1032 is indexed by each decreasing heart rate sample. However, shift register 1032 is reset in response to a high level output from AND gate 1028 generated in response to an increasing heart rate (Hcountup). Thus, if four decreasing heart rate samples occur without an intervening increasing heart rate sample shift register 1032 generates at its QD output a high level signal which is applied, along with the Q output of flip-flop 1018 to a 2-input AND gate 1036. The output of NAND gate 1036 is applied as a clock input to a D flip-flop 1038. The D input of flip-flop 1038 is tied high, and the Q output is tied to one input of a 2-input OR gate 1040. The other input of OR gate 1040 is responsive to the R overflow signal from period counter terminal 614a (respiration tachometry circuit 600). Accordingly, OR gate 1040 generates a high level signal if a respiration period is twice the duration of the preceding period and four valid decreasing heart beat samples are detected or if the period counter 614 overflows indicating a period beyond the maximum threshold. The high output of OR gate 1014 initiates an apnea alarm.

As noted above, an apnea alarm is also generated as a fail-safe, in the event that the detected heart rate and respiration rate are approximately equal for a predetermined number of successive samples. This condition is detected by cardiac component detection sensor circuit 1100 and will now be described more fully in conjunction with FIG. 11. In general, sensor 1100 captures an RPDO count indicative of the respiration rate in breaths per minute and compares it to an HPDO, the analogous numerical number equivalent to the heart rate in beats per minute. However, the RPDO counts and HPDO counts are asynchronous data. Accordingly, an RPDO count is captured at random and held, then counted down using timing derived from cardiotach 900. The captured RPDP count is counted down with the next successively occurring HPDO and if more than four successive differences are within a predetermined limit, an alarm is generated.

Figure 11A:
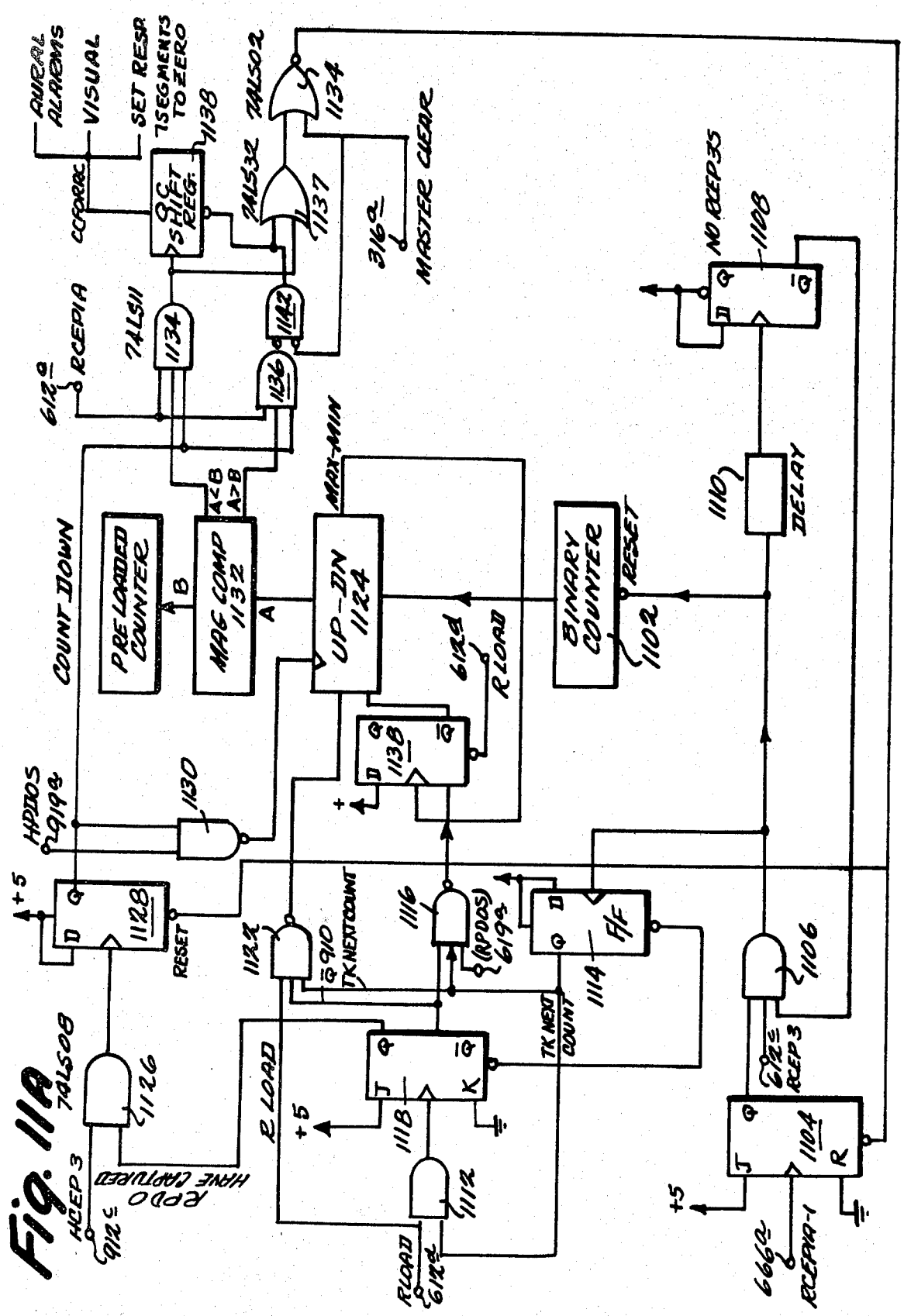
FIG. 11a is a block schematic diagram of cardiac component detection sensor 1100.
Figure 11B:
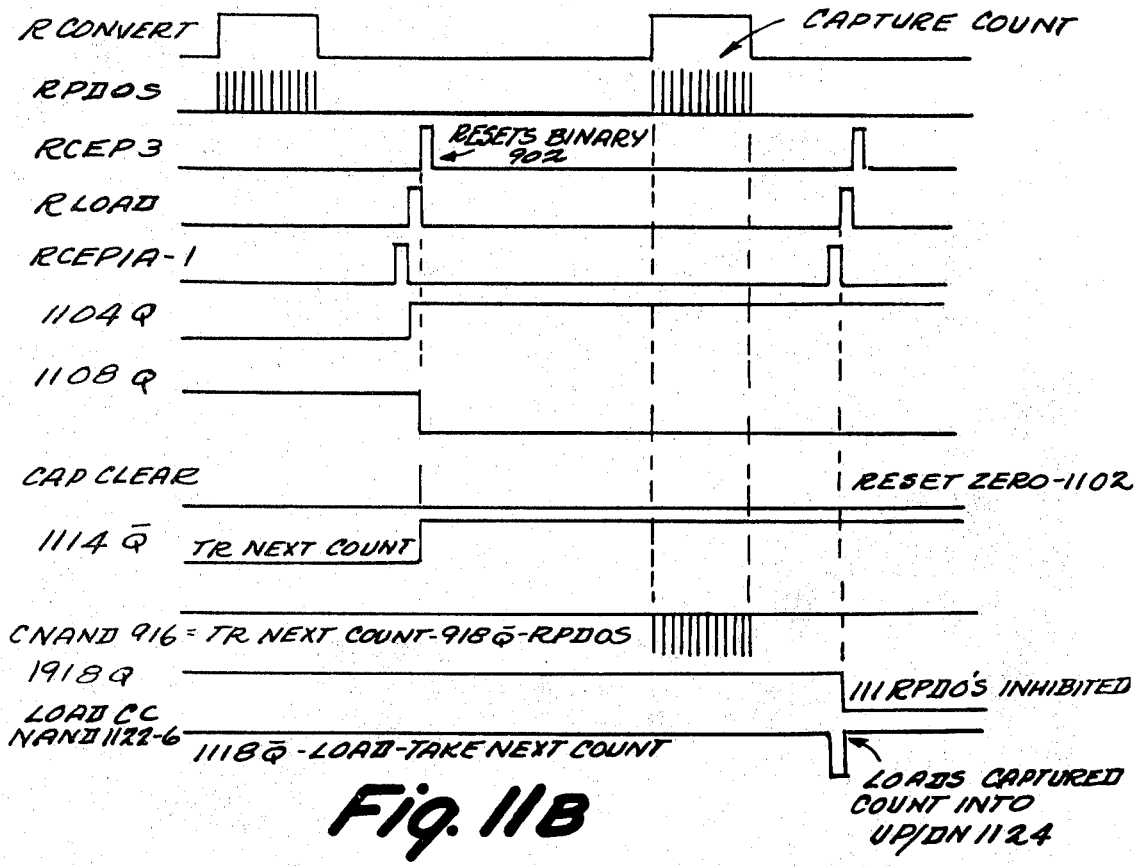
FIGS. 11b and 11c are timing diagrams relating to cardiac component sensor 1100.
Figure 11C:
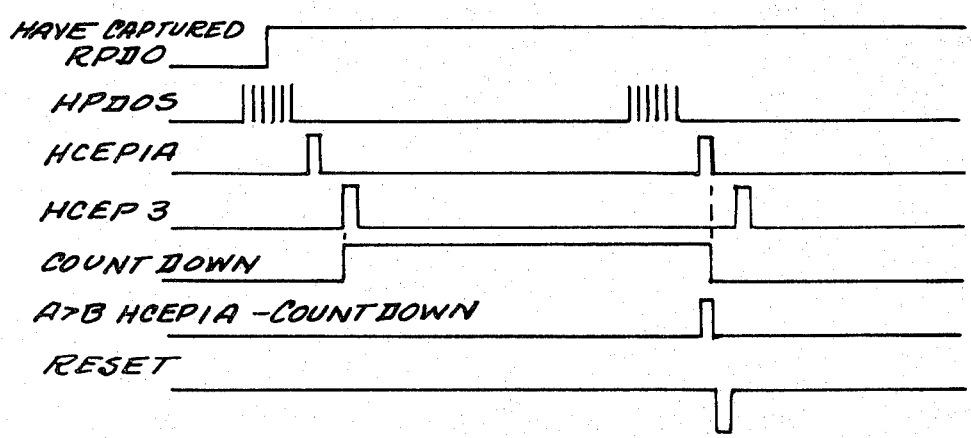

Referring now to FIG. 11a, the RPDO signals from period to rate converter 620 (terminal 619a) are applied to one input of a 3-input NAND gate 1116, the output of which is applied as a clock input to an 8-bit binary counter 1102. The parallel outputs of counter 1102 are applied to the inputs of an up/down counter 1124, the parallel outputs of which are inturn coupled to a first set of inputs of a magnitude comparator 1132. The second set of inputs to comparator 1132 have applied a hardwired preloaded count corresponding to the desired limit. The max/min output of up/down counter 1124 (indicative of the counter attaining a zero count) is applied to clock an up/down control flip-flop 1138 in a manner similar to the cooperation between up/down counter 672 and flip-flop 676 in artifact rejection circuit 664 (respiration tachometry circuit 600).

Another input of NAND gate 1116 is responsive to the $\overline{Q}$ output of a JK flip-flop 1118. The J and K inputs of flip-flop 1118 are respectively tied high and to ground. JK flip-flop 1118 is clocked by the output signal of a 2-input AND gate 1112. AND gate 1112 is responsive to the Rload signal generated at timing logic output terminal 612d and to the Q output of D flip-flop 1114. The third input of NAND gate 1116 is also responsive to the Q output of flip-flop 1114. The D input of flip-flop 1114 is tied high. Flip-flop 1114 is clocked and binary counter 1102 reset in response to a signal generated by a 3-input AND gate 1106.

AND gate 1106 is responsive to the RCEP signals generated at timing logic output terminal 612c, to the Q input of JK flip-flop 1104 and to the $\overline{Q}$ output of a D flip-flop 1108. JK flip-flop 1104 has J and K input tied high and to ground, respectively, and is clocked by the RCEP1a-1 signal generated by artifact rejection circuit 664 at terminal 666a. It should be recalled that the RCEP1a-1 signal is indicative of the accumulation of a valid rate count. D flip-flop 1108 has D input tied high and is clocked by the output signal of AND gate 1106, delayed by a predetermined delay 1110. The $\overline{Q}$ output of flip-flop 1118, the Q input of flip-flop 1114 and the Rload signal generated at timing logic output terminal 316d are applied to the respective inputs of a 3-input NAND gate 1122. The output of NAND gate 1122 is applied to the reset terminal of up/down counter 1124.

The Q output of flip-flop 1118 is also applied to one input of a 2-input AND gate 1126. The other input of AND gate 1126 is the HCEP3 signal generated at the cardio-tachometry timing logic output terminal 912c. The output of AND gate 1106 is applied to the clock input of a D flip-flop 1128.

The D input of flip-flop 1128 is tied high. The Q output of D flip-flop 1128 is applied to one input of a 2-input NOR gate 1130 and to one input of each of 3-input AND gates 1134 and 1136. The other input of NAND gate 1130 is the HPDO counts from the cardio-tachometry circuit period to rate converter input terminal 919a.

Second input terminals of each of AND gates 1134 and 1136 are responsive to the RCEP1a signal generated at respiration tachometry circuit timing logic output terminal 612e. The third terminals of AND gates 1134 and 1136 are respectively responsive to the A<B and A>B output signals of magnitude comparator 1132. The output of AND gate 1134 is applied as the clock signal to a shift register 1138. The QC output (corresponding to the third bit) of shift register 1138 provides an activation signal for respective audio/visual alarms) and is used to set the respiration display to zero.

The output of AND gate 1136 is applied to one input of a 2-input NOR gate 1142. The other input to NOR gate 1142 is the master clear signal generated at terminal 316a of analog processing circuit 300 (FIG. 3a). The output of NOR gate 1142 is applied as a clear signal to shift register 1138 and to one input of a 2-input OR gate 1137. The other input of OR gate 1137 is responsive to the output of AND gate 1134. The output of NOR gate 1137 is applied to one input of a 2-input NOR gate 1139, the other input of which is responsive to the master clear signal from terminal 316a. The output of NOR gate 1134 (hereinafter designated reset) is applied as a reset signal to flip-flops 1104, 1108, 1114, 1118 and 1128.

In operation, the circuit initialized in response to the master clear signal, and the respective flip-flops of circuit 1100 reset. When RCEP1a-1, indicative of the accumulation of a valid respiratory count is generated, flip-flop 1104 generates a high level Q signal. Accordingly, since D flip-flop 1108 is initially reset, AND gate 1106 is enabled with respect to the next occurring RCEP3 pulse. Accordingly, binary counter 1102 is cleared and flip-flop 1114 set.

The high level Q output of flip-flop 1114 enables NAND gates 1116 and 1122, (since flip-flop 1118 is initially reset) with respect to the RPDO signal and Rload signal, respectively. The high Q output from flip-flop 1114 also enables AND gate 1112 with respect to the next occurring Rload signal. Accordingly, the next occurring Rload signal clocks JK flip-flop 1118, causing the Q output to assume a high level and the $\overline{Q}$ output a low level at the falling edge of the Rload pulse. NAND gates 1116 and 1122 are thus inhibited at the falling edge of the Rload pulse. The RPDO counts are, however, accumulated in binary counter 1102 during the interum between the RCEP3 pulse and the occurrence of the Rload pulse. The Rload pulse, in effect, causes up/down counter 1124 to be loaded with the contents of binary counter 1102.

On the falling edge of Rload, AND gate 1126 is enabled with respect to the HCEP3 signal. Accordingly, the next successive HCEP3 signal clocks D flip-flop 1128 to initiate a down count operation. The high Q output of flip-flop 1128 enables AND gate 1130, causing the HPDO counts (indicative of heart rate) to count down up/down counter 1124. At the end of the count down sequence, the contents of up/down counter 1124 represent the difference between the heart rate and respiration rate.

The difference count is then compared to the preloaded threshold (e.g., 4) by magnitude comparator 1132. If the difference is greater than the preloaded count, the A>B signal enables AND gate 1136 with respect to the RCEP1a signal, causing NOR gate 1142 to generate a low level signal to reset shift register 1138. Conversely, if the difference is less than the preloaded count, the A<B signal from comparator 1132 enables AND gate 1134 with respect to the RCEP1a signal causing shift register 1138 to be indexed. The passage of the RCEP1a pulse by either AND gates 1134 or 1136 effects a reinitialization of the system in readiness for the next respiration rate count.

If three successive comparisons results in A<B signals, without an intervening A>B comparison, shift register 1138 actuates an alarm. The respective signals associated with circuit 1100 are illustrated in timed relation in FIGS. 11b and 11c.

Figure 12:
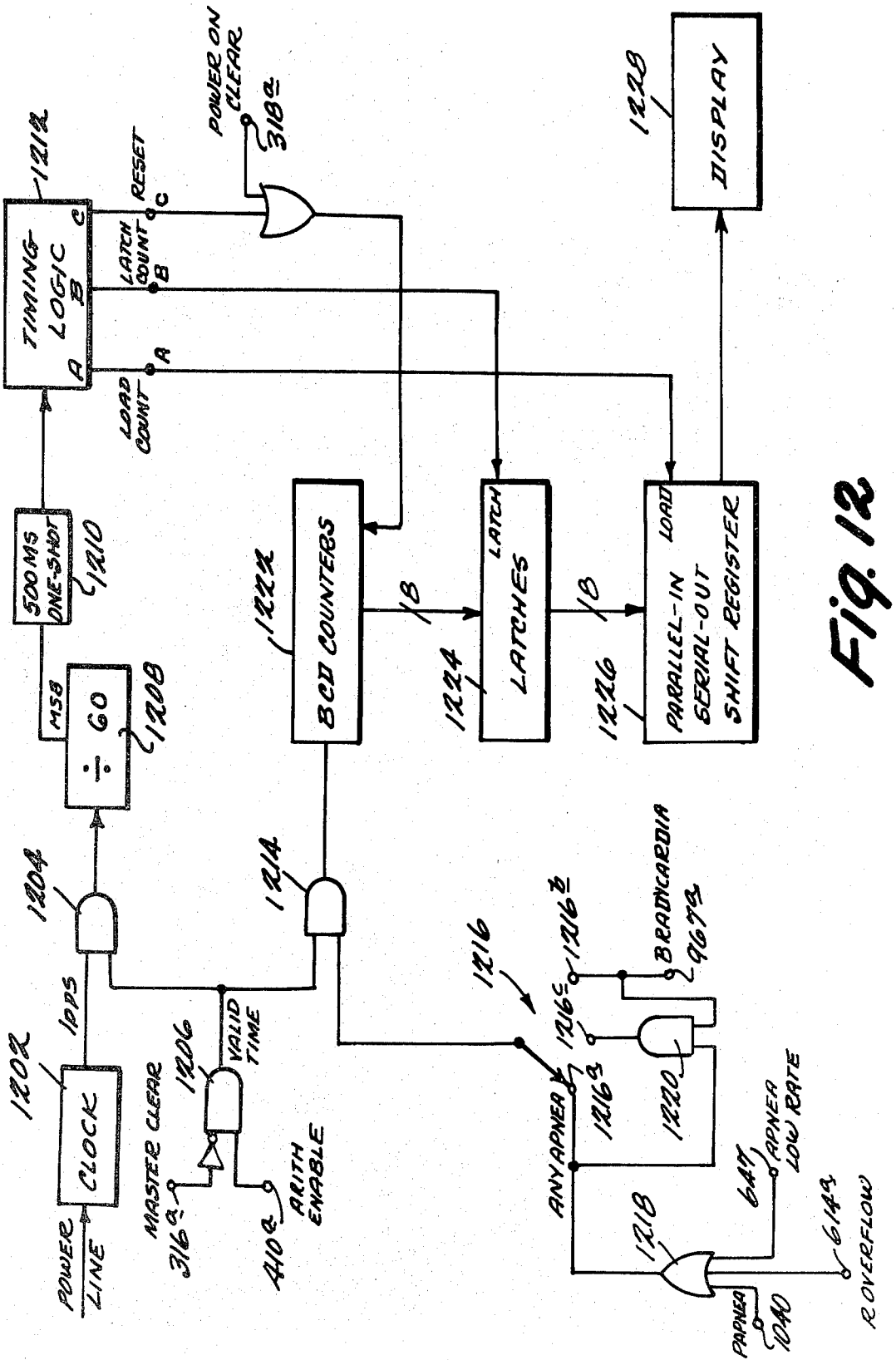
FIG. 12 is a block schematic of apneic episode counter 1200.

As previously noted, it is desirable to determine the number of apneic episodes occurring during a given time period. A circuit 1200 for providing an indication of apneic episodes per unit time is shown in FIG. 12. A clock 1202 operating from and in synchronism with the power line signal generates a one pulse per second signal. The one pulse per second signal is applied to a 2-input AND gate 1204.

AND gate 1204 gates the one pulse per second signal with the output (valid time) of a 2-input AND gate 1206. AND gate 1206 is responsive to the master clear signal from terminal 316a and the arithmetic enable signal from terminal 410a. The output of AND gate 1206 provides an indication of the actual time during which a valid monitoring of the subject is provided by monitor 100. The output of AND gate 1204 is applied to a divide-by-60 BCD counter chain 1208. The most significant bit of divide-by-60 counter chain 1208 is applied to a 500 msec. one-shot 1210.

The one-shot pulse is applied to suitable timing logic 1212. Timing logic 1212 generates a response to the one-shot pulse three sequential output signals, in sequence: load count, latch count and reset.

The valid time signal is also applied to one input of a 2-input AND gate 1214. The other input of AND gate 1214 is connected to a rotary switch 1216 which selectively couples the input to one of three terminals, 1216a, 1216b and 1216c. Terminal 1216a provides an indication of an apnea generated by a 3-input OR gate 1218. OR gate 1218 is responsive to the physical apnea signal from OR gate 1040, the R overflow signal provided at terminal 614a and the apnea/low rate indication provided by the Q output of flip-flop 647. Terminal 1216b is connected to terminal 967a to provide an indication of bradycardia. Terminal 1216c provides an indication of any apnea and bradycardia by coupling the respective terminals 1216a and 1216b to the respective inputs of a AND gate 1220. Thus, AND gate 1214 provides a pulse in response to any occurrence during valid monitoring time of the event chosen by switch 1216.

The output of AND gate 1214 is applied as a clock input to a BCD counter 1222. The parallel outputs of BCD counter 1222 is coupled to a register of latches 1224, the parallel outputs of which are inturn coupled to a parallel-in-serial-out shift register 1226. The output of shift register 1226 is applied to a seven segment display 1228. BCD counters 1222 accumulate a count representative of the number of occurrences of the chosen event.

In operation, in response to the 500 msec. one-shot pulse, timing logic 1212 generates control signals to cause shift register 1226 to be loaded with the contents of latches 1224. Latches 1224 are then updated with the contents of BCD counters 1222. Counters 1222 are then reset for accumulation of the number of events occurring during the next period of time.

It should be understood that the above description is of illustrative embodiments of the present invention, and that the invention is not limited to the specific form shown. Various modifications can be made in the design and arrangement of the elements as will be apparent to those skilled in the art without departing from the scope of the invention as expressed in the appended claims.

I claim:

1. Apparatus for generating a triggering signal to an X-ray machine comprising:
    operator actuated means for selectively generating an ARM signal indicative of a desired armed condition;
    means for generating an analog respiration signal directly representative of the respiration of a subject;
    means, responsive to said analog respiration signal, for periodically sampling said analog respiration signal and generating sample indicative of said samples;
    amplitude discriminator means, responsive to said sample signal, for generating a signal indicative of the difference between the instantaneous sample and a mean sample, said mean sample being the last preceding sample differing from the preceding mean sample by a predetermined value;
    means, cooperating with said amplitude discriminator means for generating a signal change signal indicative of a change in sign of said difference in a predetermined direction;
    means for storing indicia of the modified value of the next successive sample occurring after generation of said sign change signal, the value of said next successive value being modified by said predetermined value;
    time discriminator means, responsive to said sign change signal, for generating an extrema signal, said time discriminator means including means for inhibiting generation of said extrema signal in response to sign change signals within a prescribed time period after a preceding sign change signal, said first prescribed time period being in accordance with the maximum rate of physiological respiration of said subject;
    means, responsive to said extrema signal, for generating a signal indicative of a second prescribed time period after generation of said extrema signal, said second prescribed period being in accordance with the inspiratory to expiratory action of said subject;
    means, responsive to said sample signal and a signal indicative of said stored indicia of modified value, for generating an actuation signal when the value of the instantaneous sample approximately equals said modified value; and
    logic means, responsive to said actuation signal, for selectively generating, if not inhibited, said triggering signal;
    first inhibit means, responsive to said arm signal, for inhibiting said logic means with respect to any actuation signal generated in the absence of said desired armed condition; and
    second inhibit means, responsive to said signal indicative of said second prescribed period, for inhibiting said logic means with respect to any actuation signal generated during said second prescribed time period after generation of a preceding sign change signal.

2. The apparatus of claim 1 further including:
    means, cooperating with said amplitude discrimination means, for generating an anti-sign change signal, indicative of a change in sign of said difference in a direction opposite to said predetermined direction; and
    third inhibit means, responsive to said anti-sign change signal, for inhibiting said logic means with respect to any actuation signal having been generated in response to an instantaneous sample approximately equalling the modified value of the next successive sample after generation of a sign change signal where said instantaneous sample occurs after generation of said sign change signal without generation of an intervening anti-sign change signal.

3. The apparatus of claims 1 or 2 further including:
    breath counter means, responsive to said sign change signal, for generating an output signal indicative of the passing of a predetermined number of respiratory cycles after initial generation of said arm signal; and
    fourth inhibit means, responsive to said breath counter means output signal for inhibiting said logic means with respect to actuation signals generated after the passing of said predetermined number of respiratory cycles after initial generation of said arm signal, until next generation of said arm signal.

4. The apparatus of claims 1 or 2 further including:
    fifth inhibit means, responsive to said arm signal and said trigger signal, for inhibiting said logic means with respect to actuation signals generated after generation of a trigger signal until the next regeneration of said arm signal.

5. The apparatus of claim 3 further including:

fifth inhibit means, responsive to said arm signal and said trigger signal, for inhibiting said logic means with respect to actuation signals generated after generation of a trigger signal until the next regeneration of said arm signal.

6. The apparatus of claim 4 further including means cooperating with said fifth inhibit means for providing an display indicia of exposure upon generation of said trigger signal until the next regeneration of said arm signal.

7. The apparatus of claim 5 further including means cooperating with said fifth inhibit means for providing an display indicia of exposure upon generation of said trigger signal until the next regeneration of said arm signal.

8. The apparatus of claim 3 further including means for providing an display indicia of the need to regenerate the arm signal after the passing of a predetermined number of breaths.

* * * * *